United States Patent
Chen et al.

(10) Patent No.: US 11,939,378 B2
(45) Date of Patent: *Mar. 26, 2024

(54) COSTIMULATORY B7-H1 IN RENAL CELL CARCINOMA PATIENTS: INDICATOR OF TUMOR AGGRESSIVENESS AND POTENTIAL THERAPEUTIC TARGET

(71) Applicant: Mayo Foundation for Medical Education and Research, Rochester, MN (US)

(72) Inventors: Lieping Chen, Hamden, CT (US); Scott E. Strome, Rochester, MN (US); Eugene D. Kwon, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 285 days.

This patent is subject to a terminal disclaimer.

(21) Appl. No.: 17/402,262

(22) Filed: Aug. 13, 2021

(65) Prior Publication Data

US 2021/0380690 A1    Dec. 9, 2021

Related U.S. Application Data

(63) Continuation of application No. 16/544,357, filed on Aug. 19, 2019, now Pat. No. 11,242,387, which is a continuation of application No. 15/890,048, filed on Feb. 6, 2018, now abandoned, which is a continuation of application No. 15/069,258, filed on Mar. 14, 2016, now abandoned, which is a continuation of application No. 14/264,568, filed on Apr. 29, 2014, now abandoned, which is a continuation of application No. 13/012,063, filed on Jan. 24, 2011, now Pat. No. 8,747,833, which is a continuation of application No. 11/245,713, filed on Oct. 6, 2005, now Pat. No. 7,892,540.

(60) Provisional application No. 60/642,794, filed on Jan. 11, 2005, provisional application No. 60/616,590, filed on Oct. 6, 2004.

(51) Int. Cl.

| | | |
|---|---|---|
| *A61K 39/00* | (2006.01) |
| *A61K 38/20* | (2006.01) |
| *A61K 38/21* | (2006.01) |
| *C07K 16/28* | (2006.01) |
| *C07K 16/30* | (2006.01) |
| *C12N 15/113* | (2010.01) |
| *C12Q 1/6886* | (2018.01) |
| *G01N 33/50* | (2006.01) |
| *G01N 33/569* | (2006.01) |
| *G01N 33/574* | (2006.01) |

(52) U.S. Cl.
CPC ...... *C07K 16/2803* (2013.01); *A61K 38/2013* (2013.01); *A61K 38/2026* (2013.01); *A61K 38/2066* (2013.01); *A61K 38/208* (2013.01); *A61K 38/2086* (2013.01); *A61K 38/212* (2013.01); *A61K 38/215* (2013.01); *A61K 38/217* (2013.01); *C07K 16/2827* (2013.01); *C07K 16/30* (2013.01); *C12N 15/113* (2013.01); *C12N 15/1138* (2013.01); *C12Q 1/6886* (2013.01); *G01N 33/5088* (2013.01); *G01N 33/5091* (2013.01); *G01N 33/56972* (2013.01); *G01N 33/57407* (2013.01); *G01N 33/57438* (2013.01); *G01N 33/57484* (2013.01); *A61K 2039/505* (2013.01); *C07K 2317/24* (2013.01); *C07K 2317/76* (2013.01); *C12N 2310/11* (2013.01); *C12N 2310/14* (2013.01); *C12N 2320/30* (2013.01); *C12Q 2600/106* (2013.01); *C12Q 2600/118* (2013.01); *C12Q 2600/158* (2013.01)

(58) Field of Classification Search
CPC .. C07K 16/2827; C07K 16/30; C12N 15/113; C12N 15/1138; C12Q 1/6886; G01N 33/57484; A61K 2039/505
See application file for complete search history.

(56) References Cited

U.S. PATENT DOCUMENTS

| | | |
|---|---|---|
| 3,687,808 A | 8/1972 | Merigan et al. |
| 4,034,074 A | 7/1977 | Miles |
| 4,036,945 A | 7/1977 | Haber |
| 4,098,876 A | 7/1978 | Piasio et al. |
| 4,233,402 A | 11/1980 | Maggio et al. |
| 4,257,774 A | 3/1981 | Richardson et al. |
| 4,272,398 A | 6/1981 | Jaffe |
| 4,331,647 A | 5/1982 | Goldenberg |
| 4,376,110 A | 3/1983 | David et al. |
| 4,469,863 A | 9/1984 | Ts'o et al. |
| 4,650,764 A | 3/1987 | Temin et al. |

(Continued)

FOREIGN PATENT DOCUMENTS

| | | |
|---|---|---|
| CA | 2383424 | 3/2001 |
| CA | 2383456 | 3/2001 |

(Continued)

OTHER PUBLICATIONS

Abbaszadegan et al., Cancer Res, 54:4676-4679, 1994.

(Continued)

*Primary Examiner* — Lei Yao
(74) *Attorney, Agent, or Firm* — Fish & Richardson P.C.

(57) ABSTRACT

The invention features methods of diagnosis by assessing B7-H1 expression in a tissue from a subject that has, or is suspected of having, cancer, methods of treatment with agents that interfere with B7-H1-receptor interaction, methods of selecting candidate subjects likely to benefit from cancer immunotherapy, and methods of inhibiting expression of B7-H1.

3 Claims, 6 Drawing Sheets
Specification includes a Sequence Listing.

(56) References Cited

U.S. PATENT DOCUMENTS

| | | |
|---|---|---|
| 4,769,330 A | 9/1988 | Paoletti et al. |
| 4,816,567 A | 3/1989 | Cabilly et al. |
| 4,861,627 A | 8/1989 | Mathiowitz et al. |
| 4,861,719 A | 8/1989 | Miller |
| 4,925,673 A | 5/1990 | Steiner et al. |
| 4,946,778 A | 8/1990 | Ladner et al. |
| 4,980,289 A | 12/1990 | Temin et al. |
| 4,987,071 A | 1/1991 | Cech et al. |
| 5,013,556 A | 5/1991 | Woodle et al. |
| 5,124,263 A | 6/1992 | Temin et al. |
| 5,155,020 A | 10/1992 | Paoletti |
| 5,155,027 A | 10/1992 | Sledziewski et al. |
| 5,175,099 A | 12/1992 | Wills |
| 5,204,243 A | 4/1993 | Paoletti |
| 5,214,136 A | 5/1993 | Lin et al. |
| 5,218,105 A | 6/1993 | Cook et al. |
| 5,225,336 A | 7/1993 | Paoletti |
| 5,225,538 A | 7/1993 | Capon et al. |
| 5,225,539 A | 7/1993 | Winter |
| 5,235,033 A | 8/1993 | Summerton et al. |
| 5,240,846 A | 8/1993 | Collins et al. |
| 5,254,678 A | 10/1993 | Haseloff et al. |
| 5,278,056 A | 1/1994 | Bank et al. |
| 5,284,656 A | 2/1994 | Platz et al. |
| 5,296,347 A | 3/1994 | LaMotte, III |
| 5,451,569 A | 9/1995 | Wong et al. |
| 5,521,288 A | 5/1996 | Linsley et al. |
| 5,567,584 A | 10/1996 | Sledziewski et al. |
| 5,580,756 A | 12/1996 | Linsley et al. |
| 5,596,086 A | 1/1997 | Matteucci et al. |
| 5,629,204 A | 5/1997 | Honjo et al. |
| 5,674,704 A | 10/1997 | Goodwin et al. |
| 5,675,848 A | 10/1997 | Kappel |
| 5,698,520 A | 12/1997 | Honjo et al. |
| 5,714,147 A | 2/1998 | Capon et al. |
| 5,750,375 A | 5/1998 | Sledziewski et al. |
| 5,750,666 A | 5/1998 | Caruthers et al. |
| 5,827,516 A | 10/1998 | Urban et al. |
| 5,843,725 A | 12/1998 | Sledziewski et al. |
| 5,858,776 A | 1/1999 | Ostrand-Rosenberg et al. |
| 5,861,310 A | 1/1999 | Freeman et al. |
| 5,874,240 A | 2/1999 | Nr et al. |
| 5,928,893 A | 7/1999 | Kang et al. |
| 5,942,607 A | 8/1999 | Freeman et al. |
| 6,018,026 A | 1/2000 | Sledziewski et al. |
| 6,210,669 B1 | 4/2001 | Aniffo et al. |
| 6,210,892 B1 | 4/2001 | Bennett |
| 6,291,212 B1 | 9/2001 | Sledziewski et al. |
| 6,291,646 B1 | 9/2001 | Sledziewski et al. |
| 6,297,008 B1 | 10/2001 | Okamoto et al. |
| 6,300,099 B1 | 10/2001 | Sledziewski et al. |
| 6,303,121 B1 | 10/2001 | Kwon |
| 6,323,323 B1 | 11/2001 | Sledziewski et al. |
| 6,355,779 B1 | 3/2002 | Goodwin et al. |
| 6,423,885 B1 | 7/2002 | Waterhouse et al. |
| 6,458,934 B1 | 10/2002 | Hong et al. |
| 6,630,575 B2 | 10/2003 | Coyle et al. |
| 6,635,750 B1 | 10/2003 | Coyle et al. |
| 6,740,493 B1 | 5/2004 | Long et al. |
| 6,743,619 B1 | 6/2004 | Tang et al. |
| 6,803,192 B1 | 10/2004 | Chen |
| 6,808,710 B1 | 10/2004 | Wood et al. |
| 6,891,030 B2 | 5/2005 | Chen |
| 6,919,193 B2 | 7/2005 | Tang et al. |
| 6,936,704 B1 | 8/2005 | Freeman et al. |
| 6,943,150 B1 | 9/2005 | Altieri |
| 6,965,018 B2 | 11/2005 | Mikesell et al. |
| 7,029,674 B2 | 4/2006 | Carreno et al. |
| 7,030,219 B2 | 4/2006 | Pardoll et al. |
| 7,038,013 B2 | 5/2006 | Freeman et al. |
| 7,041,474 B2 | 5/2006 | Kingsbury |
| 7,101,550 B2 | 9/2006 | Wood et al. |
| 7,105,328 B2 | 9/2006 | Wood et al. |
| 7,122,351 B2 | 10/2006 | Moore et al. |
| 7,258,334 B2 | 8/2007 | Kim et al. |
| 7,279,567 B2 | 10/2007 | Mikesell et al. |
| 7,285,036 B2 | 10/2007 | Chang et al. |
| 7,358,354 B2 | 4/2008 | Mikesell et al. |
| 7,368,531 B2 | 5/2008 | Rosen et al. |
| 7,368,554 B2 | 5/2008 | Mikesell et al. |
| 7,381,794 B2 | 6/2008 | Moore et al. |
| 7,385,036 B2 | 6/2008 | Kingsbury |
| 7,411,051 B2 | 8/2008 | Rosen et al. |
| 7,414,122 B2 | 8/2008 | Fox et al. |
| 7,432,059 B2 | 10/2008 | Freeman et al. |
| 7,432,062 B2 | 10/2008 | Coyle et al. |
| 7,432,351 B1 | 10/2008 | Chen |
| 7,449,300 B2 | 11/2008 | Chen et al. |
| 7,560,540 B2 | 7/2009 | Pardoll et al. |
| 7,563,869 B2 | 7/2009 | Honjo et al. |
| 7,595,048 B2 | 9/2009 | Honjo et al. |
| 7,635,757 B2 | 12/2009 | Freeman et al. |
| 7,638,492 B2 | 12/2009 | Wood et al. |
| 7,651,686 B2 | 1/2010 | Chen |
| 7,709,214 B2 | 5/2010 | Freeman et al. |
| 7,723,479 B2 | 5/2010 | Mikesell et al. |
| 7,794,710 B2 | 9/2010 | Chen et al. |
| 8,039,589 B1 | 10/2011 | Chen |
| 8,053,414 B2 | 11/2011 | Pardoll et al. |
| 8,053,558 B2 | 11/2011 | Pardoll et al. |
| 8,114,845 B2 | 2/2012 | Langermann et al. |
| 8,163,550 B2 | 4/2012 | Chen et al. |
| 8,168,179 B2 | 5/2012 | Honjo et al. |
| 8,728,474 B2 | 5/2014 | Honjo et al. |
| 8,747,833 B2 | 6/2014 | Chen et al. |
| 9,803,015 B2 | 10/2017 | Chen et al. |
| 2002/0055139 A1 | 5/2002 | Holtzman et al. |
| 2002/0091246 A1 | 7/2002 | Pardoll et al. |
| 2002/0095024 A1 | 7/2002 | Mikesell et al. |
| 2002/0102651 A1 | 8/2002 | Freeman et al. |
| 2002/0106730 A1 | 8/2002 | Coyle et al. |
| 2002/0107363 A1 | 8/2002 | Fox et al. |
| 2002/0110836 A1 | 8/2002 | Freeman et al. |
| 2002/0164600 A1 | 11/2002 | Freeman et al. |
| 2002/0168719 A1 | 11/2002 | Kwon |
| 2003/0039653 A1 | 2/2003 | Chen et al. |
| 2003/0044768 A1 | 3/2003 | Wood et al. |
| 2003/0109434 A1 | 6/2003 | Algate et al. |
| 2003/0142359 A1 | 7/2003 | Bean et al. |
| 2003/0171551 A1 | 9/2003 | Rosenblatt et al. |
| 2003/0208058 A1 | 11/2003 | Fiscella et al. |
| 2003/0232323 A1 | 12/2003 | Freeman et al. |
| 2004/0010134 A1 | 1/2004 | Rosen et al. |
| 2004/0109847 A1 | 6/2004 | Chen et al. |
| 2004/0180047 A1 | 9/2004 | Chen et al. |
| 2004/0213795 A1 | 10/2004 | Collins et al. |
| 2004/0247563 A1 | 12/2004 | Lynch et al. |
| 2005/0013811 A1 | 1/2005 | Chen et al. |
| 2005/0059051 A1 | 3/2005 | Chen |
| 2005/0136049 A1 | 6/2005 | Ledbetter et al. |
| 2005/0228170 A1 | 10/2005 | Fox et al. |
| 2005/0260716 A1 | 11/2005 | Moore et al. |
| 2006/0034826 A1 | 2/2006 | Carreno et al. |
| 2006/0084794 A1 | 4/2006 | Rosen et al. |
| 2006/0110383 A1 | 5/2006 | Honjo et al. |
| 2006/0153841 A1 | 7/2006 | Freeman et al. |
| 2006/0159685 A1 | 7/2006 | Mikesell et al. |
| 2006/0223088 A1 | 10/2006 | Rosen et al. |
| 2006/0276422 A1 | 12/2006 | Usman et al. |
| 2007/0037206 A1 | 2/2007 | Rosen et al. |
| 2007/0041963 A1 | 2/2007 | Rosen et al. |
| 2007/0065427 A1 | 3/2007 | Freeman et al. |
| 2007/0092504 A1 | 4/2007 | Carreno et al. |
| 2007/0099833 A1 | 5/2007 | Rosen et al. |
| 2007/0122378 A1 | 5/2007 | Freeman et al. |
| 2007/0197904 A1 | 8/2007 | Viglianti et al. |
| 2007/0224663 A1 | 9/2007 | Rosen et al. |
| 2007/0231344 A1 | 10/2007 | Leadbetter et al. |
| 2008/0025979 A1 | 1/2008 | Honjo et al. |
| 2008/0118511 A1 | 5/2008 | Freeman et al. |
| 2008/0213778 A1 | 9/2008 | Holtzman et al. |
| 2008/0226662 A1 | 9/2008 | Pardoll et al. |
| 2008/0241175 A1 | 10/2008 | Pardoll et al. |
| 2009/0042292 A1 | 2/2009 | Chen |

(56) References Cited

U.S. PATENT DOCUMENTS

| | | |
|---|---|---|
| 2009/0075338 A1 | 3/2009 | Moore et al. |
| 2009/0176317 A1 | 7/2009 | Kwon et al. |
| 2009/0215084 A1 | 8/2009 | Kwon et al. |
| 2009/0269783 A1 | 10/2009 | Coyle et al. |
| 2009/0274666 A1 | 11/2009 | Chen |
| 2009/0297518 A1 | 12/2009 | Honjo et al. |
| 2009/0317368 A1 | 12/2009 | Chen |
| 2010/0015642 A1 | 1/2010 | Kwon et al. |
| 2011/0020325 A1 | 1/2011 | Kwon et al. |
| 2012/0065374 A1 | 3/2012 | Pardoll et al. |
| 2012/0065385 A1 | 3/2012 | Pardoll et al. |
| 2015/0044165 A1 | 2/2015 | Chen et al. |
| 2016/0245816 A1 | 8/2016 | Chen et al. |
| 2016/0257953 A1 | 9/2016 | Chen et al. |
| 2016/0264667 A1 | 9/2016 | Chen et al. |
| 2018/0100015 A1 | 4/2018 | Chen et al. |
| 2018/0179281 A1 | 6/2018 | Chen et al. |
| 2020/0002419 A1 | 1/2020 | Chen et al. |

FOREIGN PATENT DOCUMENTS

| | | |
|---|---|---|
| CA | 2389722 | 5/2001 |
| EP | 1074617 | 2/2001 |
| EP | 1456652 | 9/2004 |
| EP | 1537878 | 6/2005 |
| WO | WO1990007861 | 7/1990 |
| WO | WO1991010741 | 7/1991 |
| WO | WO1991011465 | 8/1991 |
| WO | WO1991017271 | 11/1991 |
| WO | WO1992000092 | 1/1992 |
| WO | WO1992001047 | 1/1992 |
| WO | WO1992020791 | 11/1992 |
| WO | WO1993001222 | 1/1993 |
| WO | WO1995005464 | 2/1995 |
| WO | WO1995007707 | 3/1995 |
| WO | WO1996029348 | 9/1996 |
| WO | WO1997017613 | 5/1997 |
| WO | WO1997017614 | 5/1997 |
| WO | WO1997024447 | 7/1997 |
| WO | WO1998016249 | 4/1998 |
| WO | WO1998023635 | 6/1998 |
| WO | WO1998033914 | 8/1998 |
| WO | WO1998036096 | 8/1998 |
| WO | WO1999036093 | 7/1999 |
| WO | WO1999064597 | 12/1999 |
| WO | WO2000029445 | 5/2000 |
| WO | WO2000029582 | 5/2000 |
| WO | WO2000041508 | 7/2000 |
| WO | WO2000055375 | 9/2000 |
| WO | WO2000061612 | 10/2000 |
| WO | WO2001014557 | 1/2001 |
| WO | WO2001007611 | 2/2001 |
| WO | WO2001014556 | 3/2001 |
| WO | WO2001034629 | 5/2001 |
| WO | WO2001034768 | 5/2001 |
| WO | WO2001039722 | 6/2001 |
| WO | WO2001062905 | 8/2001 |
| WO | WO2001070979 | 9/2001 |
| WO | WO2001083750 | 11/2001 |
| WO | WO2001094413 | 12/2001 |
| WO | WO2002000692 | 1/2002 |
| WO | WO2002000730 | 1/2002 |
| WO | WO2002002587 | 1/2002 |
| WO | WO2002002891 | 1/2002 |
| WO | WO2002008279 | 1/2002 |
| WO | WO2002024891 | 3/2002 |
| WO | WO2002046449 | 6/2002 |
| WO | WO2002057453 | 7/2002 |
| WO | WO2002078731 | 10/2002 |
| WO | WO2002079474 | 10/2002 |
| WO | WO2002081731 | 10/2002 |
| WO | WO2002086083 | 10/2002 |
| WO | WO2003006632 | 1/2003 |
| WO | WO2003008583 | 1/2003 |
| WO | WO2003049755 | 6/2003 |
| WO | WO2004004771 | 1/2004 |
| WO | WO2004056875 | 7/2004 |
| WO | WO2004073732 | 9/2004 |
| WO | WO2004077060 | 9/2004 |
| WO | WO2005007855 | 1/2005 |
| WO | WO2006050172 | 5/2006 |
| WO | WO2006133396 | 12/2006 |
| WO | WO2007100098 | 9/2007 |
| WO | WO2008037080 | 4/2008 |
| WO | WO2008083174 | 7/2008 |
| WO | WO2009023566 | 2/2009 |
| WO | WO2009029342 | 3/2009 |
| WO | WO2009114110 | 9/2009 |
| WO | WO2010027423 | 3/2010 |
| WO | WO2010027827 | 3/2010 |
| WO | WO2010027828 | 3/2010 |
| WO | WO2010098788 | 9/2010 |
| WO | WO2011066342 | 6/2011 |

OTHER PUBLICATIONS

Abstract—EBI Database Accession No. AF177937 XP002269036 (version 1 accession date: Jan. 19, 2000).
Abstract—UNIPROT Database Accession No. Q9EP73 XP002269038 (Version 1 accession date: Mar. 1, 2001).
Abstract—UNIPROT Database Accession No. Q9NZQ7 XP002269037 (version 1 accession date Oct. 1.2000).
Acsadi et al., "Direci gene transfer and expression into rat heart in vivo," The New Biologist, vol. 3, No. 1, Jan. 1991, pp. 71-81.
Adachi et al., "Aberrant transcription caused by the insertion of an early transposable element in an intron of the Fas antigen gene of lpr mice," Proc. Natl. Acad. Sci, USA, vol. 90, Mar. 1993, pp. 1756-1760.
Adachi et al., "Enhanced and accelerated lymphoproliferation in Fas-null mice.," Proc. Natl. Acad. Sci. USA, vol. 93, Mar. 1996, pp. 2131-2136.
Agata et al., "Expression of the PD-1 antigen on the surface of stimulated mouse T and B lymphocytes", International Immunology, vol. 8, No. 5, 1996, pp. 765-772.
Alderson et al., "Molecular and biological characterization of human 4-IBB and its ligand," Eur. J. Immunol., vol. 24, 1994, pp. 2219-2227.
Aldovini et al., "Humoral and cell-mediated immune responses to live recombinant BCG-HIV vaccines," Nature, vol. 351. Jun. 6, 1991, pp. 479-482.
Ambrosini et al. "A novel anti-apoptosis gene, survivin, expressed in cancer and lymphoma," Nature Medicine, vol. 3, No. 8, Aug. 1997, pp. 917-921.
Anderson, "Human Gene Therapy," Science, vol. 256, May 8, 1992, pp. 808-813.
Ansari et al., "The programmed death-1 (PD-1) pathway regulates autoimmune diabetes in nonobese diabetic (NOD) mice," J. Exp. Med., vol. 198, No. 1, Jul. 7, 2003, pp. 63-69.
Anukam et al., "Augmentation of antimicrobial metronidazole therapy of bacterial vaginosis with oral probiotic Lactobacillus rhamnosus GR-1 and Lactobacillus reuteri RC-14: randomized, double-blind, placebo controlled trial," Microbes and Infection, 2006, pp. 1-5.
ASCO 2010 Press Release "Ipilimumab Improves Survival for Patients with Metastatic Melanoma." ASCO Meeting, Jun. 2010.
Atkins et al., "Update on the role of interleukin 2 and other cytokines in the treatment of patients with stage IV renal carcinoma," Clinical Cancer Research, 10(18):6342-6346, Sep. 2004.
Attwood et al., "The Babel of Bioinformatics." Science, Oct. 20, 2000, vol. 290, pp. 471-473.
Azuma et al., "B70 antigen is a second ligand for CTLA-4 and CD28," Nature, vol. 366, Nov. 4. 1993, pp. 76-79.
Bajorath et al., "Immunoglobulin fold characteristics of B7-1 (CD80) and B7-2 (CD86)," Protein Science, vol. 3, Nov. 1994, pp. 2148-2150.
Bajorath et al., "Molecular modeling of CD28 and three-dimensional analysis of residue conservation in the CD28/CD152 family", Journal of Molecular Graphics and Modelling, vol. 15, 1997, pp. 135-139.

(56) References Cited

OTHER PUBLICATIONS

BD PharmingenTM Technical Data Sheet, "Purified Rat Anti-Mouse Ly-6G (Gr-1) Monoclonal Antibody for Immunohistochemistry (IHC)," 2003, 1 page.
Bell, "B7h and B7-H1: new members of the B7 family", Immunology Today, vol. 21, No. 1, Feb. 2000. p. 59.
Benita et al., "Characterization of drug-loaded poly(d,l-lactide) microspheres," Journal of Pharmaceutical Sciences, vol. 73, No. 12, Dec. 1984, pp. 1721-1724.
Benlalam et al., "Comprehensive analysis of the frequency of recognition of melanoma-associated antigen (MAA) by CD8 melanoma infiltrating lymphocytes (TIL) implications for immunotherapy," Eur. J. Immunol, vol. 31, 2001, pp. 2007-2015.
Bennett et al., "Program Death-1 Engagement Upon TCR Activation Has Distinct Effects on Costimulation and Cytokine-Driven Proliferation: Attenuation of ICOS, IL-4, and IL-21, But Not CD28, IL-7, and IL-15 Responses," J Immunol., 170(2):711-718, Jan. 15, 2003.
Berman et al., "The Protein Data Bank" Nucleic Acids Research, 2000, vol. 28, No. 1, pp. 235-242.
Blank et al., "Blockade of PD-L1 (B7-H1) augments human tumor-specific T cell responses in vitro," Int. J. Cancer, vol. 119, 2006, pp. 317-327 (Published online Feb. 16, 2006).
Blank et al., "PD-L1/B7H-I inhibits the effector phase of tumor rejection by T cell receptor (TCR) transgenic CD8+ T cells," Cancer Research, 64(3):1140-1145, Feb. 2004.
Blazar et al. "Blockade of Programmed DeathI1 Engagement Accelerates Graft-Versus-Host Disease Lethality by an IFN-γ Dependent Mechanism1," J Immunol., 171:1272-1277, 2003.
Blazar et al., "Infusion of Anti-B7.1 (CD80) and Anti-B7.2 (CD86) Monoclonal Antibodies Inhibits Murine Graft-Versus-Host Disease Lethality in Part Via Direct Effects on CD4+ and CD8+ T Cells", Journal of Immunology, vol. 157, 1996, pp. 3250-3259.
Bodey (Expert Opinion Biological Therapy, 2001, 1(4):603-17).
Bodey et al, 2000, Anticancer Res, 20: 2665-2676.
Boletta et al., "High Efficient Non-Viral Gene Delivery to the Rat Kidney by Novel Polycationic Vectors," J. Am Soc. Nephrol., vol. 7, No. 9, Abstract A2409, S462 (PS), Sep. 1996, p. 1728.
Bolstad et al., "Increased Salivary Gland Tissue Expression of Fas, Fas Ligand, Cytotoxic T Lymphocyte—Associated Antigen 4, and Programmed Cell Death 1 in Primary Sjogren's Syndrome," Arthritis & Rheum., 48(1):174-185, Jan. 2003.
Bona et al., "Immune response: Idiotype anti-idiotype network," CRC Critical Reviews in Immunology, Mar. 1981, pp. 33-73.
Bonfoco et al., "Inducible nonlymphoid expression of Fas ligand is responsible for superantigen-induced peripheral deletion of T cells," Immunity, vol. 9, No. 5, 1998, pp. 711-720.
Bonifaz et al., "Efficient targeting of protein antigen to the dendritic cell receptor DEC-205 in the steady state leads to antigen presentation on major histocompatibility complex class I products and peripheral CD8+ T cell tolerance," J. Exp. Med, vol. 196, No. 12, Dee, 16, 2002, pp. 1627-1638.
Bonifaz et al., "In vivo targeting of antigens to maturing dendritic cells via the DEC-205 receptor improves T cell vaccination," J. Exp. Med, vol. 199, No. 6, Mar. 15, 2004, pp. 815-824.
Boon et al., "Human T Cell Responses Against Melanoma", Annu. Rev. Immunol., vol. 24, 2006, pp. 175-208 (Published online Dec. 1, 2005).
Boon, 1992 (Adv Can Res, 58:177-210).
Bovo et al., "Immune-mediated inner ear disease", Acta Oto-Laryngologica, vol. 126, 2006, pp. 1012-1021.
Bowie (Science, 1990, 257:1306-1310).
Brahmer et al. (J Clin Oncol 26: May 20, 2008, suppl; abstr 3006).
Braquet et al., "Effect of Endothelin-1 on Blood Pressure and Bronchopulmonary System of the Guinea Pig," Journal of Cardiovascular Pharmacology, vol. 13, Suppl. 5, 1989, pp. S143-S146.
Britton et al., "Leprosy," The Lancet, vol. 363, Apr. 10, 2004, pp. 1209-1219.

Brown et al., "Blockade of programmed death-1 ligands on dendritic cells enhances T cell activation and cytokine production," The Journal of Immunology, vol. 170, 2003, pp. 1257-1266.
Bubenik, "Genetically engineered dendritic cell-based cancer vaccines (Review)", International Journal of Oncology, vol. 18, 2001, pp. 475-478, XP001056627.
Burgess et al (J of Cell Bio. 111:2129-2138, 1990).
Burner et al., "Frequency and Spectrum of c-Ki-ras Mutations in Human Sporadic Colon Carcinoma, Carcinomas Arising in Ulcerative Colitis, and Pancreatic Adenocarcinoma," Environmental Health Perspectives, vol. 93, 1991, pp. 27-31.
Buskens et al., "Adenocarcinomas of the Gastro-Esophageal Junction: A Comparative Study of the Gastric Cardia and the Esophagus with Respect to Cyclooxygenase-2 Expression," Digestive Disease Week Abstracts and Itinerary Planner, Abstract No. 850.2003.2003, 2003.
Butte et al., "Interaction of human PD-L1 and B7-1," Molecular Immunology, vol. 45, 2008, pp. 3567-3572 (Published online Jun. 27, 2008).
Cairns et al., "Immortalization of multipotent growth-factor dependent hemopoietic progenitors from mice transgenic for GATA-1 drive SV40 tsA58 gene," The EMBO Journal, vol. 13, No. 19, 1994, pp. 4577-4586.
Carreno et al., "The B7 family of ligands and its receptors: new pathways for costimulation and inhibition of immune responses," Annu. Rev. Immunol., vol. 20, 2002, pp. 29-53.
Carter et al., "Humanization of an anti-p185HER2 antibody for human cancer therapy," Proc. Natl. Acad. Sci. USA, vol. 89, May 1992, pp. 4285-4289.
Carter et al., "PD-1:PD-1, inhibitory pathway affects both CD4+ and CD8+ T cells and is overcome by IL-2," Eur. J. Immunol., vol. 32, 2002, pp. 634-643.
Chakrabarti et al., "Vaccinia virus expression vector: coexpression of beta.-galactosidase provides visual screening of recombinant virus plaques," Molecular and Cellular Biology, vol. 5, No. 12, Dec. 1985, pp. 3403-3409.
Chambers et al., "Co-stimulation in T cell responses," Current Opinion in Immunology, vol. 9, 1997, pp. 396-404.
Chapoval et al., "B7-H3: A costimulatory molecule for T cell activation and IFN-.UPSILON. production, " Nature Immunology, vol. 2, No. 3, Mar. 2001, pp. 269-274.
Chaurand et al., "Peptide and Protein Identification by Matrix-Assisted Laser Desorption Ionization (MALDI) and MALDI-Post-Source Decay Time-of-Flight Mass Spectrometry," J Am Soc Mass Spectrom, vol. 10, 1999, pp. 91-103.
Chen et al., "CD44-deficient mice exhibit enhanced hepatitis after concanavalin A injection: evidence for involvement of CD44 in activation-induced cell death," The Journal of Immunology, vol. 166, 2001, pp. 5889-5897.
Chen et al., "Costimulation of antitumor immunity by the B7 counterreceptor of the T lymphocyte molecules CD28 and CTLA-4," Cell, vol. 71, Dec. 24, 1992, pp. 1093-1102.
Chen et al., "Tumor immunogenicity determines the effect of B7 costimulation on T cell-mediated tumor immunity," J. Exp. Med., vol. 179, Feb. 1994, pp. 523-532.
Chen, "Co-inhibitory molecules of the B7-CD28 family in the control of T-cell immunity, " Nature Reviews | Immunology, vol. 4, May 2004, 336-347.
Cheville et al., "Comparisons of Outcome and Prognostic Features Among Histologie Subtypes of Renal Cell Carcinoma," Am. J. Surg Pathol., vol. 27, No. 5, 2003, pp. 612-624.
Chor et al., "Genomic Organization and expression Analysis of B7-H4, an Immune Inhibitory Molecule of the B7 Family," The Journal of Immunology, vol. 171, 2003, pp. 4650-4654.
Clinical Trials Database on phase I clinical trials using an anti-hB7-HI monoclonal antibody (ID No. NCT00729664).
ClinicalTrials.gov., Study of MDX-1105 in Subjects with Selected Advanced or Recurrent Solid Tumors (MDX1105-01), verified by Bristol-Myers Squibb, Mar. 29, 2010.
Cogoni et al., "Gene silencing in Neurospora crassa requires a protein homologous to RNA-dependent RNA polymerase," Nature, vol. 399, May 13, 1999, 166-169.

(56) References Cited

OTHER PUBLICATIONS

Cogoni et al., "Transgene silencing of the al-1 gene in vegetative cells of Neurospora is mediated by a cytoplasmic effector and does not depend on DNA-DNA interactions of DNA methylation," The EMBO Journal, vol. 15, No. 12, 1996, pp. 3153-3163.
Cohen et al., "Lpr and gld: Single Gene Models of Systemic Autoimmunity and Lymphoproliferative Disease," Annu. Rev. Immunol., vol. 9, 1991, pp. 243-269.
Cole et al., "The EBV-Hybridoma Technique and its Application to Human Lung Cancer;" Monoclonal Antibodies and Cancer Therapy, 1985, pp. 77-96.
Collins et al., "The B7 family of immune-regulatory ligands," Genome Biology, vol. 6, Issue 6, Article 223, May 31, 2005, pp. 223.1-223.7.
Cone et al., "High-efficiency gene transfer into mammalian cells: Generation of helper-free recombinant retrovirus with broad mammalian host range." Proc. Natl. Acad Sci. USA, vol. 81, Oct. 1984, pp. 6349-6353.
Connolly, "Analytical Molecular Surface Calculation," Journal of Applied Crystallography, vol. 16, 1983, pp. 548-558.
Corpet, "Multiple sequence alignment with hierachical clustering," Nuclelic Acids Research, vol. 16, No. 22, 1988, pp. 10881-10890.
Cote et al., "Generation of human monoclonal antibodies reactive with cellular antigens," Proc. Natl. Acad. Sci. USA, vol. 80, Apr. 1983, pp. 2026-2030.
Coyle et al., "The expanding B7 superfamily: Increasing complexity in costimulatory signals regulating T cell function," Nature Immunology, vol. 2, No. 3, Mar. 2001, pp. 203-209.
Crispe et al., "The liver as a site of T-cell apoptosis: graveyard, or killing field?", Immunological Reviews, vol. 174, 2000, pp. 47-62.
Crispe, "Hepatic T Cells and Liver Tolerance," Natute Reviews | Inununology, vol. 3, Jan. 2003, pp. 51-62.
Cristiano et al., "Molecular conjugates: a targeted gene delivery vector for molecular medicine," J. Mol. Med., vol. 73, 1995, pp. 479-486.
Crystal, "Gene therapy strategies for pulmonary disease," The American Journal of Medicine, vol. 92, Suppl. 6A, Jun. 22, 1992, pp. 6A-44S to 6A-52S.
Curiel et al. "Blockade of B7-H1 improves myeloid dendritic cell—mediated antitumor immunity" Nat Med. May 2003:9(5):562-567.
Dao et al., "Involvement of CDI in peripheral deletion of T lymphocytes is independent of NK T cells," The Journal of Immunology, vol. 166, 2001, pp. 3090-3097.
Database EM-HUM [Online] EMBL; Accession No. AK001872, Feb. 22, 2000.
Database EM-MUS [Online]EMBL; Accession No. AF142780.1 (version 1), Jun. 1, 1999.
Database WPI Week 200411 Thomson Scientific, London, GB; AN 2004-108719 XP002520406 & WO 2004/004771 A (HONJO T) Jan. 15, 2004 (Jan. 15, 2004), 2 pages.
Davidson et al., "Phenotypic, functional, and molecular genetic comparisons of the abnormal lymphoid cells of C3H-lpr/lpr and C3H-gld/gld MICE," The Journal of Immunology, vol. 136, No. 11, Jun. 1, 1986, pp. 4075-4084.
De St. Groth et al., "Production of monoclonal antibodies: strategy and tactics," Journal of Immunology Methods, vol. 35, 1980, pp. 1-21.
Debs et al., "Lung-specific delivery of cytokines induces sustained pulmonary and systemic immunomodulation in rats," The Journal of Immunology, vol. 140, No. 10, May 15, 1988, pp. 3482-3488.
Decision rejecting the opposition in European Patent EP1537878, dated Sep. 24, 2017, 24 pages.
Declaration of Professor Vassilki Boussiotis, Office of public records dated Apr. 27, 2020, 28 pages.
Dheda et al., "Lung remodelling in pulmonary tuberculosis," J. Infect. Dis., vol. 192, Oct. 1, 2005, pp. 1201-1210.
Diehl et al., "In Vivo Triggering Through 4-1BB Enables Th-Independent Priming of CTL in the Presence of an Intact CD28 Costimulatory Pathway", The Journal of Immunology, vol. 168, 2002, pp. 3755-3762, XP002238986.
Ding et al., "Release of Reactive Nitrogen Intermediates and Reactive Oxygen Intermediates from Mouse Peritoneal Macrophages," The Journal of Immunology, vol. 141, No. 7, Oct. 1, 1988, pp. 2407-2412.
Dini, "Recognizing death: liver phagocytosis of apoptotic cells," Eur. J. Histochem., vol. 44, 2000, pp. 217-227.
Dong et al., "B7-H1 determines accumulation and deletion of intrahepatic CD8+ T lymphocytes," Immunity, vol. 20, Mar. 2004, pp. 327-336.
Dong et al., "B7-H1 pathway and its role in the evasion of tumor immunity", J. Mol. Med., vol. 81, pp. 281-287 (2003).
Dong et al., "B7-H1, a third member of the B7 family, co-stimulates T-cell proliferation and interleukin-10 secretion", Nature Medicine, vol. 5, No. 12, Dec. 1999, pp. 1365-1369.
Dong et al., "Costimulating aberrant T cell responses by B7-H1 autoantibodies in rheumatoid arthritis", The Journal of Clinical Investigation, vol. 111, No. 3, Feb. 2003, pp. 363-370.
Dong et al., "Immune regulation by novel costimulatory molecules," Immunologic Research, vol. 28, No. 1, 2003, pp. 39-48.
Dong et al., "Tumor-associated B7-H1 promotes T-cell apoptosis: a potential mechanism of immune evasion," Nat Med., 8(8):793-800, Epub Jun. 24, 2002.
Dudler et al., "Gene transfer of programmed death Ligand-I.Ig prolongs cardiac allograft survival," Transplantation, vol. 82, No. 12, Dec. 27, 2006, pp. 1733-1737, XP008088691.
Dunussi-Joannopoulos et al., "Gene Therapy with B7.1 and GM-CSF Vaccines in a Murine AML Model," Journal of Pediatric Hematology/Oncology, vol. 19, No. 6, 1997, pp. 536-540.
Dutcher, Current status of interleukin-2 therapy for metastatic renal cell carcinoma and metastatic melanoma., Oncology, 16(11 Suppl 13):4-10, 2002.
Ehl et al., "Different susceptibility of cytotoxic T cells to CD95 (Fas/Apo-1) ligand-mediated cell death after activation in vitro versus in vivo," The Journal of Immunology, vol. 156, 1996, pp. 2357-2360.
EMBL-EBI Accession No. AF 142780.2 (version 2, accessed Apr. 28, 2009) (Jun. 1, 1999).
EMBL-EBI Accession No. Q9WUL5 (Nov. 1, 1999).
Engh et al. "Accurate Bond and Angle Parameters for X-ray Protein Structure Refinement", Acta Cryst., vol. A47, 1991, pp. 392-400.
Eszter et al., "Crystal structure of the complex between programmed death-1 (PD-1) and its ligand PD-I.2," Proc. Natl. Acad. Sci. USA., 105(30):10483-10488, Jul. 2008.
European Medicines Agency, "Opdivo (nivolumab): An overview of Opdivo and why it is authorised in the EU," Dec. 2018, 5 pages.
European Notice of Opposition in European Patent No. EP1810026 dated Jan. 25, 2019, 18 pages.
European Search Report and Opinion for Application No. 05808659.6, dated Apr. 8, 2009, 15 pages.
Experimental Data generated by a licensee of the present application (Date Unknown).
Extended European Search Report in European Application No. 18167823.6 dated Nov. 13, 2018, 531 pages.
Falkner et al., "pUV I: a new vaccinia virus insertion and expression vector;" Nucleic Acids Research, vol. 15, No. 17, 1987, p. 7192.
Fargeas et al., "Identification of Residues in the V Domain of CD80 (B7-1) Implicated in Functional Interactions with CD28 and CTLA4," J. Exp. Med., vol. 182, Sep. 1995, pp. 667-675.
FDA News Release "FDA Approves a Cellular Immunotherap Advanced Prostate Cancer," Apr. 29, 2010.
Fechteler et al., "Prediction of Protein Three-dimensional Structures in Insertion aad Deletion Regions: A Procedure for Searching Data Bases of Representative Protein Fragments Using Geometrie Scoring Cateria" J. Mol. Biol., vol. 253, 1995, pp. 114-131.
Figlin et al., "Treatment of Metastatic Renal Cell Carcinoma with Nephrectomy, Interleukin-2 and Cytokine-Primed of CD8(+) Selected Tumor Infiltrating Lymphocytes From Primary Tumor," The Journal of Urology, vol. 158, Sep. 1997, pp. 740-745.
Finck et al., "Treatment of Murine Lupus with CTLA4Ig," Science, vol. 265, Aug. 26, 1994, pp. 1225-1227.

(56) References Cited

OTHER PUBLICATIONS

Fire et al., "Potent and specific genetic interference by double-stranded RNA in Caenorhabditis elegans," Nature, vol. 391, Feb. 19, 1998, pp. 806-811.
Fleming et al., "Selective Expression of Ly-6G on Myeloid Lineage Cells in Mouse Bone Marrow," The Journal of Inimionology, vol. 151, No. 5, Sep. 1, 1993, pp. 2399-2408.
Flies et al., "Blockade of the B7-H1/PD-I pathway for cancer immunotherapy," Yale J Biol Med., 84(4):409-421, Dec. 2011.
Foell et al., "CD137 costimulatory T cell receptor engagement reverses acute disease in lupus-prone NZB.times.NZW F1 mice," The Journal of Clinical Investigation, vol. 111, No. 10, May 2003, pp. 1505-1518.
Foell et al., "CD137-Mediated T Cell Co-Stimulation Terminates Existing Autoimmune Disease in SLE-Prone NZB/NZW F1 Mice," Ann. N.Y. Acad. Sci., vol. 987, 2003, pp. 230-235, XP009028987.
Fortugno et al., "Survivin exists in inmunochemically distinct subcellular pools and is involved in spindle microtubule function," Journal of Cell Science, vol. 115, 2002, pp. 575-585.
Frank et al., "An Outcome Prediction Model for Patients With Clear Cell Renal Cell Carcinoma Treated With Radical Nephrectomy Based on Tumor Stage, Size, Grade and Necrosis: The SSIGN Score," The Journal of Urology, vol. 168, Dec. 2002, pp. 2395-2400.
Freeman et al., "B7, A New Member of the Ig Superfamily with Unique Expression on Activated and. Neoplastic B Cells," The Journal of Immunology, vol. 143, No. 8, Oct. 15, 1989, pp. 2714-2722.
Freeman et al., "B7-1 and B7-2 Do Not Deliver Identical Costiniatory Signals, Since B7-2 but Not B7•1 Preferentially Costimulates the Initial Production of IL•4," Immunity, vol. 2, May 1995, pp. 523-532.
Freeman et al., "Cloning of B7-2: A CTLA-4 Counter-Receptor that Costimulates Hamban T Cell Proliferation," Science, vol. 262, Nov. 5, 1993, pp. 909-911.
Freeman et al., "Engagement of the PD-1 Inmunoinhibitory Receptor by a Novel B7 Family Member Leads to Negative Regulation of Lymphocyt Activation", J. Exp. Med., vol. 192, No. 7, Oct. 2, 2000, pp. 1027-1034.
Freeman et al., "Murine B7-2, an Alternative CTLA4 Counter-receptor that Costimulates T Cell Proliferation and Imerleukin 2 Production," The Journal of Experimental Medicine, vol. 178, Dec. 1993, pp. 2185-2192.
Freeman et al., "Protect the killer: CTLs need defenses against the tumor", Nature Medicine, vol. 8, No. 8, pp. 787-789, Aug. 2002.
Freeman et al., "Structure, Expression, and T Cell Costimulatory Activity of the Marine Homologue of the Human B Lymphocyte Activation Antigen B7," J. Exp. Med., vol. 174, Sep. 1991, pp. 625-631.
Frigola et al., "Identification of a Soluble Form of B7-H1 That Retains Immunosuppressive Activity and Is Associated with Aggressive Renal Cell Carcinoma," Clin Cancer Res, vol. 17, No. 7, 2011, pp. 1915-1923 (Published online Feb. 25, 2011).
Fuerst et al., "Transfer of the inducible lac repressor/operator system from *Escherichia coli* to a vaccinia virus expression vector," Proc. Natl. Acad. Sci. USA, vol. 86, Apr. 1989, pp. 2549-2553.
Fyfe et al., "Results of Treatment of 255 Patients with Metastatic Renal Cell Carcinoma Who Received High-Dose Recombinant Interlekin-2 Therapy," Journal of Clinical Oncology, vol. 13, No. 3, Mar. 1995, pp. 688-696.
GenBank Accession No. AAC51660, dated Sep. 2004.
GenBank Accession No. AK001872.1,"*Homo sapiens* cDNA FIJ11010 fis, clone PLACE1003145," pp. 1-2, (submitted Feb. 16, 2000).
GenBank Accession No. AL. 162253, "Human DNA sequence from clone RP11-574F11 on chromosome 9 contains the gene for B7-H1 protein (PD-L1), the gene for programmed death ligan 2 (PDL2) (PDCDIL2) and a novel gene," pp. 1-36 (Mar. 24, 2000).
GenBank Accession No. U75285, dated Sep. 2004.
GenBank under Accession No. AAF25807, Jan. 18, 2000, 1 page.
GenBank under Accession No. AAP37283, Jun. 1, 2003, 1 page.
GenBank under Accession No. AF177937, Jan. 18, 2000, 1 page.
GenBank under Accession No. AY280972, Jun. 1, 2003, 1 page.
Gerstmayer et al., "Costimulation of T eell proliferation by a chimeric B7-2 antibody fusion protein specifically targeted to cells expressing the erbB2 proto-oncogene," The Journal of Immunology, vol. 158, 1997, pp. 4584-4590 , XP002116142.
Gerstmayer et al., "Costimulation of T-cell proliferation by a chimeric B7-antibody fusion protein," Cancer Immunology Immunotherapy, vol. 45, 1997, pp. 156-158, XP002932422.
Gevaert et al., "Protein identification based on matrix assisted laser desorption ionization-post source decay-mass spectrometry," Electrophoresis, vol. 22, 2001, pp. 1645-1651.
Ghebeb et al. "The B7-H1 (PD-L1) T lymphocyte-inhibitory molecule is expressed in breast cancer patients with infiltrating ductal carcinoma: correlation with important high-risk prognostic factors." (Neoplasia, Mar. 2006; 8(3): 190-198).
Gimmi et al., "B-cell surface antigen B7 provides a costimulatory signal that induces T cells to proliferate and secrete interleukin 2," Proc. Natl. Acad. Sci. USA, vol. 88, Aug. 1991, pp. 6575-6579.
Goodwin et al., "Molecular Cloning and Expression of the Type I and Type 2 Murine Receptors for the Tumor Necrosis Factor," Molecular and Cellular Biology, vol. II, No. 6, Jun. 1991, pp. 3020-3026.
Goodwin et al., "Molecular cloning of a ligand for the inducible T cell gene 4-IBB: a member of an emerging family of cytokines with homology to tumor necrosis factor," Eur. J. Immunol., vol. 23, 1993, pp. 2631-2641.
Green et al., "Activation-induced cell death in T cells," Immunological Reviews, vol. 193, 2003, pp. 70-81.
Green et al., "Antigen-specific human monoclonal antibodies from mice engineered with human Ig heavy and light chain YACs," Nature Genetics, vol. 7, May 1994, pp. 13-21.
Greenwald et al., "The B7 family revisited," Annu. Rev. Immunol., vol. 23, 2005, pp. 515-548 (Published online Jan. 19, 2005).
Guatelli et al., "Isothermal, in vitro amplification of nucleic acids by a multienzyme reaction modeled after retroviral replication," Proc. Natl. Acad. Sci. USA, vol. 87, Mar. 1990, pp. 1874-1878.
Guinn et al., "4-1BBL Cooperates with B7-1 and B7-2 in Converting a B Cell Lymphoma Cell Line into a Long-Lasting Antitumor Vaccine," The Journal of Immunology, vol. 162, 1999, pp. 5003-5010.
Guo et al., "A novel fusion protein of IP10-scFv retains antibody specificity and chemokine function," Biochemical and Biophysical Research Communications, vol. 320 2004, pp. 506-513 (pp. 506-512 provided).
Haendeler et al., "Nitric Oxide and Apoptosis," Vitamins and Hormones, vol. 57, 1999, pp. 49-77.
Haidong et al., "Tumor-associated B7-H1 promotes T-cell apoptosis: a potential mechanism of immune evasion," Nat Med., 8(8):793-800, Aug. 2002.
Hatzoglou et el. "Hepatic gene transfer in animals using retroviruses containing the promoter from the gene for phosphoenolpyruvate carboxykinase" The Journal of Biological Chemistry, vol. 265, No. 28, Oct. 5, 1990, pp. 17285-17293.
Hawiger et al., "Dendritic cells induce peripheral T cell unresponsiveness under steady state conditions in vivo," J. Exp. Med., vol. 194, No. 6, Sep. 17, 2001, pp. 769-779.
He et al. "Blockade of B7-H1 with sPD-1 Improves Immunity against Murine Hepatocarcinoma," Anticancer Research Sep. 1, 2005 vol. 25 No. 5 3309-3313.
He et al., "Identification of a novel splice variant of human PD-L1 mRNA encoding an isoform-lacking Igv-like domain," Acta Pharmacol Sinica, vol. 26, Apr. 2005, pp. 462-468.
Hellstrom et al., "T Cell immunity to Tumor Antigens," Critical Reviews in Immunology, vol. 18, 1998, pp. 1-6.
Henkoff et al., "Amino acid substitution matrices from protein blocks," Proc. Natl. Acad. Sci USA, vol. 89, Nov. 1992, pp. 10915-10919.
Henry et al., "Cloning, structural analysis, and mapping of the B30 and B7 multigenic families to the major histocompatibility complex (MHC) and other chromosomal regions," Immunogenetics, vol. 46, 1997, pp. 383-395.

(56) References Cited

OTHER PUBLICATIONS

Henry et al., "Structure and evolution of the extended B7 family," Immunology Today, vol. 20, No. 6, Jun. 1999, pp. 285-288.
Hestdal et al., "Characterization and Regulation of RB6-8C5 Antigen Expression on Murine Bone Marrow Cells," The Journal of Immunology, vol. 147, No. 1, Jul. 1, 1991, pp. 22-28.
Hildeman et al., "Activated T cell death in vivo mediated by proapoptotic Bcl-2 family member bim," Immunity, vol. 16, Jun. 2002, pp. 759-767.
Hillman et al., "Systemic treatment with interleukin-4 induces regression of pulmonary metastases in a murine renal cell carcinoma model," Cell Immunol., 160(2):257-263, Feb. 1995.
Hirano et al. "Blockade of B7-H1 and PD-1 by monoclonal antibodies potentiates cancer therapeutic immunity," Cancer Res. Feb. 1, 2005;65(3):1089-1096.
Hiroshi et al., "Interferon-alpha gene therapy in combination with CD80 transduction reduces tumorigenicity and growth of established tumor in poorly immunogenie tumor models," Gene Therapy, vol. 6, 1999, pp. 1988-1994.
Hochman et al., "An active antibody fragment (Fv) composed of the variable portions of heavy and light chains," Biochemistry, vol. 12, No. 6, 1973, pp. 1130-1135.
Hock et al., "Retrovirus-mediated transfer and expression of drug resistance genes in human haematopoictic progenitor cells," Nature, vol. 320, Mar. 20, 1986, pp. 275-277.
Hodi et al. "Re-induction with ipilimumab, gp100 peptide vaccine, or a combination of both from a phase III, randomized, double blind, multicenter study of previously treated patients with unresectable stage III or IV melanoma." J Clin Oncol 28:15s, 2010 (suppl; abstr 8509).
Hoffman, "T Cells in the Pathogenesis of Systemie Lupus Erythematosus," Frontiers in Bioscience, vol. 6, Oct. 1, 2001, pp. d1369-d1378.
Hoiseth et al., "Aromatic-dependent *Salmonella typhimurium* are non-virulent and effective as live vaccines," Nature, vol. 291, May 21, 1981, pp. 238-239.
Hori et al., "B7-H1-Induced Apoptosis as a Mechanism of Immune Privilege of Corneal Allografts," The Journal of Immunology, vol. 177, 2006, pp. 5928-5935.
Huang et al., "The liver eliminates T cells undergoing antigen-triggered apoptosis in vivo," Immunity, vol. 1, Dec. 1994, pp. 741-749.
Huang, "Structural chemistry and therapeutic intervention of protein-protein interactions in immune response, human immunodeficiency virus entry, and apoptosis," Pharmacology & Therapeutics, vol. 86, 2000, pp. 201-215.
Hubbard et al., "Anti-neutrophil-elastase defenses of the lower respiratory tract in.alpha.1-antitrypsin deficiency directly augmented with an aerosol of alpha.1•antitrypsin," Annals of Internal Medicine, vol. 111, No. 3, Aug. 1, 1989, pp. 206-212.
Hunter, "Diabetes in pregnancy," Effective Care in Pregnancy and Childbirth, (Editors: Chalmers et al.), Oxford University Press, 1989, pp. 578-593.
Hase et al., "Generation of a Large Combinatorial Library of the Immunoglobulin Repertoire in Phage Lambda," Science, vol. 246, Dec. 8, 1989, pp. 1275-1281.
Hyrup et al., "Peptide Nucleic Acids (PNA): Synthesis, Properties and Potential Applications", Bioorganic & Medicinal Chemistry, vol. 4, No. 1, 1996, pp. 5-23.
Ichikawa et al., "Role of B7-H1 and B7-H4 molecules in down-regulating effector phase of T-cell immunity: novel cancer escaping mechanisms," Frontiers in Bioscience, vol. 10, 2005, pp. 2856-2860.
IDS submitted in U.S Appl. No. 10/890,789 concerning certain test data, filed Nov. 6, 2007.
Iehle, C et al, 1999, J Steroid Biochem Mol Biol, 68: 189-195.
Ikemizu et al., "Structure and Dimerization of a Soluble Form of B7-1", Immunity, vol. 12, Jan. 2000, pp. 51-60.

Ikonomidis, "Delivery of a viral antigen to the class I processing and presentation pathway by Listeria monocytogenes," J. Exp. Med., vol. 180, Dec. 1994, pp. 2209-2218.
Inaba et al., "The Tissue Distribution of the B7-2 Costimulator in Mice: Abundant Expression on Dendritic Cells In Situ and During Maturation In Vitro," J. Exp. Med., vol. 180, Nov. 1994, pp. 1849-1860.
India Office Action for Application No. 1940/CHENP/2007 dated Sep. 18, 2012.
Inman et al. "PD-L1 (B7-H1) Expression by Urothelial Carcinoma of the Bladder and BCG-Induced Granulomata," Cancer, vol. 109, 2007, pp. 1499-1505 (Published online Mar, 5, 2007).
Inman et al., "Questionable Relevance of.UPSILON.sigma. T Lymphocytes in Renal Cell Carcinoma," The Journal of Immunology, vol. 180, 2008, 3578-3584.
Ishida et al., "Differential expression of PD-L1 and PD-L2, ligands for an inhibitory receptor PD-1, in the cells of lymphohematopoietic tissues", Immunology Letters, vol. 84, 2002, pp. 57-62.
Ishida et al., "Induced expression of PD-1, a novel member of the immunoglobulin gene superfamily, upon programumed cell death," The EMBO Journal, vol. II, No. 11, 1992, pp. 3887-3895.
Iwai et al. "Involvement of PD-L1 on tumor cells in the escape from host immune system and tumor immunotherapy by PD-L1 blockade." Proc Natl Acad Sci U S A. Sep. 17, 2002;99(19):12293-12297.
Iwai et al., "Microanatomical localization of PD-1 in human tonsils," Immunol Lett., 83(3):215-220, 2002.
Iwai et al., "PD-1 blockade inhibits hematogenous spread of poorly immunogenie tumor cells by enhanced recruitment of effector T cells", International Immunology, vol. 17, No. 2, 2004, pp. 133-144.
Iwai et al., "PD-1 Inhibits Antiviral Immunity at the Effector Phase in the Liver," J. Exp. Med., vol. 198 No. 1, Jul. 7, 2003, pp. 39-50.
Jacobson et al., "Unique site of IgG2a and rheumatoid factor production in MRL/lpr mice," Immunological Reviews, vol. 156, 1997, pp. 103-110.
Jeannin et al., "Soluble CD86 is a costimulatory molecule for human T lymphocytes," Immunity, vol. 13, Sep. 2000, pp. 303-312.
Jemal et al., "Cancer Statistics, 2005," CA: A Cancer Journal for Clinicians, vol. 55, 2005, pp. 10-30.
Jerne, "Towards a network theory of the immune system," Ann. Immunol. (Inst. Pasteur.), vol. 125 C, 1974, pp. 373-389.
Johnston et al., "Biolistic Transformation of Animal Tissue," In Vitro Cell.Dev. Biol., vol. 27P, 1991, pp. 11-14.
Jones et al., "Replacing the complementarity-determining regions in a human antibody with those from a mouse," Nature, vol. 321, May 29, 1986, pp. 522-525.
Journal of Japan Surgical Society, vol. 105, Extra Edition, p. 258, SF-060-3 (Mar. 2004).
Juppner, "Functional Properties of the PTH/PTHrP Receptor," Bone, vol. 17, No. 2, Supplement, Aug. 1995, pp. 39S-42S.
Kaiser, 2006, Science, vol. 313, 1370.
Kaleko et al., "Persistent gene expression after retroviral gene transfer into liver cells in vivo," Human Gene Therapy, vol. 2, 1991, pp. 27-32.
Kaliyaperumal et al., "Antigen-Specific Therapy of Marine Lupus Nephritis Using Nucleosomal Peptides: Tolerance Spreading Impairs Pathogenic Function of Autoimmune T and B Cells," The Journal of Immunology, vol. 162, 1999, pp. 5775-5783 (22 pages provided).
Kalled et al., "Anti-CD40 Ligand Antibody Treatment of SNF1 Mice with Established Nephritis: Preservation of Kidney Function," The Journal of Immunology, vol. 160, 1998, pp. 2158-2165 (22 pages provided).
Kanai et al., "Blockade of B7-H1 suppresses the development of chronic intestinal inflammation," The Journal of Immunology, vol. 171, 2003, pp. 4156-4163.
Kaneko et al., "Augmentation of V.alpha.14 NKT cell-mediated cytotoxicity by interleukin 4 in an autocrine mechanism resulting in the development of concanavalin A-induced hepatitis," J. Exp. Med., vol. 191, No. 1, Jan. 3. 2000, pp. 105-114.
Kaplan et al., "Demonstration of an interferon gamma-dependent timor surveillance system in immunocompetent mice," Proc. Natl. Acad. Sci. USA, Jun. 1998, 95(13):7556-7561.

(56) References Cited

OTHER PUBLICATIONS

Kato et al., "5HT2A gene variants influence specific and different aspects of antidepressant response in Japanese and Italian mood disorder patients," Psychiatry Research, vol. 167, No. 1, 2009, pp. 97-105, Abstract only provided.
Kaofman et al., "A phase I trial of intra lesional RV-B7.1 vaccine in the treatment of malignant melanoma," Human Gene Therapy, vol. 11, May 1, 2000, pp. 1065-1082.
Kawabe et al., "Programmed cell death and extrathymic reduction of V.beta.8+ CD4+ T cells in mice tolerant to Staphylococcus aureus enterotoxin B," Nature, vol. 349, Jan. 17, 1991, pp. 245-248.
Kelley et al., "Cytokines in the Pathogenesis of Systemic Lupus erythematosus," Seminars in Nephrology, vol. 19, No. 1, Jan. 1999. pp. 57-66.
Kennerdell et al., "Use of dsRNA-Mediated Genetic Interference to demonstrate that frizzled and frizzled 2 Act in the Wingless Pathway," Cell, vol. 95, Dec. 23, 1998, pp. 1017-1026.
Kim et al., "State-of-the-Art Review. Therapeutic Potential of 4-1BB (CD137) As a Regulator for Effector CD8+ T Cells," Journal of Hematotherapy & Stem Cell Research, vol. 10, 2001, pp. 441-449.
Kirkin et al, 1998, APMIS, 106: 665-679.
Klippel, "Systemic Lupus Erythematosus: Demographics, Prognosis, and Outcome", J. Rheumatol., vol. 24, Suppl. 48, 1997, pp. 67-71.
Kohler et al., "Continuous cultures of fused cells secreting antibody of predefined specificity, " Nature, vol. 256, Aug. 7, 1975, pp. 495-497.
Kohn et al., "Gene therapy for genetic diseases," Cancer Investigation, vol. 7, No. 2, 1989, pp. 179-192.
Konishi et al. "B7-H1 Expression on Non-Small Cell Lung Cancer Cells and Its Relationship with Tumor-Infiltrating Lymphocytes and Their PD-1 Expression." (Clin Cancer Res 10, 5094-5100, 2004).
Korkola at al., "Gene expression-based classification of nonseminomatous male germ cell tumors," Oncogene, vol. 24, 2005, pp. 5101-5107 (Published online May 2, 2005).
Kosari et al., "Clear Cell Renal Cell Carcinoma: Gene Expression Analyses Identify a Potentional Signature for Tumor Aggressiveness," Clin Cancer Res, vol. 11, No. 14, Jul. 15, 2005, pp. 5128-5139.
Kozbor et al., "The production of monoclonal antibodies from human lymphocytes," Immunology Today, vol. 4, No. 3, 1983, pp. 72-79.
Krueger et al., "The role of CD95 in the regulation of peripheral T-cell apoptosis," Immunological Reviews, vol. 193, 2003, pp. 58-69.
Krummel et al., "CTLA-4 Engagement Inhibits IL-2 Accumulation and Cell Cycle Progression upon Activation of Resting T Cells," J. Exp. Med., vol. 183, Jun. 1996, pp. 2533-2540.
Kudo et al., "Gangliosides expressed by the renal cell carcinoma cell line SK-RC-45 are involved in tumor-induced apoptosis of T cells," Cancer Research, 63(7):1676-1683, Apr. 2003.
Kuiper et al., "B7.1 and cytokines Synergy in cancer gene therapy," Cancer Gene Therapy: Past Achievements and Future Challenges, (Editor: HABIB), Kluwer Academic/Plenum Publishers, 2000, pp. 381-390.
Kusmartsev et al., "Gr-1+ myeloid cells derived from tumor-bearing mice inhibit primary T cell activation induced through CD3/CD28 costimulation," The Journal of Immunology, vol. 165, 2000. pp. 779-785.
Kwon et al., "4-IBB: Still in the Midst of Darkness," Molecules and Cells, vol. 10, No. 2, 2000, pp. 119-126.
LaBaer et al., "So, You want to Look for Biomarkers (Introduction to the Special Biomarkers Issue)," Journal of Proteome Research, vol. 4, 2005, pp. 1053-1059 (Published online Jun. 30, 2005).
Latchman et al., "PD-L2 is a second ligand for PD-1 and inhibits T cell activation", Nature Immunology, vol. 2, No. 3, Mar. 2001, pp. 261-268.
Lawrence et al. "Phase II trial of ipilimumab monotherapy in melanoma." J Clin Oncol 28:15s, 2010 (suppl; absur 8523).
Lawson et al., "Treatment of marine lupus with cDNA encoding IFN-UPSILON.R/Fc," J. Clin. Invest. vol. 106, No. 2, 2000, pp. 207-215.
Lazar et al. (Molecular and Cellular Biology, 1988, 8:1247-1252).
Lázár-Molnár et al., "Crystal structure of the complex between programmed death-1 (PD-1) and its ligand PD-L2," Proc Natl Acad Sci U.S.A., 105(30);10483-10488. Epub Jul. 18, 2008.
Lederman et al., "A single amino acid substitution in a common African allele of the CD4 molecule ablates binding of the monoclonal antibody, OKT4," Molecular Immunology, vol. 28, No. 11, 1991, pp. 1171-1181.
Lee et al., "Increased vaccine-specific T cell frequency after peptide-based vaccination correlates with increased susceptibility to in vitro stimulation but does not lead to tumor regression," J Immunol., 163(11):6292-6300, Dec. 1, 1999.
Lee et al., "Survivin expression and its clinical significance in pancreatic cancer," BMC Cancer, Oct. 4, 2005, vol. 5, No. 127, 6 pages.
Leibovich et al., "Prediction of Progression After Radical Nephrectomy for Patients with Clear Cell Renal Cell Carcinoma," Cancer, vol. 97, 2003, pp. 1663-1671.
Lenardo et al., "Mature T lymphocyte apoptosis—immune regulation in a dynamic and unpredictable antigenic environment," Annu. Rev. Immunol., vol. 17, 1999, pp. 221-253.
Lenschow et al., "CD28/137 System of T Cell Costimulation," Annu. Rev. Immunol., vol. 14, 1996; pp. 233-258.
Levitt, "Accurate Modeling of Protein Conformation by Automatic Segment Matching, " J. Mol. Biol., vol. 226, 1992, pp. 507-533.
Lewinski et al., "Retroviral DNA integration: viral and cellular determinants of target-site selection," PLoS Pathogens, vol. 2, No. 6, e60, Jun. 23, 2006, pp. 0611-0621, XP002510754.
Lewis, "PCR's Competitors Are Alive and Well and Moving Rapidly Towards Commercialization," Genetic Engineering News, Jun. 1, 1992, vol. 12, No. 9, 3 pages.
Li et al., ".beta.-Endorphin omission analogs: Dissociation of immunoreactivity from other biological activities," PNAS, vol. 77, No. 6, Jun. 1980, pp. 3211-3214.
Li et al., "Fas-mediated apoptosis causes elimination of virus-specific cytotoxic T cells in the virus-infected liver," The Journal of Immunology, vol. 166, 2001, pp. 3035-3041.
Liang et al., "Autoantibody Responses and Pathology Regulated by B7-1 and B7-2 Costimulation in MRL/Ipr Lupus," The Journal of Immunology, vol. 165, 2000, pp. 3436-3443 (17 pages provided).
Linsley et al., "Binding of the B cells activation antigen B7 to CD28 costimulates T cell proliferation and interleukin 2 mRNA accumulation," J. Exp. Med., vol. 173, Mar. 1991, pp. 721-730.
Linsley et al., "Extending the B7 (CD80) gene family," Protein Science, vol. 3, 1994, pp. 1341-1343.
Linsley et al., "T-cell antigen CD28 mediates adhesion with B cells by interacting with activation antigen B7/BB-1," Proc. Nat. Acad. Sci. USA, vol. 87, Jul. 1990, pp. 5031-5035.
Liu et al., "B7-H1 on myeloid-derived suppressor cells in immune suppression by a mouse model of ovarian cancer," Clinical Immunology, vol. 129, 2008, pp. 471-481 (Published online Sep. 14, 2008).
Liu et al., B7DC/PDL2 promotes tumor immunity by a PD-1-independent mechanism, J. Exp. Med., vol. 197, No. 12, Jun. 16, 2003, pp. 1721-1730.
Lonberg et al., "Antigen specific human antibodies from mice comprising four distinct genetic modifications," Nature, vol. 368, Apr. 28, 1994, pp. 856-859.
Losman et al., "Baboon anti-idiotype antibodies mimic a carcinoembryonic antigen epitope," Int. J. Cancer, vol. 46, 1990, pp. 310-314.
Lu et al., "EGF-IL-18 fusion protein as a potential anti-tumor reagent by induction of immune response and apoptosis in cancer cells," Cancer Letters, vol. 260, 2008, pp. 187-197.
Luettig et al., "Naive and memory T lymphocytes migrate in comparable numbers through normal rat liver: activated T cells accumulate in the periportal feld," The Journal of Immunology, vol. 163, 1999, pp. 4300-4307.

(56) References Cited

OTHER PUBLICATIONS

Ma et al., "The Role of PD-1 Ligand in Immune Evasion by Breast Cancer," Dana-Farber Cancer Institute, Annual Summary Report, May 1, 2005, pp. 1-13.
Mackenzie, "New therapeutics that treat rheumatoid arthritis by blocking T-cell activation," Drug Discovery Today, vol. 11, Nos. 19/20, Oct. 2006, pp. 952-956.
Mahotka et al., "Distinct in vivo expression patterns of survivin splice variants in renal cell carcinomas," Int. J. Cancer, vol. 100, 2002, pp. 30-36.
Mann et al., "Construction of a retrovirus packaging mutant and its use to produce helper-free defective retrovirus," Cell, vol. 33, May 1983, pp. 153-159.
Martin et al. "Combination gene therapy with CD86 and the MHC Class II transactivator in the control of lung tumor growth," The Journal of Immunology, vol. 162, 1999, pp. 6663-6670.
Mathiowitz et al., "Morphology of polyanhydride microsphere delivery systems," Scanning Microscopy, vol. 4, No. 2, 1990, pp. 329-340.
Mathiowitz et al., "Novel microcapsules for delivery systems," Reactive Polymers, vol. 6, 1987, pp. 275-283.
Mathiowitz et al., "Polyanhydride microspheres as drug carriers. I. Hot-melt microencapsulation." Journal of Controlled Release, vol. 5, 1987, pp. 13-22.
Mathiowitz et al., "Polyanhydride microspheres as drug carriers. II. Microencapsulation by solvent removal," Journal of Applied Polymer Science, vol. 35, 1988, pp. 755-774.
Mathiowitz et al., "Polyanhydride microspheres. IV. Morphology and characterization of systems made by spray drying," Journal of Applied Polymer Science, vol. 45, 1992, pp. 125-134.
Matsumoto et al., "B7-DC Regulates Asthmatic Response by an IFN—Dependent Mechanism1," J Immunol., 172:2530-2541, 2004.
Mayo Clinic, "Mayo Clinic Discovers Potential Marker for Aggressive Kidney Cancer," Science Daily, Dec. 9, 2004, 3 pages URL: http://www.sciencedaily.com/releases/2004/11/041130200858.htm.
Mazanet et al. "B7-H1 Is Expressed by Human Endothelial Cells and Suppresses T Cell Cytokine Synthesis." The Journal of Immunology, 2002, 169: 3581-3588.
McLachlin et al., "Retroviral-mediated gene transfer," Progress in Nucleic Acid Research and Molecular Biology, (Editors: Cohn et al.), vol. 38, 1990, pp. 91-135.
Mehal et al., "Antigen presentation by liver cells controls intrahepatic T cell trapping, whereas bone marrow-derived cells preferentially promote intrahepatic T cell apoptosis," The Journal of Immunology, vol. 167, 2001, pp. 667-673.
Mehal et al., "TCR ligation on CD8+ T cells creates double-negative cells in vivo," The Journal of Immunology, vol. 161, 1998, pp. 1686-1693.
Melero et al. "Palettes ofVaccines and Immunostimulatory Monoclonal Antibodies." (Clinical Cancer Research, 2009).
Melero et al., "Amplification of tumor immunity by gene transfer of the co-stimulatory 4-1BB ligand: synergy with the CD28 co-stimulatory pathway," Eur. J. Immunol., vol. 28, 1998, pp. 1116-1121, XP000914703.
Melero et al., "Monoclonal antibodies against the 4-1BB T-cell activation molecule eradicate established tumors," Nature Medicine, vol. 3, No. 6, Jun. 1997, pp. 682-685, XP002104261.
Melero et al., "NK1.1 Cells Express 4-1BB (CDw137) Costimulatory Molecule and Are Required for Tumor Immunity Elicited by Anti-4-1BB Monoclonal Antibodies," Cellular Immunology, vol. 190, Article No. CI981396, 1998, pp. 167-172.
Melief et al., "Strategies for Immunotherapy of Cancer", Advances in Immunology, vol. 75, 2000, pp. 235-282, XP001027072.
Mellman, 2006, The Scientist, vol. 20(1), pp. 47-56.
Merrill et al., "The role of biomarkers in the assessment of lupus", Best Practice & Research Clinical Rheumatology, vol. 19, No. 5, 2005, pp. 709-726.
Merrill, "Emergence of targeted immune therapies for systemic lupus," Expert Opin. Emerging Drugs, vol. 10, No. 1, 2005, pp. 53-65.
Metzler et al., "Solution structure of human CTLA-4 and delineation of a CD80/CD86 binding site conserved in CD28," Nature Structural Biology, vol. 4, No. 7, Jul. 1997, pp. 527-531.
Miller et al., "Gene transfer by retrovirus vectors occurs only in cells that are actively replication at the time of infection," Molecular and Cellular Biology, vol. 10, No. 8, Aug. 1990, pp. 4239-4242.
Miller et al., "Generation of helper-free amphotropic retroviruses that transduce a dominant-acting, methotrexate-resistant dihydrofolate reductase gene," Molecular and Cellular Biology, vol. 5, No. 3, Mar. 1985, pp. 431-437.
Miller et al., "Redesign of retrovirus packaging cell lines to avoid recombination leading to helper virus production," Molecular and Cellular Biology, vol. 6, No. 8, Aug. 1986, pp. 2895-2902.
Miller, "Human gene therapy comes of age," Nature, vol. 357, Jun. 11, 1992, pp. 455-460.
Misquitta et al., "Targeted disruption of gene function in *Drosophila* by RNA interference (RNA-i): A role for nautilus in embryonic somatic muscle formation," Proc. Natl. Acad. Sci. USA, vol. 96, Feb. 1999, pp. 1451-1456.
Mizuhara et al., "T Cell activation-associated hepatic injury: mediation by tumor necrosis factors and protection by interleukin 6", J. Exp. Med., vol. 179, May 1994, pp. 1529-1537.
Mohan et al., "Interaction Between CD40 and Its Ligand gp39 in the Development of Murine Lupus Nephritis," The Journal of Immunology, vol. 154, 1995, pp. 1470-1480.
Montesano et al., "Genetic Alterations in Esophageal Cancer and Their Relevance to Etiology and Pathogenesis: A Review," Int. J. Cancer (Pred. Oncol.), vol. 69, 1996, pp. 225-235.
Morse et al., "Abnormalities Induced by the Mutant Gene Ipr: Expansion of a Unique Lymphocyte Subset," the Journal of Immunology, vol. 129, No. 6, Dec. 1982, pp. 2612-2615.
Moss et al., "Use of vaccinia virus as an infectious molecular cloning and expression vector," Gene Amplification and Analysis, (Editors: Papas et al.), vol. 3, Chapter 10, 1983, pp. 201-213.
Moss, "Poxvirus expression vectors," Current Topics in Microbiology and Immunology, vol. 158, 1992, pp. 25-38.
Moss, "Poxvirus vectors: cytoplasmic expression of transferred genes," Current Opinion in Genetics and Development, vol. 3, 1993, pp. 86-90.
Moss, "Vaccinia virus vectors," Vaccines: New Approaches to Immunological Problems. (Editor: Ellis), Butterworth-Heinemann, Chapter 15, 1992, pp. 345-362.
Moss, "Vaccinia virus: a tool for research and vaccine development," Science, vol. 252, Jun. 21, 1991, pp. 1662-1667.
Motzer et al., Nivolumab versus Everolimus in Advanced Renal-Cell Carcinoma, N. Engl. J. Med., Nov. 5, 2015, 373(19):1803-1813.
Motzer et al., "Renal-Cell Carcinoma," New England Journal of Medicine, vol. 335, No. 12, Sep. 19, 1996, pp. 865-875.
MPSRCH search result, 2008, us-11-245-713.1.rai, result 11, pp. 1-2.
Nabel et al., "Recombinant gene expression in vivo within endothelial cells of the arterial wall," Science, vol. 244, Jun. 16, 1989, pp. 1342-1344.
Nathan and Eisen, "The biological treatment of renal-cell carcinoma and melanoma," The lancet oncology, Feb. 2002, 3(2):89-96.
NCBI Sequence Database Entry. Accession No. AA292201 (Aug. 8, 1997).
NCBI Sequence Database Entry. Accession No. AA823166 (Feb. 17, 1998).
NCBI Sequence Database Entry. Accession No. AA896104 (Apr. 6, 1998).
Nechporuk et al., "The mouse SCA2 gene: DNA sequence, alternative splicing and protein expression," Human Molecular Genetics, vol. 7, No. 8, 1998, pp. 1301-1309.
Needleman et al., "A general method applicable to the Search for similarities in the amino acid sequence of two proteins," J. Mol. Biol., vol. 48, 1970, pp. 443-453.
Nelson et al., "Tumor progression despite efficient tumor antigen cross-presentation and effective "arming" of tumor antigen-specific CTL," Journal of Immunology, vol. 166, 2001, pp. 5557-5566.
Neves et al., "Surgical Treatment of Renal Cancer with Vena Cava Extension," British Journal of Urology, vol. 59, 1987, pp. 390-395.

(56) References Cited

OTHER PUBLICATIONS

Newmark et al., "Preparation and properties of adducts of streptokinase and streptokinase-plasmin complex with polyethylene glycol and pluronic Polyol F38," Journal of Applied Biochemistry, vol. 4, 1982, pp. 185-189.
Ng et al., "Mechanisms of immune evasion by renal cell carcinoma: tumor-induced T-lymphocyte apoptosis and NFκB suppression," Urology, Jan. 2002, 59(1):9-14.
Nicolau et al., "In vivo expression of rat insulin affer intravenous administration of the liposome-entrapped gene for rat insulin 1," Proc. Natl. Acad. Sci. USA, vol. 80, Feb. 1983, pp. 1068-1072.
Nielsen et al., "Melanoma vaccines; the paradox of T cell activation without clinical response," Cancer Chemother. Pharmacol., vol. 46 (Suppl.), 2000, pp. S62-S66.
Nielsen et al., "Peptide nucleic acid (PNA). DNA mimic with a peptide backbone," Bioconjugate Chem., vol. 5, 1994, pp. 3-7.
Nielsen et al., "Sequence-selective recognition of DNA by strand displacement with a thymine-substituted polyamide," Science, vol. 254, Dec. 6, 1991, pp. 1497-1500.
Nishimura et al., "Autoimmune Dilated Cardiomyopathy in PD-1 Receptor-Deficient Mice", Science, vol. 291, Jan. 12, 2001, pp. 319-322.
Nishimura et al., "Development of Lupus-like Antoimune Diseases by Disruption of the PD-1 Gene Encoding an ITIM Motif-Carrying Inmunoreceptor," Immunity, vol. 11, Ang. 1999, pp. 141-151.
Nishimura et al., "Developmentally regulated expression of the PD-1 protein on the surface of double-negative (CD4-CD8) thymocytes, " International Immunol., 8(5):773-780, 1996.
Nishimura et al., "Immunological studies on PD-1-deficient mice: implication of PD-1 as a negative regulator for B cell responses," International Immunology, vol. 10, No. 10, 1998, pp. 1563-1572.
Nisonoff et al., "Separation of univalent fragments from the bivalent rabbit antibody molecule by reduction of disulfide bonds," Archives of Biochemistry and Biophysics, vol. 89, 1960, pp. 230-244.
Nivolumab, Chemocare.com publication, published online, Apr. 2004, 7 pages.
Nomi et al., "Clinical significance and therapeutic potential of the programmed death-1 ligand/programmed death-1 pathway in human pancreatic cancer," Clin Cancer Res., 13(7):2151-2157, Apr. 1, 2007.
Office Action for Australian Application No. 2005295038, dated Feb. 10, 2011, 2 pages.
Office Action for Canadian Application No. 2,583,257, dated Apr. 19, 2012.
Office Action for Canadian Application No. 2,583,257, dated Nov. 15, 2013, 3 pages.
Office Action for Canadian Application No. 2,583,257, dated Sep. 9, 2015, 4 pages.
Office Action for European Application No. 05808659.6, dated Feb. 9, 2016, 4 pages.
Office Action for European Application No. 05808659.6, dated Jul. 2, 2015, 4 pages.
Office Action in European Application No. 05808659.6 dated Aug. 4, 2016, 5 pages.
Office Action issued in Japan in patent application No. 2007-535894 on May 16, 2011, with English translation.
Ohigashi et al. "Clinical significance of programmed death-1 ligand-1 and programmed death-1 ligand-2 expression in human esophageal cancer." Clin Cancer Res. Apr. 15, 2005;11(8):2947-2953.
Okazaki et al., "PD-1 and PD-1 ligands: from discovery to clinical application," International Immunology, vol. 19, No. 7, 2007, pp. 813-824.
Okazaki et al., "PD-1 immunoreceptor inhibits B cell receptormediated signaling by recruiting src homology 2-domain-containing tyrosine phosphatase 2 to phosphotyrosine," PNAS., 98(24):13866-13871, Nov. 20, 2001.
Okudaira et al., "Blockade of B7-HI or B7-DC induces an antitumor effect in a mouse pancreatic cancer model," International Journal of Oncology, vol. 35, No. 4, 2009, pp. 741-749.
Orlandi et al., "Cloning immunoglobulin variable domains for expression by the polymerase chain reaction," Proc. Natl. Acad. Sci. USA, vol. 86, May 1989, pp. 3833-3837.
Ostrov et al., "Structure of Murine CTLA-4 and Its Role in Modulating T Cell Responsiveness," Science, vol. 290, Oct. 27, 2000, pp. 816-819.
Ozkaynak et al., "Programmed death-1 targeting can promote allograft survival," The Journal of Immunology, vol. 169, 2002, pp. 6546-6553, XP002980100.
Pantuck et al., "The Changing Natural History of Renal Cell Carcinoma," The Journal of Urology, vol. 166, Nov. 2001, pp. 1611-1623.
Pardoll, "Spinning molecular immunology into successful immunotherapy," Nature Reviews Immunology, vol. 2, Apr. 2002, pp. 227-238.
Parker et al., "Potential Utility of Uroplakin III, Thrombomodulin, High Molecular Weight Cytokeratin, and Cytokeratin 20 in Noninvasive, Invasive, and Metastatic Urothelial (Transitional Cell) Carcinoma," Am. J. Surg. Pathol., vol. 27, No. 1, 2003, pp. 1-10 (pp. 1-9 provided).
Peach et al., "Both extracellular immunoglobin-like domains of CD80 contain residues critical for binding T cell surface receptors CTLA-4 and CD28," The Journal of Biological Chemistry, vol. 270, No. 36, Sep. 8, 1995, pp. 21181-21187.
Peghini et al., "Immunophaenotyping in the diagnosis of lymphoma," Praxis, vol. 93, No. 41, Oct. 6, 2004, 1687-1692, Abstract only provided.
Penix et al., "Two Essential Regulatory Elements in the Human Interferon.UPSILON. Promoter Confer Activation Specific Expression in T Cells," The Journal of Expirimental Medicine, vol. 178, Nov. 1993, pp. 1483-1496.
Perriman et al., "Effective ribozyme delivery in plant cells," Proc. Natl. Acad. Sci. USA, vol. 92, Jun. 1995, pp. 6175-6179.
Petroff et al., "B7 family molecules: Novel immunomodulators at the maternal-fetal interface," Placenta, vol. 23, Supplement A, Trophoblast Research 16, 2002, pp. S95-S101.
Piccini, "Vaccinia: virus, vector, vaccine," Advances in Vinis Research, (Editors: Maramorosch et al.), vol. 34, 1988, pp. 43-64.
Pilon-Thomas et al., "Blockade of programmed death ligand 1 enhances the therapeutic efficacy of combination immunotherapy against melanoma," J Immunol., 184(7):3442-3449, Epub Mar. 1, 2010.
Pluckthun et al., "Expression of functional antibody Fv and Fab fragments in *Escherichia coli*," Methods in Enzymology, vol. 178, 1989, pp. 497-515.
Poirier et at "Protective immunity evoked by oral administration of attenuated aroA *Salmonella typhimurium* expressing cloned *streptococcal* M protein," Journal of Experimental Medicine, vol. 168, Jul. 1988, pp. 25-32.
Pollok et al., "4-IBB T-cell antigen binds to mature B cells and macrophages, and costimulates anti-.mu.-primed splenic B cells," Eur. J. Immunol., vol. 24, 1994, pp. 367-374.
Pollok et al., "Inducible T Cell Antigen 4-IBB," The Journal of Immunology, vol. 150, No. 3, Feb. 1, 1993, pp. 771-781.
Ponder et al., "Tertiary Templates for Proteins: Use of Packing Criteria in the Enumeration of Allowed Sequences for Different Structural Classes," J. Mol. Biol., vol. 193, 1987, pp. 775-791.
Porter, "The hydrolysis of rabbit UPSILON.-globulin and antibodies with crystalline papain," Biochem J., vol. 73, 1959, pp. 119-126.
Prasad et al., "B7SI, a novel B7 family member that negatively regulates T cell activation," Immunity, vol. 18, Jun. 2003, pp. 863-873.
Prevost-Blondel et al., "Tumor-infiltrating lymphocytes exhibiting high ex vivo cytolytic activity fail to prevent murine melanoma tumor growth in vivo," The Journal of Immunology, vol. 161, 1998, pp. 2187-2194.
Radhakrishnan et al., "Dendritic Cells activated by cross-linking B7-DC (PD-L2) block inflammatory airway disease," J Allergy Clin Inununol, vol. 116, No. 3, 2005, pp. 668-674 (Published online Jun. 17, 2005).
Rajewsky et al., "Genetics, expression, and function of idiotypes," Anu. Rev. Immunol., vol. 1, 1983, pp. 569-607.

(56) References Cited

OTHER PUBLICATIONS

Rathmell et al., "The Central Effectors of Cell Death in the Immune System," Annu. Rev. Immunol., vol. 17, 1999, pp. 781-828.
Razi-Wolf, "Expression and function of the murine B7 antigen, the major costimulatory molecule expressed by peritoneal exudate cells," Proc. Nat. Acad Sci. USA, vol. 89, May 1992, pp. 4210-4214.
Renauld et al., "Expression cloning of the murine and human interleukin 9 receptor cDNAs," Proc. Natl. Acad. Sci. USA, vol. 89, Jun. 1992, pp. 5690-5694.
Ribas et al., "What does PD-L1 positive or negative mean?," J. Exp. Med., Nov. 2016, 213(13):2835-2840.
Riechmann et al., "Reshaping human antibodies for therapy," Nature, vol. 332, Mar. 24, 1988, pp. 323-327.
Ritz et al., "Bioassay Analysis using R," Journal of Statistic Software, vol. 12, Issue 5, Jan. 2005, pp. 1-22.
Rivoltini et al., "Immunity to cancer: attack and escape in T lymphocyte-tumor cell interaction," Immunological Reviews, vol. 188, 2002, pp. 97-113.
Robison-Cox, "Multiple estimation of concentrations in immunoassay using logistic models," Journal of Immunological Methods, vol. 186, 1995, pp. 79-88.
Romano et al., "Quelling: transient inactivation of gene expression in Neurospora crassa by transformation with homologous sequences," Molecular Microbiology, vol. 6, No. 22, 1992, pp. 3343-3353.
Romanos et al. "DNA Cloning 2: Expression Systems: A Practical Approach," IRL Press, Oxford, Chapter 5, 1995, pp. 133-148.
Romero et al., "Ex vivo staining of metastatic lymph nodes by class I major histocompatibility complex tetramers reveals high numbers of antigen-experienced tumor-specific cytolytic T lymphocytes," J. Exp. Med., vol. 188, No. 9, Nov. 2, 1998, pp. 1641-1650.
Rosenberg, "Progress in human tumor immunology and immunotherapy," Nature, vol. 411, May 17, 2001, pp. 380-384.
Rosenfeld et al., "Adenovirus-mediated transfer of a recombinant. alpha.1-antitrypsin gene to the lung epithelium in vivo," Science, vol. 252, Apr. 19, 1991, pp. 431-433.
Rousseaux et al., "Optimal conditions for the preparation of proteolytic fragments from monoclonal IgG of different rat IgG subclasses," Methods in Enzymology, vol. 121, 1986, pp. 663-669.
Russell et al., "Structural Features can be Unconserved in Proteins with Similar Folds," J. Mol. Biol., vol. 244, 1994, pp. 332-350.
Sadoff et al., "Oral *Salmonella typhimurium* vaccine expressing circumsporozoite protein protects against malaria," Science, vol. 240, Apr. 15, 1988, pp. 336-338.
Salama et al., "Critical role of the programmed death-1 (PD-1) pathway in regulation of experimental autoimmune encephalomyelitis," J. Exp. Med., vol. 198, No. 1, Jul. 7, 2003, pp. 71-78.
Salib et al., "Utilization of sodium alginate in drug microencapsulation," Pharmazentische Industrie, 1978, vol. 40, No. 11A, pp. 1230-1234.
Salih et al., "4-1BB ligand—just another costimulating molecule?" International Journal of Clinical Pharmacology and Therapeutics, vol. 40, No. 8, 2002, pp. 348-353.
Salih et al., "The role of leukemia-derived B7-H1 (PD-L1) in tumor-T-cell interactions in humans," Experimental Hematology, 2006, vol. 34, pp. 888-894.
Salomon et at "Complexities of CD28/B7: CTLA-4 costimulatory pathway in autoimmunity and transplantation," Annu. Rev. Immunol., vol. 19, 2001, pp. 225-252.
Samuski et al., "Targeted integration of adeno-associated virus (AAV) into human chromosome 19," The EMBO Journal, vol. 10, No. 12, 1991, pp. 3941-3950.
Sandhu, "Protein Engineering of Antibodies," Critical Reviews in Biotechnology, vol. 12, No. 5/6, 1992, pp. 437-462.
Sanni et al., "Evolution of aminoacyl-tRNA synthetase quaternary structure and activity: *Saccharomyces cerevisiae* mitochondrial phenylalanyl-tRNA synthetase," Proc. Natl. Acad. Sci. USA, vol. 88, Oct. 1991, pp. 8387-8391.
Saudemont and Quesnel, "In a model of tumor dormancy, long-term persistent leukemic cells have increased B7-H1 and B7. 1 expression and resist CTL-mediated lysis," Blood, 104(7):2124-2133, Oct. 2004.
Sawhney et al., "Bioerodible hydrogels based on photopolymerized poly(ethylene glycol)-copoly(.alpha.-hydroxy acid) diacrylate macromers," Macromolecules, vol. 26, No. 4, 1993, pp. 581-587.
Schafer et al., "Induction of a cellular immune response to a foreign antigen by a recombinant Listeria monocytogenes vaccine," J. Immunol., vol. 149, No. 1, Jul. 1, 1992, pp. 53-59.
Schmid et al., "Expression of AMPA Receptor Subunit Flip/Flop Splice Variants in the Rat Auditory Brainstem and Inferior Colliculus," J. Comparative Neurology, vol. 430 No. 2, 2001, pp. 160-171.
Schwartz et al., "Structural Basis for Co-stimulation by the Human CTLA-4/B7•2 Complex," Nature, vol. 410, Mar. 29, 2001, pp. 604-608.
Schwartz et al., "Structural Mechanisms of Costimulation," Nature Immunology, vol. 3, No. 5, May 2002, pp. 427-434.
Schwartz, "Costimulation of T Lymphocytes: The Role of CD28, CTLA-4, and B7/BB1 in Interleukin-2 Production and Immunotherapy," Cell, vol. 71, Dec. 24, 1992, pp. 1065-1068.
Selenko-Gebauer et al., "B7-H1 (Programmed Death-1 Ligand) on Dendritic Cells is Involved in the Induction and Maintenance of T Cell Anergy," J. Immunol., vol. 170, 2003, pp. 3637-3644.
Sequence Alignment, Sequence 3, U.S. Appl. No. 09/644,934, filed Aug. 30, 2001 (now U.S. Pat. No. 6,936,704) of Freeman et al., 2010, 4 pages.
Shaknovich et al., "The Promyelocytic Leukemia Zinc Finger Protein Affects Myeloid Cell Growth, Differentiation, and Apoptosis," Molecular and Cellular Biology, vol. 18, No. 9, Sep. 1998; pp. 5533-5545.
Sharon et al., "Preparation of Fv fragment from the mouse myeloma XRPC-25 immunoglobulin possessing antidinitrophenyl activity," Biochemistry, vol. 15, No. 7, 1976, pp. 1591-1594.
Sheather, "Density Estimation," Statistical Science, vol. 19, No. 4, 2004, pp. 588-597.
Shin et al., "Cooperative B7-1/2 (CD80/CD86) and B7-DC Costimulation of CD4+ T Cells Independent of the PD-1 Receptor," J. Exp. Med., vol. 198, No. 1, Jul. 7, 2003, pp. 31-38.
Sica et al., "B7-H4, a Molecule of the B7 Family, Negatively Regulates T Cell Immunity," Immunity, vol. 18, Jun. 2003, pp. 849-861.
Sica et al., "Biochemical and Immunological Characteristics of 4-1BB (CD137) Receptor and Ligand and Potential Applications in Cancer Therapy," Archivum Immunologiae et Therapiae Experimentalis, vol. 47, 1999, pp. 275-279.
Siddiqui et al., "Tumor-Infiltrating Foxp3-CD4+CD25+ T Cells Predict Poor Survival in Renal Cell Carcinoma," Clin. Cancer Res., vol. 13, No. 7, Apr. 1. 2007, pp. 2075-2081.
Silverman, "Targeting of B cells in SLE: Rationale and Therapeutic Opportunities", Bulletin of the NYU Hospital for Joint Diseases, vol. 64, Nos. 1 and 2, 2006, pp. 51-56.
Simon et al., "B7-H4 is a Novel Membrane-Bound Protein and a Candidate Serum and Tissue Biomarker for Ovarian Cancer," Cancer Res., vol. 66, No. 3, Feb. 1, 2006, pp. 1570-1575.
Singer et al., "Optimal Humanization of 1B4, an Anti-CD18 Murine Monoclonal Antibody, is Achieved by Correct Choice of Human V-Region Framework Sequences," The Journal of Immunology, vol. 150, Apr. 1, 1993, pp. 2844-2857.
Skerra et al., "Assembly of a Functional Immunoglobulin Fv Fragment in *Escherichia coli*," Science, vol. 240, May 20, 1988, pp. 1038-1041.
Skolnick et al., "From genes to protein structure and function: novel applications of computational approaches in the genomic era," Trends in Biotech., vol. 18, No. 1, Jan. 2000, pp. 34-39.
Smith et al., "Pulmonary Deposition and Clearance of Acrosolized Alpha-1-Proteinase Inhibitor Administered to Dogs and to Sheep," J. Clin. Invest., vol. 84, Oct. 1989, pp. 1145-1154.
Smith RT, 1994 (Clin. Inununol, 41(4): 841-849).
Sueller et al., "A Novel Lymphoproliferative/Autoimmune Syndrome Resembling Murine lpr/gld Disease," J. Clin. Invest., vol. 90, Aug. 1992, pp. 334-341.

(56) References Cited

OTHER PUBLICATIONS

Solares et al., "Autoimmune sensorineural hearing loss: an immunologic perspective," Jonmal of Neuroimmunology, vol. 138, 2003, pp. 1-7.
Sorge et al., "Amphotropic Retrovirus Vector System for Human Cell Gene Transfer," Molecular and Cellular Biology, vol. 4, No. 9. Sep. 1984, pp. 1730-1737.
Sonano et al., "Targeted and nontargeted liposomes for in vivo transfer to rat liver cells of a plasmid containing the preproinsulin I gene," Proc. Natl. Acad. Sci. USA, vol. 80, Dec. 1983, pp. 7128-7131.
Stammers et al., "BTL-II: a polymorphic locus with homology to the butyrophilin gene family, located at the border of the major histocompatibility complex class II and class III regions in human and mouse," Immunogenetics, vol. 51, 2000, pp. 373-382.
Stamper et al., "Crystal structure of the B7-1/CTLA-4 complex that inhibits human immune responses," Nature, vol. 410, Mar. 29, 2001, pp. 608-611.
Stanton, P. et al., 1994, Br. J. Cancer, 70: 427-433.
Steinman et al. "Immunotherapy: Bewitched, Bothered, and Bewildered No More." (Science, 305, 197-200, 2004).
Stites et al., "Medical Immunology," 9th Ed., Appleton & Lange, Stamford, Connecticut, 1997, pp. 123 and 635.
Storkel and Berg, "Morphological classification of renal cancer," World J. Urol., 13(3):153-158, Jun. 1995.
Strome et al., "B7-H1 blockade augments adoptive T-cell immunotherapy for squamous cell carcinoma," Cancer Res., 63(19):6501-6505, Oct. 1, 2003.
Strome et al., "Costimulation-based Immunotherapy for Head and Neck Cancer," Curr. Treat Options Oncol., Feb. 2004, 5(1)27-33.
Substantive correspondence to and from USPTO for U.S. Appl. No. 11/245,713, filed Jun. 28, 2007 to Oct. 6, 2010, 157 pages.
Substantive correspondence to and from USPTO for U.S. Appl. No. 13/012,063, filed Apr. 17, 2012 to Jan. 27, 2014, 90 pages.
Substantive correspondence to and from USPTO for U.S. Appl. No. 14/264,568, filed Jun. 29, 2015 to Jun. 1, 2016, 21 pages.
Substantive correspondence to and from USPTO for U.S. Appl. No. 14/842,572, filed Oct. 20, 2016 to Aug. 25, 2020, 110 pages.
Substantive correspondence to and from USPTO for U.S. Appl. No. 15/047,445, from Apr. 5, 2017 to Sep. 20, 2017, 21 pages.
Substantive correspondence to and from USPTO for U.S. Appl. No. 15/069,258, filed Jun. 22, 2017 to Jun. 20, 2018, 32 pages.
Substantive correspondence to and from USPTO for U.S. Appl. No. 15/719,750, filed Apr. 22, 2019 to Oct. 9, 2020, 31 pages.
Substantive correspondence to and from USPTO for U.S. Appl. No. 15/890,048, filed Oct. 10, 2018 to Sep. 5, 2019, 22 pages.
Substantive correspondence to and from USPTO for U.S. Appl. No. 16/544,357, filed Jun. 18, 2020 to Aug. 13, 2021, 32 pages.
Sabudhi et al., "Local expression of B7-H1 promotes organ-specific autoimmunity and transplant rejection," J. Clin. Invest., vol. 113, No. 5, Mar. 2004, pp. 694-700.
Suda et al., "Why do defects in the Fas-Fas ligand system cause autoimmunity?", J. Allergy Clin. Immunol., vol. 100, 1997, pp. S97-S101.
Summerton et al., "Morpholino Antisense Oligomers: Design, Preparation, and Properties," Antisense & Nucleic Acid Drug Development, vol. 7, 1997, pp. 187-195.
Sun et al., "Administration of Agonistic Anti-4-1BB Monoclonal Antibody Leads to the Amelioration of Experimental Autoimmune Encephalomyelitis," The Journal of Immunology, vol. 168, 2002, pp. 1457-1465.
Sun et al., "Costimulatory molecule-targeted antibody therapy of a spontaneous autoimmune disease," Nature Medicine, vol. 8, No. 12, Dec. 2002 (Published online Nov. 11, 2002), pp. 1405-1413.
Sun et al., "Signaling of 4-1BB Leads to Amelioration of Experimental Autoimunune Encephalomyelitis," FASEB J., 2001, 5:A1210, Abstract 950.9.
Sutter et al., "Nonreplicating vaccina vector efficiently expresses recombinant genes," Proc. Natl. Acad. Sci. USA, vol. 89, Nov. 1992, pp. 10847-10851.
Suzuki et al., "T cell-Specific Loss of Pten Leads to Defects in Central and Peripheral Tolerance," Inununity, vol. 14, May 2001, pp. 523-534.
Suzuki et al., "The dual functions of Fas ligand in the regulation of peripheral CD8+ and CD4+ T cells, " Proc. Natl. Acad. Sci. USA, vol. 97, No. 4, Feb. 15, 2000, pp. 1707-1712.
Swallow et al., "B7h, a Novel Costimulatory Homolog of B7.1 and B7.2, Is Induced by TNF.alpha.," Immunity, vol. 11, Oct. 1999, pp. 423-432.
Takahashi et al., "Cutting Edge: 4-1BB is a Bona Fide CD8 T Cell Survival Signal," The Journal of Immunology, vol. 162, No. 9, 1999, pp. 5037-5040.
Takahashi et al., "Expression of B7-H1 in Renal Cell Carcinoma," The Japanese Journal of Urology, 95(2):369, 2004.
Takahashi et al., "Expression of B7-H1 in Renal Cell Carcinoma," Journal of the Japanese Urological Association, Mar. 2004, 2 pages (English translation).
Takeda et al., "Critical contribution of liver natural killer T cells to a murine model of hepatitis," Proc. Natl. Acad. Sci. USA, vol. 97, No. 10, May 9, 2000, pp. 5498-5503.
Tamura et al. "B7-H1 costimulation preferentially enhances CD28-independent T-helper cell function," Blood, vol. 97, No. 6, Mar. 15, 2001, pp. 1809-1816.
Tamura et al., "Immunology of B7-H1 and Its Roles in Human Diseases," Int. J. Hematol., Nov. 2003, 78(4):321-328.
Taube et al., "Association of PD-1, PD-1 ligands, and other features of the tumor immune microenvironment with response to anti-PD-1 therapy," Clin Cancer Res., 20(19):3064-5074, Epub Apr. 8, 2014.
Taylor et al., "Human immunoglobulin transgenes undergo rearrangement, somatic mutation and class switching in mice that lack endogenous IgM," Int. Immunol., vol. 6, No. 4, 1994, pp. 579-591.
Tazi-Ahnini et al., "Cloning, localization, and structure of new members of the butyrophilin gene family in the juxta-telomeric region of the major histocompatibility complex," Immunogenetics, vol. 47, 1997, pp. 55-63.
Temin, "Safety Considerations in Somatic Gene Therapy of Human Disease with Retrovirus Vectors," Human Gene Therapy, vol. 1, 1990, pp. 111-123.
Templeton et al., "Improved DNA: liposome complexes for increased systemic delivery and gene expression," Nature Biotechnology, vol. 15, Jul. 1997, pp. 647-652.
The Japanese Japanese Journal of Urology, vol. 95, p. 369, OP2-076 (Mar. 2004).
Theofilopoulos et al., "Etiopathogenesis of Murine SLE," Immunological Rev,, vol. 55, 1981, pp. 179-216.
Theofilopoulos et al., "Tumour necrosis factor and other cytokines in murine lupus," Ann. Rheum. Dis., vol. 58, Suppl. 1, 1999, pp. 149-155.
Therneau et al. (2000) Modeling Survival Data: Extending the Cox Model, ed. 1 (Springer-Verlag, Ann Arbor), pp. 87-92.
Thompson et al. "B7-H1 glycoprotein blockade; A novel strategy to enhance immunotherapy in patients with renal cell carcinoma." Urology, vol. 66, Issue 5, pp. 10-14.
Thompson et al. "Costimulatory B7-H1 in renal cell carcinoma patients: Indicator of tumor aggressiveness and potential therapeutic target", Proc. Natl. Acad. Sci. USA, vol. 101, pp. 17174-17179 (Dec. 2004).
Thompson et al. "Costimulatory molecule B7-H1 in primary and metastatic clear cell renal cell carcinoma." Cancer. Nov. 15, 2005;104(10):2084-2091.
Thompson et al. "Implications of B7-H1 expression in clear cell carcinoma of the kidney for prognostication and therapy," Clinical Cancer Research Jan. 15, 2007, 13, 709s.
Thompson et al., "cis-Acting Sequences Required for Inducible Interleukin-2 Enhancer Function Bind a Novel Ets-Related Protein, Elf-1," Molecular and Cellular Biology, vol. 12, No. 3, Mar. 1992, pp. 1043-1053.
Thompson et al., "Tumor B7-H1 is Associated with Poor Prognosis in Renal Cell Carcinoma Patients with Long-Term Follow-up," Cancer Res., vol. 66, No. 7, Apr. 1, 2006, pp. 3381-3385.
Tiegs et al., "A T cell-dependent Experimental Liver Injury in Mice Inducible by Concanavalin A," J. Clin. Invest., vol. 90, 1992, pp. 196-203.

(56) References Cited

OTHER PUBLICATIONS

Titomirov et al., "In vivo electroporation and stable transformation of skin cells of newborn mice by plasmid DNA," Biochimica et Biophysica Acta, vol. 1088, 1991, pp. 131-134.
Todd et al., "Transcription of the Interleukin 4 Gene Is Regulated by Multiple Promoter Elements," J. Exp. Med., vol. 177, Jun. 1993, pp. 1663-1674.
Topalian et al., "Safety, Activity, and Immune Correlates of Anti-PD-1 Antibody in Cancer," N. Engl. J. Med., Jun. 28, 2012, 366(26):2443-2454.
Townsend et al., "Tumor Rejection After Direct Costimulation of CD8+ T Cells by B7-Transfected Melanoma Cells, " Science, vol. 259, Jan. 15, 1993, pp. 368-370.
Trabattoni et al., "B7-H1 is up-regulated in HIV infection and is a novel surrogate marker of disease progression," Blood, vol. 101, No. 7, Apr. 1, 2003, pp. 2514-2520.
Tringler et al., "B7-H4 Is Highly Expressed in Ductal and Lobular Breast Cancer," Clinical Cancer Research, vol. 11, Mar. 1, 2005, pp. 1842-1848.
Tseng et al., "B7-DC, a New Dendritic Cell Molecule with Potent Costimulatory Properties for T Cells," J. Exp. Med., vol. 193, No. 7, Apr. 2, 2001, pp. 839-845.
Ueda et al., "Sequence-specific DNA damage induced by reduced mitomycin C and 7-N-(.rho-hydroxyphenyl)mitomycin) C," Nucleic Acids Res., vol. 12, No. 17, 1984, pp. 6673-6683.
Uhlig et al., "Is rheumatoid arthritis disappearing?", Annals of the Rheumatic Diseases, vol. 64, 2005, pp. 7-10.
Verhoeyen et al., "Reshaping Human Antibodies: Grafting an Antilysozyme Activity," Science, vol. 239, 1988, pp. 1534-1536.
Vinay et al., "Role of 4-1BB in immune responses," Seminars in Immunology, vol. 10, No. 6, 1998, pp. 481-489.
Wahl et al., "Improved Radioimaging and Tumor Localization with Monoclonal F(ab')2," J. Nucl. Med., vol. 24, 1983, pp. 316-325.
Walunas et al., "CTLA-4 Ligation Blocks CD28-dependent T Cell Activation," J. Exp. Med., vol. 183, Jun. 1996, pp. 2541-2550.
Wang et al., "Costimulation of T cells by B7-H2, a B7-like molecule that binds ICOS;" Blood, vol. 96, No. 8, Oct. 15, 2000, pp. 2808-2813.
Wang et al., "Ligand Binding Sites of Inducible Costimulator and High Avidity Mutants with Improved Function," J. Exp. Med., vol. 195, No. 8, Apr. 15, 2002, pp. 1033-1041.
Wang et al., "Molecular Modeling and Functional Mapping of B7-H1 and B7-DC: Uncouple Costimulatory Function from PD-1 Interaction," J. Exp. Med., vol. 197, No. 9, May 5, 2003, pp. 1083-1091.
Wang et al., "pH-sensitive immunoliposomes mediate target-cell-specific delivery and controlled expression of a foreign gene in mouse," Proc. Natl. Acad. Sci. USA, vol. 84, Nov. 1987, pp. 7851-7855.
Weiss, "Hot Prospect for New Gene Amplifier: Ligase chain reaction, a combination DNA amplifier and genetic screen could do for DNA diagnostics what PCR has done for basic molecular biology," Science, vol. 254, Nov. 1991, pp. 1292-1293.
Wick et al., "The hepatic Immune System," Critical Reviews in Immunology, vol. 22, No. 1, 2002, pp. 47-103.
Wilcox et al., "B7-H1 (PD-L1, CD274) suppresses host immunity in T-cell lymphoproliferative disorders," Blood, vol. 114, No. 10, Sep. 3, 2009, pp. 2149-2158 (Abstract only).
Wilcox et al., "Provision of antigen and CD137 signaling breaks immunological ignorance, promoting regression of poorly immunogenic tumors," J. Clin. Invest., vol. 109, No. 5, Mar. 2002, pp. 651-659.
Williams et al., "Introduction of foreign genes into tissues of living mice by DNA-coated microprojectiles," Proc. Natl. Proc. Sci. USA, vol. 88, Apr. 1991, pp. 2726-2730.
Williams et al., "Nitric Oxide Synthase Plays a Signaling Role in TCR-Triggered Apoptotic Death," The Journal of Immunology, vol. 161, 1998, pp. 6526-6653.

Williams et al., "The Immunoglobulin Superfamily—Domains for Cell Surface Recognition," Ann. Rev. Immunol., vol. 6, 1988, pp. 381-405.
Winter et al., "Making Antibodies by Phage Display Technology," Ann. Rev. Immunol., vol. 12, 1994, pp. 433-455.
Winter et al., "Man-made antibodies," Nature, vol. 349, Jan. 24, 1991, pp. 293-299.
Wintterle et al., "Expression of the B7-Related Molecule B7-H1 by Glioma Cells: A Potential Mechanism of Immune Paralysis," Cancer Research, vol. 63, Nov. 1, 2003, pp. 7462-7467.
Wofsy et al., "The Proliferating Cells in Autoimmune MRL/lpr Mice Lack L3T4, an Antigen on "Helper" T Cells that Is Involved in the Response to Class II Major Histocompatibility Antigens," The Journal of Immunology, vol. 132, No. 6, Jun. 1984, pp. 2686-2689.
Wofsy, "Treatment of Murine Lupus with Anti-CD4 Monoclonal Antibodies," Immunol. Ser., vol. 59, 1993, pp. 221-236.
Wolff et al., "Direct Gene Transfer into Mouse Muscle in Vivo," Science, vol. 247, Mar. 23, 1990, pp. 1465-1468.
Wong et al., "Human GM-CSF: Molecular Cloning of the Complementary DNA and Purification of the Natural and Recombinant Proteins," Science, vol. 228, May 17, 1985, pp. 810-815.
Wu et al. "Kupffer Cell Suppression of CD8+ T Cells in Human Hepatocellular Carcinoma is Mediated by B7-H1/Programmed Death-1 Interactions," Cancer Res., vol. 69, No. 20, Oct. 15, 2009, pp. 8067-8075.
Wu et al., "Receptor-mediated Gene Delivery and Expression in Vivo," The Journal of Biological Chemistry, vol. 263, No. 29, Oct. 1988, pp. 14621-14624.
Wu et al., "Targeting Genes: Delivery and Persistent Expression of a Foreign Gene Driven by Mammalian Regulatory Elements in Vivo," The Journal of Biological Chemistry, vol. 264, Oct. 1989, pp. 16985-16987.
Yamazaki et al., "Expression of Programmed Death 1 Ligands by Murine T Cells and APC," The Journal of Immunology, vol. 169, 2002, pp. 5538-5545.
Yang et al., "In Vitro Priming of Tumor-Reactive Cytolytic T Lymphocytes by Combining IL-10 with B7-CD28 Costimulation," The Journal of Immunology, vol. 155, 1995, pp. 3897-3903.
Yang et al., "In vivo and in vitro gene transfer to mammalian somatic cells by particle bombardment," Proc. Natl. Acad. Sci. USA, vol. 87, Dec. 1990, pp. 9568-9572.
Yang, "Gene Transfer into Mammalian Somatic Cells In Vivo," Critical Reviews in Biotechnology, vol. 12, No. 4, 1992, pp. 335-356.
Yoshinaga et al., "T-cell co-stimulation through B7RP-I and ICOS," Nature, vol. 402, Dec. 16, 1999, pp. 827-832.
Youngnak et al., "Differential binding properties of B7-HI and B7-DC to programmed death-1," Biochemical and Biophysical Research Commununications, vol. 307, No. 3, 2003, pp. 672-677.
Zang et al., "B7x: A widely expressed B7 family member that inhibits T cell activation," Proc. Natl. Acad. Sci. USA, vol. 100, No. 18, Sep. 2, 2003, pp. 10388-10392.
Zelenin et al., "Genetic transformation of mouse cultured cells with the help of high-velocity mechanical DNA injection," FEBS Lett., vol. 244, No. 1, Feb. 1989, pp. 65-67.
Zelenin et al., "High velocity mechanical DNA transfer of the chloramphenicolacetyl transferase gene into rodent liver, kidney and mammary gland cells in organ explants and in vivo," FEBS Lett., vol. 280, No. 1, Mar. 1991, pp. 94-96.
Zha et al., "Negative regulation of T-cell function by PD-1," Critical Reviews™ in Immunology, 24(4):229-237, 2004.
Zhang et al., "B7-H1-targeted immunotherapy for head and neck cancer." Expert Opinion on Biological Therapy Oct. 2004, vol. 4, No. 10 : pp. 1577-1583.
Zhang et al., "The expression of PD-1 ligands and their involvement in regulation of T cell functions in acute and chronic woodchuck hepatitis virus infection," PLoS One, 6(10):e26196, Epub Oct. 14, 2011.
Zhou et al., "Inducible-costimulator-mediated suppression of human immunodeficiency virus type 1 replication in CD4+ T lymphocytes," Virology, vol. 325, No. 2, 2004, pp. 252-263.
Zips et al., 2005, In vivo, vol. 19, pp. 1-8.

(56) References Cited

OTHER PUBLICATIONS

Zumla et al., "Granulomatous Infections: Etiology and Classification," Clinical Infectious Diseases, vol. 23, 1996, pp. 146-158.
Zwiebel et al., "Drug Delivery by Genetically Engineered Cell Implants," Ann. N.Y. Acad Sci., vol. 618. 1991, pp. 394-404.
U.S. Appl. No. 11/245,713, filed Oct. 6, 2005, Lieping Chen.
U.S. Appl. No. 13/012,063, filed Jan. 24, 2011, Lieping Chen.
U.S. Appl. No. 14/264,568, filed Apr. 29, 2014, Lieping Chen.
U.S. Appl. No. 14/842,572, filed Sep. 1, 2015, Lieping Chen.
U.S. Appl. No. 15/047,445, filed Feb. 18, 2016, Lieping Chen.
U.S. Appl. No. 15/069,258, filed Mar. 14, 2016, Lieping Chen.
U.S. Appl. No. 15/719,750, filed Sep. 29, 2017, Lieping Chen.
U.S. Appl. No. 15/890,048, filed Feb. 6, 2018, Lieping Chen.
U.S. Appl. No. 16/544,357, filed Aug. 19, 2019, Lieping Chen.

FIG. 3

MRIFAVFIFMTYWHLLNAFTVTVPKDLYVVEYGSNMTIECKFPVEKQLDLAALIV
YWEMEDKNIIQFVHGEEDLKVQHSSYRQRARLLKDQLSLGNAALQITDVKLQD
AGVYRCMISYGGADYKRITVKVNAPYNKINQRILVVDPVTSEHELTCQAEGYPK
AEVIWTSSDHQVLSGKTTTTNSKREEKLFNVTSTLRINTTTNEIFYCTFRRLDPEE
NHTAELVIPELPLAHPPNERTHLVILGAILLCLGVALTFIFRLRKGRMMDVKKCGI
QDTNSKKQSDTHLEET

FIG. 4

ATGAGGATATTTGCTGTCTTTATATTCATGACCTACTGGCATTTGCTGAACGC
ATTTACTGTCACGGTTCCCAAGGACCTATATGTGGTAGAGTATGGTAGCAATA
TGACAATTGAATGCAAATTCCCAGTAGAAAAACAATTAGACCTGGCTGCACT
AATTGTCTATTGGGAAATGGAGGATAAGAACATTATTCAATTTGTGCATGGA
GAGGAAGACCTGAAGGTTCAGCATAGTAGCTACAGACAGAGGGCCCGGCTG
TTGAAGGACCAGCTCTCCCTGGGAAATGCTGCACTTCAGATCACAGATGTGA
AATTGCAGGATGCAGGGGTGTACCGCTGCATGATCAGCTATGGTGGTGCCGA
CTACAAGCGAATTACTGTGAAAGTCAATGCCCCATACAACAAAATCAACCAA
AGAATTTTGGTTGTGGATCCAGTCACCTCTGAACATGAACTGACATGTCAGGC
TGAGGGCTACCCCAAGGCCGAAGTCATCTGGACAAGCAGTGACCATCAAGTC
CTGAGTGGTAAGACCACCACCACCAATTCAAGAGAGGAGAAGCTTTTCA
ATGTGACCAGCACACTGAGAATCAACACAACAACTAATGAGATTTTCTACTG
CACTTTTAGGAGATTAGATCCTGAGGAAAACCATACAGCTGAATTGGTCATC
CCAGAACTACCTCTGGCACATCCTCCAAATGAAAGGACTCACTTGGTAATTCT
GGGAGCCATCTTATTATGCCTTGGTGTAGCACTGACATTCATCTTCCGTTTAA
GAAAAGGGAGAATGATGGATGTGAAAAATGTGGCATCCAAGATACAAACT
CAAAGAAGCAAAGTGATACACATTTGGAGGAGACG

FIG. 5

MRIFAGIIFTACCHLLRAFTITAPKDLYVVEYGSNVTMECRFPVERELDLLALVV
YWEKEDEQVIQFVAGEEDLKPQHSNFRGRASLPKDQLLKGNAALQITDVKLQDA
GVYCCIISYGGADYKRITLKVNAPYRKINQRISVDPATSEHELICQAEGYPEAEVI
WTNSDHQPVSGKRSVTTSRTEGMLLNVTSSLRVNATANDVFYCTFWRSQPGQN
HTAELIIPELPATHPPQNRTHWVLLGSILLFLIVVSTVLLFLRKQVRMLDVEKCGV
EDTSSKNRNDTQFEET

FIG. 6

ATGAGGATATTTGCTGGCATTATATTCACAGCCTGCTGTCACTTGCTACGGGC
GTTTACTATCACGGCTCCAAAGGACTTGTACGTGGTGGAGTATGGCAGCAAC
GTCACGATGGAGTGCAGATTCCCTGTAGAACGGGAGCTGGACCTGCTTGCGT
TAGTGGTGTACTGGGAAAAGGAAGATGAGCAAGTGATTCAGTTTGTGGCAGG
AGAGGAGGACCTTAAGCCTCAGCACAGCAACTTCAGGGGGAGAGCCTCGCT
GCCAAAGGACCAGCTTTTGAAGGGAAATGCTGCCCTTCAGATCACAGACGTC
AAGCTGCAGGACGCAGGCGTTTACTGCTGCATAATCAGCTACGGTGGTGCGG
ACTACAAGCGAATCACGCTGAAAGTCAATGCCCCATACCGCAAAATCAACCA
GAGAATTTCCGTGGATCCAGCCACTTCTGAGCATGAACTAATATGTCAGGCC
GAGGGTTATCCAGAAGCTGAGGTAATCTGGACAAACAGTGACCACCAACCCG
TGAGTGGGAAGAGAAGTGTCACCACTTCCCGGACAGAGGGGATGCTTCTCAA
TGTGACCAGCAGTCTGAGGGTCAACGCCACAGCGAATGATGTTTTCTACTGT
ACGTTTTGGAGATCACAGCCAGGGCAAAACCACACAGCGGAGCTGATCATCC
CAGAACTGCCTGCAACACATCCTCCACAGAACAGGACTCACTGGGTGCTTCT
GGGATCCATCCTGTTGTTCCTCATTGTAGTGTCCACGGTCCTCCTCTTCTTGAG
AAAACAAGTGAGAATGCTAGATGTGGAGAAATGTGGCGTTGAAGATACAAG
CTCAAAAAACCGAAATGATACACAATTCGAGGAGACG

SEQUENCE LISTING

<160> NUMBER OF SEQ ID NOS: 4

<210> SEQ ID NO 1
<211> LENGTH: 290
<212> TYPE: PRT
<213> ORGANISM: Homo sapiens

<400> SEQUENCE: 1

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160
```

```
Pro Lys Ala Glu Val Ile Trp Thr Ser Ser Asp His Gln Val Leu Ser
                165                 170                 175
Gly Lys Thr Thr Thr Thr Asn Ser Lys Arg Glu Glu Lys Leu Phe Asn
            180                 185                 190
Val Thr Ser Thr Leu Arg Ile Asn Thr Thr Thr Asn Glu Ile Phe Tyr
        195                 200                 205
Cys Thr Phe Arg Arg Leu Asp Pro Glu Glu Asn His Thr Ala Glu Leu
    210                 215                 220
Val Ile Pro Glu Leu Pro Leu Ala His Pro Pro Asn Glu Arg Thr His
225                 230                 235                 240
Leu Val Ile Leu Gly Ala Ile Leu Leu Cys Leu Gly Val Ala Leu Thr
                245                 250                 255
Phe Ile Phe Arg Leu Arg Lys Gly Arg Met Met Asp Val Lys Lys Cys
                260                 265                 270
Gly Ile Gln Asp Thr Asn Ser Lys Lys Gln Ser Asp Thr His Leu Glu
            275                 280                 285
Glu Thr
    290

<210> SEQ ID NO 2
<211> LENGTH: 870
<212> TYPE: DNA
<213> ORGANISM: Homo sapiens

<400> SEQUENCE: 2
atgaggatat tgctgtctt tatattcatg acctactggc atttgctgaa cgcatttact      60
gtcacggttc ccaaggacct atatgtggta gagtatggta gcaatatgac aattgaatgc    120
aaattcccag tagaaaaaca attagacctg gctgcactaa ttgtctattg ggaaatggag    180
gataagaaca ttattcaatt tgtgcatgga gaggaagacc tgaaggttca gcatagtagc    240
tacagacaga gggcccggct gttgaaggac cagctctccc tgggaaatgc tgcacttcag    300
atcacagatg tgaaattgca ggatgcaggg gtgtaccgct gcatgatcag ctatggtggt    360
gccgactaca agcgaattac tgtgaaagtc aatgccccat acaacaaaat caaccaaaga    420
atttttggttg tggatccagt cacctctgaa catgaactga catgtcaggc tgagggctac    480
cccaaggccg aagtcatctg acaagcagt gaccatcaag tcctgagtgg taagaccacc    540
accaccaatt ccaagagaga ggagaagctt ttcaatgtga ccagcacact gagaatcaac    600
acaacaacta atgagatttt ctactgcact tttaggagat tagatcctga ggaaaaccat    660
acagctgaat tggtcatccc agaactacct ctggcacatc ctccaaatga aggactcac    720
ttggtaattc tgggagccat cttattatgc cttggtgtag cactgacatt catcttccgt    780
ttaagaaaag ggagaatgat ggatgtgaaa aatgtggca tccaagatac aaactcaaag    840
aagcaaagtg atacacattt ggaggagacg                                      870

<210> SEQ ID NO 3
<211> LENGTH: 290
<212> TYPE: PRT
<213> ORGANISM: Mus musculus

<400> SEQUENCE: 3

Met Arg Ile Phe Ala Gly Ile Ile Phe Thr Ala Cys Cys His Leu Leu
1               5                   10                  15
Arg Ala Phe Thr Ile Thr Ala Pro Lys Asp Leu Tyr Val Val Glu Tyr
                20                  25                  30
```

Gly Ser Asn Val Thr Met Glu Cys Arg Phe Pro Val Glu Arg Glu Leu
            35                  40                  45

Asp Leu Leu Ala Leu Val Val Tyr Trp Glu Lys Glu Asp Glu Gln Val
 50                  55                  60

Ile Gln Phe Val Ala Gly Glu Glu Asp Leu Lys Pro Gln His Ser Asn
 65                  70                  75                  80

Phe Arg Gly Arg Ala Ser Leu Pro Lys Asp Gln Leu Leu Lys Gly Asn
                 85                  90                  95

Ala Ala Leu Gln Ile Thr Asp Val Lys Leu Gln Asp Ala Gly Val Tyr
            100                 105                 110

Cys Cys Ile Ile Ser Tyr Gly Gly Ala Asp Tyr Lys Arg Ile Thr Leu
            115                 120                 125

Lys Val Asn Ala Pro Tyr Arg Lys Ile Asn Gln Arg Ile Ser Val Asp
            130                 135                 140

Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
                165                 170                 175

Lys Arg Ser Val Thr Thr Ser Arg Thr Glu Gly Met Leu Leu Asn Val
            180                 185                 190

Thr Ser Ser Leu Arg Val Asn Ala Thr Ala Asn Asp Val Phe Tyr Cys
            195                 200                 205

Thr Phe Trp Arg Ser Gln Pro Gly Gln Asn His Thr Ala Glu Leu Ile
            210                 215                 220

Ile Pro Glu Leu Pro Ala Thr His Pro Pro Gln Asn Arg Thr His Trp
225                 230                 235                 240

Val Leu Leu Gly Ser Ile Leu Leu Phe Leu Ile Val Val Ser Thr Val
                245                 250                 255

Leu Leu Phe Leu Arg Lys Gln Val Arg Met Leu Asp Val Glu Lys Cys
            260                 265                 270

Gly Val Glu Asp Thr Ser Ser Lys Asn Arg Asn Asp Thr Gln Phe Glu
            275                 280                 285

Glu Thr
    290

<210> SEQ ID NO 4
<211> LENGTH: 870
<212> TYPE: DNA
<213> ORGANISM: Mus musculus

<400> SEQUENCE: 4
atgaggatat tgctggcat tatattcaca gcctgctgtc acttgctacg ggcgtttact      60
atcacggctc caaggactt gtacgtggtg gagtatggca gcaacgtcac gatggagtgc     120
agattccctg tagaacggga gctggacctg cttgcgttag tggtgtactg ggaaaaggaa     180
gatgagcaag tgattcagtt tgtggcagga gaggaggacc ttaagcctca gcacagcaac     240
ttcaggggga gagcctcgct gccaaaggac cagctttga agggaaatgc tgcccttcag     300
atcacagacg tcaagctgca ggacgcaggc gtttactgct gcataatcag ctacggtggt     360
gcggactaca gcgaatcac gctgaaagtc aatgccccat accgcaaaat caaccagaga     420
atttccgtgg atccagccac ttctgagcat gaactaatat gtcaggccga gggttatcca     480
gaagctgagg taatctggac aaacagtgac caccaacccg tgagtgggaa gagaagtgtc     540
accacttccc ggacagaggg gatgcttctc aatgtgacca gcagtctgag ggtcaacgcc     600

-continued

```
acagcgaatg atgttttcta ctgtacgttt tggagatcac agccagggca aaaccacaca    660
gcggagctga tcatcccaga actgcctgca acacatcctc cacagaacag gactcactgg    720
gtgcttctgg gatccatcct gttgttcctc attgtagtgt ccacggtcct cctcttcttg    780
agaaaacaag tgagaatgct agatgtggag aaatgtggcg ttgaagatac aagctcaaaa    840
aaccgaaatg atacacaatt cgaggagacg                                     870
```

COSTIMULATORY B7-H1 IN RENAL CELL CARCINOMA PATIENTS: INDICATOR OF TUMOR AGGRESSIVENESS AND POTENTIAL THERAPEUTIC TARGET

CROSS-REFERENCE TO RELATED APPLICATIONS

This application is a Continuation of U.S. patent application Ser. No. 16/544,357, filed on Aug. 19, 2019 (now U.S. Pat. No. 11,242,387), which is a Continuation of U.S. patent application Ser. No. 15/890,048, filed Feb. 6, 2018 (Abandoned), which is a Continuation of U.S. patent application Ser. No. 15/069,258, filed Mar. 14, 2016 (Abandoned), which is a Continuation of U.S. patent application Ser. No. 14/264,568, filed Apr. 29, 2014 (Abandoned), which is a Continuation of U.S. patent application Ser. No. 13/012,063 (now U.S. Pat. No. 8,747,833), filed Jan. 24, 2011, which is a Continuation of U.S. patent application Ser. No. 11/245,713 (now U.S. Pat. No. 7,892,540), filed Oct. 6, 2005, which claims the benefit of U.S. Provisional Application 60/642,794, filed Jan. 11, 2005, and U.S. Provisional Application No. 60/616,590, filed Oct. 6, 2004. The disclosures of all prior applications are expressly incorporated herein by reference in their entirety.

TECHNICAL FIELD

This invention relates to immune molecules expressed in cancer tissue, and more particularly to evaluating the expression of immune molecules in tumor cells and tumor-infiltrating leukocytes.

BACKGROUND

An important determinant for the initiation and progression of cancer is the ability of cancer cells to evade the host's immune system. The presence in cancer tissue of, for example, inadequate, inappropriate, or inhibitory immune molecules can restrict the host's ability to generate immune responses to the cancer.

The disclosures of U.S. Pat. No. 6,803,192 and co-pending U.S. application Ser. Nos. 09/649,108; 10/127,282; and Ser. No. 10/719,477; and International Application No. US/02/32364 are incorporated herein by reference in their entirety.

SUMMARY

The invention is based in part on the finding that in renal cell carcinoma (RCC) patients the risk of death is proportional to the number of tumor cells, and/or leukocytes in the tumor, expressing the co-stimulatory human glycoprotein B7-H1. As used herein, the term "B7-H1" refers to B7-H1 from any mammalian species and the term "hB7-H1" refers to human B7-H1. Further details on B7-H1 polypeptides and nucleic acids are provided in U.S. Pat. No. 6,803,192 and co-pending U.S. application Ser. No. 09/649,108, the disclosures of which are incorporated herein by reference in their entirety.

The invention provides methods of diagnosing subjects having, or that are likely to develop, cancer of a tissue based on the expression of B7-H1 by cells of the cancer tissue, methods of predicting success of immunotherapy, methods of prognosis, and methods of treatment. Leukocytes in a tumor are sometimes referred to herein as "tumor-infiltrating leukocytes" or "leukocytes infiltrating a/the tumor."

More specifically, the invention provides a method of diagnosis of cancer in a subject. The method involves: (a) providing a tissue sample from a subject suspected of having, or likely to develop, cancer of the tissue, wherein the sample contains test cells, the test cells being cells of the tissue or leukocytes infiltrating the tissue; and (b) assessing whether the test cells express B7-H1, wherein expression by some or all of the test cells is an indication that the subject has cancer.

The assessment of B7-H1 expression can be performed by the detection of B7-H1 polypeptide or mRNA. B7-H1 polypeptide can be detected, for example, by contacting the tissue sample, or test cells contained in the tissue sample, with an antibody that binds to the B7-H1 polypeptide. Suitable methods for detection of B7-H1 polypeptide can include, without limitation, fluorescence flow cytometry (FFC) or immunohistology. B7-H1 mRNA can be detected, for example, by contacting the tissue sample with a nucleic acid probe that hybridizes to the B7-H1 mRNA (e.g., such by in situ hybridization) or by reverse transcriptase-polymerase chain reaction. The tissue can be tissue of any organ or anatomical system, and can include, without limitation, lung, epithelial, connective, vascular, muscle, neural, skeletal, lymphatic, prostate, cervical, breast, spleen, gastric, intestinal, oral, esophageal, uterine, ovarian, or testicular tissue. The tissue can also be renal tissue. The subject can be a mammal, such as, for example, a human.

Another aspect of the invention is a method of identifying a candidate for immunotherapy. This method involves: (a) providing a tissue sample from a subject with cancer of the tissue, wherein the tissue sample contains test cells, the test cells being cancer cells or tumor-infiltrating leukocytes; and (b) assessing the level of test cells in the tissue sample that express B7-H1, wherein, if B7-H1 expression is not detected in the test cells or if less than an immuno-inhibitory threshold level of the test cells express B7-H1, the subject is more likely to benefit from immunotherapy.

The level of B7-H1 can be assessed by detecting B7-H1 polypeptide or mRNA using, for example, any of the methods described above for method of diagnosis. The tissue can be tissue of any organ or anatomical system, and can include, without limitation, lung, epithelial, connective, vascular, muscle, neural, skeletal, lymphatic, prostate, cervical, breast, spleen, gastric, intestinal, oral, esophageal, uterine, ovarian, or testicular tissue. The tissue can also be renal tissue. The subject can be a mammal, such as, for example, a human. The cancer can be any cancer, and includes, for example, renal cell carcinoma.

In another embodiment, the invention features a method of determining the prognosis of a subject with cancer. This method involves: (a) providing a tissue sample from a subject with cancer of the tissue, wherein the tissue sample comprises test cells, the test cells being cancer cells or tumor-infiltrating leukocytes; and (b) assessing the level of test cells in the tissue sample that express B7-H1, wherein, if a prognostic level, or more than a prognostic level, of the test cells express B7-H1, the subject is more likely to die of the cancer than if less than a prognostic level of the test cells express B7-H1. The prognostic level is a predetermined value obtained by performing statistical clinical analyses known in the art, e.g., those described herein. The assessment of B7-H1 can be performed by detecting B7-H1 polypeptide or B7-H1 mRNA using any of a variety of methods known in the art, including, for example, those listed above for methods of diagnosis and method of immunotherapy. The tissue sample can be of any tissue, and can include, for example, any of those described above. The subject from which the tissue is provided can be a mammal, e.g., a human.

Yet another aspect of the invention is a method of treatment. The method involves: (a) identifying a subject with cancer, wherein some or all cells of the cancer or some or all tumor-infiltrating leukocytes of the cancer express B7-H1; and (b) delivering to the subject an agent that interferes with an interaction between B7-H1 and a receptor for B7-H1. The agent can bind to B7-H1 or to a receptor for B7-H1, e.g., the PD-1 receptor. The agent can be an antibody or an antibody fragment (e.g., Fab', F(ab')$_2$, or single chain Fv (scFv) fragment) that binds to B7-H1 or binds to a receptor for B7-H1; soluble B7-H1 or a soluble functional fragment of B7-H1; a soluble receptor for B7-H1 or a soluble functional fragment thereof. Whenever it is desired, the agent can be administered before, simultaneous with, or after administration of one or more immunomodulatory cytokines, growth factors, or antiangiogenic factors. Examples of such immunomodulatory cytokines, growth factors, and antiangiogenic factors include, without limitation, any of interleukins (IL)-1 to 25, interferon-γ (IFN-γ), interferon-α (IFN-α), interferon-β (IFN-β), interferon-γ (IFN-γ), tumor necrosis factor-α (TNF-α), granulocyte macrophage colony stimulating factor (GM-CSF), granulocyte macrophage colony stimulating factor (G-CSF), endostatin, angiostatin, and thrombospondin. Administrations of the agent and/or the one or more immunomodulatory cytokines, growth factors, or antiangiogenic factors can be systemic (e.g., intravenous) or local, e.g., during surgery by direct injection or infusion into the tissue that comprises the cells of the cancer and/or tumor-infiltrating leukocytes. The cancer can be, without limitation, hematological cancer, neurological cancer, melanoma, breast cancer, lung cancer, head and neck cancer, gastrointestinal cancer, liver cancer, pancreatic cancer, renal cancer, genitourinary cancer, bone cancer, or vascular cancer.

Yet another aspect of the invention is a method of inhibiting the expression of B7-H1 in a tumor cell or a tumor-infiltrating leukocyte. The method involves: (a) identifying a subject with cancer, the cancer containing a target cell that expresses B7-H1, the target cell being a tumor cell or a tumor-infiltrating leukocyte; and (b) introducing into the target cell: (i) an antisense oligonucleotide that hybridizes to a B7-H1 transcript, wherein the antisense oligonucleotide inhibits the expression of B7-H1 in the cell; or (ii) a B7-H1 interference RNA (RNAi). The introducing step can involve administration of the antisense oligonucleotide or the RNAi to the subject and uptake of the oligonucleotide or the RNAi by the target cell. Alternatively, the introducing step can involve administering to the subject, and uptake by the cell of, a nucleic acid comprising a transcriptional regulatory element (TRE) operably linked to a nucleotide sequence complementary to the antisense oligonucleotide, wherein transcription of the nucleotide sequence inside the cell produces the antisense oligonucleotide. Moreover, the introducing step can include administering to the subject, and uptake by the cell of, a nucleic acid: (a) from which sense and anti-sense strands of the RNAi can be transcribed wider the direction of the TREs; or (b) from which both sense and anti-sense strands of the RNAi can be transcribed under the direction of a single TRE.

The tissue sample can be lung, epithelial, connective, vascular, muscle, skeletal, lymphatic, prostate, cervical, breast, spleen, gastric, intestinal, oral, esophageal, dermal, liver, bladder, thyroid, thymic, adrenal, brain, gallbladder, pancreatic, uterine, ovarian, or testicular tissue. The tissue can also be renal tissue. The cancer of the tissue can be any cancer and includes, e.g., renal cell carcinoma.

The subject can be a mammal and includes, for example, a human, a non-human primate (e.g., a monkey), a horse, a cow (or an ox or bull), a pig, a sheep, a goat, a cat, a rabbit, a guinea pig, a hamster, a rat, or a gerbil.

As used herein, "interferes with an interaction between B7-H1 and a receptor for B7-H1" means (a) completely blocks a physical interaction between B7-H1 molecule and a receptor for B7-H1 such that there is substantially no physical interaction between the B7-H1 molecule and the receptor, or (b) modifies the interaction between the B7-H1 molecule and the receptor such that the physical interaction either does not deliver a signal to the cell that comprises B7-H1, and/or the receptor for B7-H1, or delivers a signal that does not substantially affect the antitumoral activity of the cell.

"Polypeptide" and "protein" are used interchangeably and mean any peptide-linked chain of amino acids, regardless of length or post-translational modification. Polypeptides useful for the invention include variant polypeptides that are identical to corresponding wild-type polypeptides but differ by not more than 50 (e.g., not more than: 45; 40; 35; 30; 25; 20; 19; 18; 17; 16; 15; 14; 13; 12; 11; 10; nine; eight; seven; six; five; four; three; two; or one) conservative substitution(s). All that is required is that the variant polypeptide has at least 20% (e.g., at least: 25; 30%; 35%; 40%; 45%; 50%; 60%; 70%; 80%; 85%; 90%; 93%; 95%; 96%; 97%; 98%; 99%; 99.5%; 99.8%; 99.9%; or 100% or more) of the activity of the wild-type polypeptide. Conservative substitutions typically include substitutions within the following groups: glycine and alanine; valine, isoleucine, and leucine; aspartic acid and glutamic acid; asparagine, glutamine, serine, and threonine; lysine, histidine, and arginine; and phenylalanine and tyrosine.

As used herein, "tumor-infiltrating leukocytes" can be T lymphocytes (such as CD8$^+$ T lymphocytes and/or CD4$^+$ T lymphocytes), B lymphocytes, or other bone marrow-lineage cells including granulocytes (neutrophils, eosinophils, basophils), monocytes, macrophages, dendritic cells (i.e., interdigitating dentritic cells), histiocytes, and natural killer cells.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

Other features and advantages of the invention will be apparent from the following description, from the drawings and from the claims.

DESCRIPTION OF DRAWINGS

FIG. 2A shows the association of tumor hB7-H1 expression with death from RCC (risk ratio 2.91; 95% CI [Confidence Interval] 1.39-6.13; p=0.005). The cancer-specific survival rates (with standard error [SE] and number still at risk indicated in parentheses) at 1, 2 and 3 years following nephrectomy were: 87.8% (4.1%, 53), 72.3% (6.0%, 30), and 63.2% (7.2%, 11), respectively, for patients with specimens that had >10% tumor hB7-H1 expression; compared with 93.6% (2.3%, 95), 88.4% (3.4%, 48), and 88.4% (3.4%, 19), respectively, for patients with specimens that had <10% tumor hB7-H1 expression.

FIG. 2B shows the association of adjusted score for leukocyte hB7-H1 expression with death from RCC (risk ratio 3.58; 95% CI 1.74-7.37; p<0.001). The cancer-specific survival rates (SE, number still at risk) at 1, 2, and 3 years were: 83.5% (6.2%, 26), 63.9% (9.2%, 13), and 53.6% (10.2%, 5), respectively, for patients with specimens that had a leukocyte hB7-H1 expression score ≥100; compared with 93.5% (2.1%, 122), 86.2% (3.3%, 65), and 84.8% (3.5%, 25), respectively, for patients with specimens that had scores <100.

FIG. 2C shows the association of high aggregate intratumoral hB7-H1 expression with death from RCC (risk ratio 4.53; 95% CI 1.94-10.56; p<0.001). The cancer-specific survival rates (SB, number still at risk) at 1, 2, and 3 years were: 87.0%(3.8%, 61), 70.0% (5.8%, 32), and 61.9% (6.8%, 13), respectively, for patients with specimens that had high aggregate intratumoral hB7-H1 expression; compared with 94.9%(2.2%, 87), 91.9%(3.1%, 46), and 91.9% (3.1%, 17), respectively, for patients with specimens that had both <10% tumor and <100 leukocyte (low aggregate intratumoral expression) hB7-H1 expression.

FIG. 3 is a depiction of the amino acid sequence (SEQ ID NO:1) of full-length, immature hB7-H1, i.e., hB7-H1 including a leader peptide of about 22 amino acids.

FIG. 4 is a depiction of the nucleotide sequence (SEQ ID NO:2) of cDNA encoding full-length, immature hB7-H1.

FIG. 5 is a depiction of the amino acid sequence (SEQ ID NO:3) of full-length, immature murine B7-H1.

FIG. 6 is a depiction of the nucleotide sequence (SEQ ID NO:4) of cDNA encoding full-length, immature murine B7-H1.

DETAILED DESCRIPTION

Figure 1:
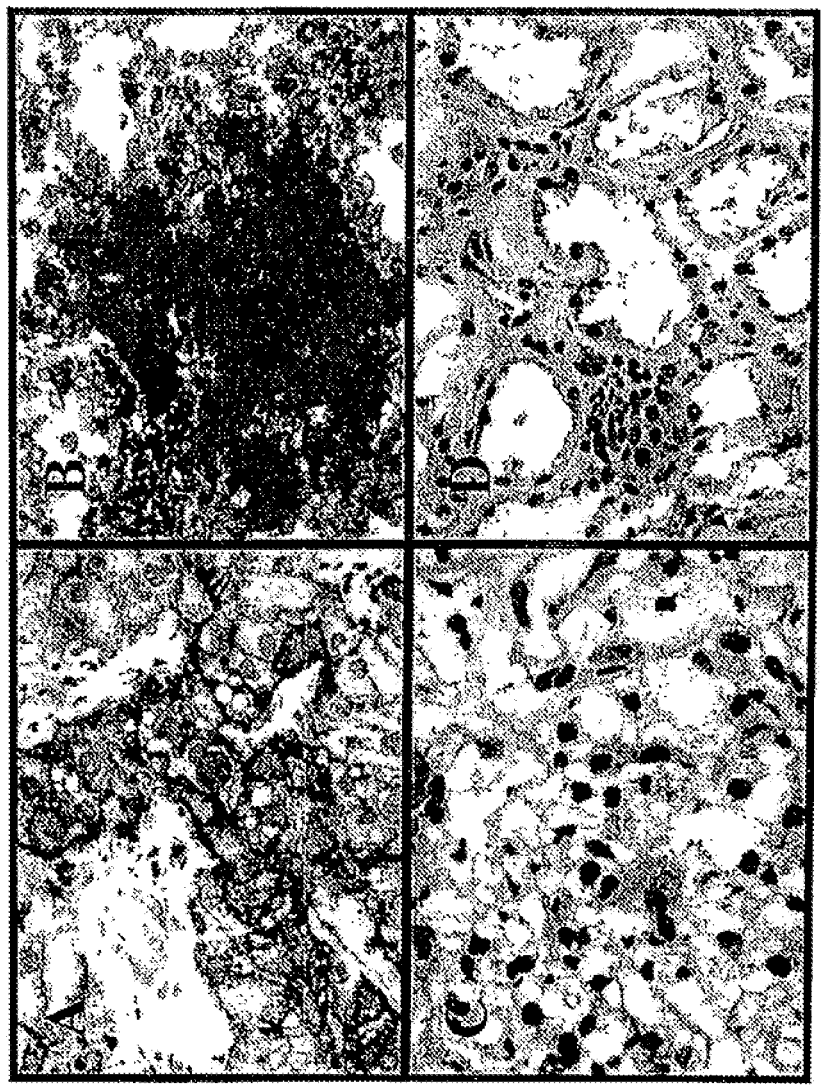
FIG. 1 is a series of photomicrographs (at a magnification of 400×) showing immunostaining (with an antibody specific for hB7-H1) of: an RCC specimen with high tumor cells hB7-H1 expression (FIG. 1A); an RCC specimen with high leukocyte hB7-H1 expression (FIG. 1B); an RCC specimen with no detectable hB7-H1 expression in either tumor cells or leukocytes (FIG. 1C); and a normal kidney specimen with no detectable hB7-H1 expression in the proximal tubules (FIG. 1D).

The inventors have discovered that renal cell carcinoma (RCC) patients who have increased levels of tumor cells and/or tumor-infiltrating leukocytes expressing the co-stimulatory glycoprotein hB7-H1 are at an increased risk of death from the RCC. In addition, elevated levels of hB7-H1 expressing tumor cells and/or tumor-infiltrating leukocytes was associated with more aggressive tumors and this association persisted even after controlling for traditional predictors of RCC progression, including, for example, tumor, node, metastasis (TNM) stage; primary tumor size; nuclear grade; and histological tumor necrosis.

Expression of B7-H1 in normal, non-activated mammalian cells is largely, if not exclusively, limited to macrophage-lineage cells and provides a potential costimulatory signal source for regulation of T cell activation. In contrast, aberrant expression of B7-H1 by tumor cells has been implicated in impairment of T cell function and survival, resulting in defective host antitumoral immunity.

The inventors found that human RCC tumors express hB7-H1. In particular, hB7-H1 was found to be expressed by both renal cell carcinoma (RCC) tumors and leukocytes infiltrating RCC tumors. In contrast, proximal tubules of the renal cortex, from which clear cell tumors are believed to arise, failed to express hB7-H1.

Clinical specimens were obtained from 196 patients who were treated with radical nephrectomy or nephron-sparing surgery for unilateral, clear cell RCC between 2000 and 2002 from the Mayo Clinic Nephrectomy Registry. Immunohistological detection and quantification of hB7-H1 expression in the specimens revealed that patients whose tumor specimens exhibited high intratumoral expression levels of hB7-H1 (contributed by tumor cells alone, leukocytes alone, or tumor and/or leukocytes combined) had aggressive tumors and were at markedly increased risk of death from RCC.

The combination of increased tumor cell hB7-H1 and tumor-infiltrating leukocyte hB7-H1 (high aggregate intratumoral hB7-H1) was an even stronger predictor of patient outcome than either hB7-H1-expressing tumor cells or tumor-infiltrating leukocytes alone. High aggregate intratumoral hB7-H1 expression levels were also significantly associated with regional lymph node involvement, distant metastases, advanced nuclear grade, and the presence of histologic tumor necrosis.

Based on its ability to impair function and survival of activated tumor-specific T cells, B7-H1, expressed by either tumor cells (e.g., RCC cells) or infiltrating leukocytes, can contribute to the immunosuppression that is commonly observed in subjects with cancer (e.g., RCC) and can serve as a critical determinant of the subjects' responses to immunotherapy for management of advanced cancer (e.g., IL-2, IL-12, IFN-α, vaccination or T-cell adoptive therapy). This raises the possibility that administering to cancer patients agents that interfere with the interaction of B7-H1 with its receptor (e.g., PD-1) can serve as a method of immunotherapy, particularly in subjects whose high level of intratumoral B7-H1 expression previously rendered them unresponsive or nearly unresponsive to other modes of immunotherapy.

These findings provide support for the methods of the invention, which are described below.

Methods of Diagnosis

The invention provides a method of diagnosing cancer in a subject. The method involves: (a) providing a tissue sample from a subject suspected of having, or likely to develop, cancer of the tissue, the sample containing test cells, the test cells being cells of the tissue or leukocytes infiltrating the tissue; and (b) assessing whether the test cells express B7-HL. Expression by some or all of the test cells is an indication that the subject has cancer. Since a wide variety of cancer cells express B7-H1 on their surfaces, the methods of the invention are particularly useful for diagnosing any such cancer. Test cells can thus be, for example, breast cells, lung cells, colon cells, pancreatic cells, renal cells, stomach cells, liver cells, bone cells, hematological cells (e.g., lymphoid cells, granulocytic cells, monocytes or macrophages), neural tissue cells, melanocytes, ovarian cells, testicular cells, prostate cells, cervical cells, vaginal cells, bladder cells, or any other cells listed herein. Moreover, test cells can be leukocytes present in relevant tissues containing any of the above-listed test cells. Leukocytes infiltrating the tissue can be T cells (CD4$^+$ T cells and/or CD8+ T cells) or B lymphocytes. Such leukocytes can also be neutrophils, eosinophils, basophils, monocytes, macrophages, histiocytes, or natural killer cells. Subjects can be mammals and include, for example, humans, non-human primates (e.g., monkeys, baboons, or chimpanzees), horses, cows (or oxen or bulls), pigs, sheep, goats, cats, rabbits, guinea pigs, hamsters, rats, gerbils, or mice.

As described herein, the invention provides a number of diagnostic advantages and uses. In the methods of the invention, the level of B7-H1 polypeptide and/or mRNA can be assessed. The level of B7-H1 is assessed in a tissue sample to diagnose, or to confirm, the presence of cancer in the subject from whom the tissue is obtained.

Methods of detecting a polypeptide in a tissue sample are known in the art. For example, antibodies (or fragments thereof) that bind to an epitope specific for B7-H1 can be used to assess whether test cells from the tissue sample express B7-H1. Such antibodies can be monoclonal or polyclonal antibodies. In such assays, the antibody itself, or a secondary antibody that binds to it, can be detectably labeled. Alternatively, the antibody can be conjugated with biotin, and detectably labeled avidin (a polypeptide that binds to biotin) can be used to detect the presence of the biotinylated antibody. Combinations of these approaches (including "multi-layer sandwich" assays) familiar to those in the art can be used to enhance the sensitivity of the methodologies. Some of these protein-detecting assays (e.g., ELISA or Western blot) can be applied to lysates of cells, and others (e.g., immunohistological methods or fluorescence flow cytometry) can be applied to histological sections or unlysed cell suspensions. The tissue sample can be, for example, lung, epithelial, connective, vascular, muscle, neural, skeletal, lymphatic, prostate, cervical, breast, spleen, gastric, intestinal, oral, esophageal, dermal, liver, kidney, bladder, thyroid, adrenal, brain, gallbladder, pancreatic, uterine, ovarian, or testicular tissue.

Methods of detecting an mRNA in a tissue sample are known in the art. For example, cells can be lysed and an mRNA in the lysates or in RNA purified or semi-purified from the lysates can be detected by any of a variety of methods including, without limitation, hybridization assays using detectably labeled gene-specific DNA or RNA probes (e.g., Northern Blot assays) and quantitative or semi-quantitative RT-PCR methodologies using appropriate gene-specific oligonucleotide primers. Alternatively, quantitative or semi-quantitative in situ hybridization assays can be carried out using, for example, tissue sections or unlysed cell suspensions, and detectably (e.g., fluorescently or enzyme) labeled DNA or RNA probes. Additional methods for quantifying mRNA include RNA protection assay (RPA) and SAGE.

Methods of assessing the level of B7-H1 expression (RNA and/or polypeptide) can be can be quantitative, semi-quantitative, or qualitative. Thus, for example, the level of B7-H1 expression can be determined as a discrete value. For example, where quantitative RT-PCR is used, the level of expression of B7-H1 mRNA can be measured as a numerical value by correlating the detection signal derived from the quantitative assay to the detection signal of a known concentration of: (a) B7-H1 nucleic acid sequence (e.g., B7-H1 cDNA or B7-H1 transcript); or (b) a mixture of RNA or DNA that contains a nucleic acid sequence encoding B7-H1. Alternatively, the level of B7-H1 expression can be assessed using any of a variety of semi-quantitative/qualitative systems known in the art. Thus, the level of expression of B7-H1 in a cell or tissue sample can be expressed as, for example, (a) one or more of "excellent", "good", "satisfactory", "unsatisfactory", and/or "poor"; (b) one or more of "very high", "high", "average", "low", and/or "very low"; or (c) one or more of "++++", "+++", "++", "+", "+/−", and/or "−". Where it is desired, the level of expression of B7-H1 in tissue from a subject can be expressed relative to the expression of B7-H1 from (a) a tissue of a subject known not be cancerous (e.g., a contralateral kidney or lung, or an uninvolved lymph node); or (b) a corresponding tissue from one or more other subjects known not to have the cancer of interest, preferably known not to have any cancer.

Methods of assessing the amount of label depend on the nature of the label and are well known in the art. Appropriate labels include, without limitation, radionuclides (e.g., $^{125}$I, $^{131}$I, $^{35}$S, $^{3}$H, or $^{32}$P), enzymes (e.g., alkaline phosphatase, horseradish peroxidase, luciferase, or β-glactosidase), fluorescent moieties or proteins (e.g., fluorescein, rhodamine, phycoerythrin, green fluorescent protein (GFP), or blue fluorescent protein (BFP)), or luminescent moieties (e.g., Qdot™ nanoparticles supplied by the Quantum Dot Corporation, Palo Alto, Calif.). Other applicable assays include quantitative immunoprecipitation or complement fixation assays.

In the diagnostic assays of the invention, a subject is diagnosed as having cancer if the proportion of test cells from the subject that express 87-H1 is greater than a control value. The control value, can be, for example: (a) the proportion of B7-H1-expressing cells in corresponding tissue of the subject known not be cancerous (e.g., a contralateral kidney or lung, or an uninvolved lymph node); or (b) the proportion of B7-H1 expressing cells in a corresponding tissue from one or more other subjects known not to have the cancer of interest, preferably known not to have any cancer.

The method of the invention can be used on its own or in conjunction with other procedures to diagnose cancer. For example, where it is desired or preferred, the level of B7-H1-expressing test cells in a tissue sample that is, or is suspected of being, cancerous can be assessed before, during, or after assessing the levels of other molecules that are useful diagnostic cancer markers. Such diagnostic markers can be, without limitation, tumor-associated antigens (TAA). Relevant TAA include, without limitation, carcinoembryonic antigen (CEA), MAGE (melanoma antigen) 1-4, 6, and 12, MUC (mucin) (e.g., MUC-1, MUC-2, etc.), tyrosinase, MART (melanoma antigen), Pmel 17 (gp100), GnT-V intron sequence (N-acetylglucosaminyltransferase V intron V sequence), PSA (prostate-specific antigen), PSMA (prostate-specific membrane antigen), PRAME (melanoma antigen), β-catenin, MUM-1-B (melanoma ubiquitous mutated gene product), GAGE (melanoma antigen) 1, BAGE (melanoma antigen) 2-10, c-ERB2 (HER2/neu), EBNA (Epstein-Barr Virus nuclear antigen) 1-6, gp75, human papilloma virus (HPV) E6 and E7, p53m lung resistance protein (LRP), Bcl-2, Ki-67, and VHL (von Hippel-Lindau) gene.

Method of Identifying Cancer Subjects Likely to Benefit from Immunotherapy

Another aspect of the invention is a method of identifying a candidate for immunotherapy. This method involves providing a tissue sample from a subject with cancer of the tissue. The tissue sample contains test cells, the test cells being cancer cells or tumor-infiltrating leukocytes. The level of test cells in the tissue sample that express B7-H1 is assessed, such that if B7-H1 expression is not detected in the test cells, or less than an immuno-inhibitory threshold level of the test cells express B7-H1, the subject is more likely to benefit from immunotherapy.

The immuno-inhibitory threshold level is a predetermined level of the relevant test cells expressing B7-H1. If the test cells from a cancer subject of interest contain a level of B7-H1-expressing cells that is less than the immuno-inhibitory threshold level of B7-H1-expressing cells (as predetermined for the relevant cancer), that subject is more likely to benefit from immunotherapy than another subject with the same cancer but whose corresponding test cells contain a level of B7-H1-expressing cells equal to, or greater than the immuno-inhibitory threshold level. The immuno-inhibitory threshold level can be obtained by performing statistical clinical analyses known in the art, e.g., those described herein.

Methods of assessing whether test cells express B7-H1 are the same as those described above for methods of diagnosis. Such methods, also as described above, can be qualitative, semi-quantitative, or qualitative.

"Immunotherapy" can be active immunotherapy or passive immunotherapy. For active immunotherapy, treatment relies on the in vivo stimulation of the endogenous host immune system to react against tumors with the administration of immune response-modifying agents. These immune-response-modifying agents are described below.

For passive immunotherapy, treatment involves the delivery of agents with established tumor-immune reactivity (such as immune effector cells or antibodies) that can directly, or indirectly mediate, anti-tumor effects and do not necessarily depend on an intact host immune system. Examples of immune effector cells include leukocytes, e.g., tumor-infiltrating leukocytes as discussed above, T lymphocytes (such as $CD8^+$ cytotoxic T lymphocytes and/or $CD4^+$ T-helper lymphocytes), killer cells (such as natural killer cells and lymphokine-activated killer cells), B cells and antigen-presenting cells (such as dendritic cells and macrophages).

Immunotherapy can also be one or more of the methods described below (in "Methods of Treatment" and "Methods of Inhibiting Expression of B7-H1).

Method of Prognosis

In another embodiment, the invention features a method of determining the prognosis of a subject with cancer. This method involves: (a) providing a tissue sample from a subject with cancer of the tissue, the tissue sample containing test cells, the test cells being cancer cells or tumor infiltrating leukocytes; and (b) assessing the level of test cells in the tissue sample that expresses B7-H1. If a prognostic level, or more than a prognostic level, of the test cells express B7-H1, the subject is more likely to die of the cancer than if less than a prognostic level of the test cells express B7-H1. The prognostic level is a predetermined value obtained by performing statistical clinical analyses known in the art, e.g., those described herein.

Thus, for example, if test cells from a cancer subject contain a significant level of B7-H1 expressing cells, but less than a prognostic level of B7-H1-expressing cells (as predetermined for the relevant cancer), the cancer subject will be no more likely to die of the cancer than a subject with the same cancer but whose corresponding test cells contain no detectable B7-H1-expressing cells. On the other hand, if test cells from a cancer subject contain more than a prognostic level of B7-H1-expressing cells, the cancer subject will be more likely to die of the cancer than a subject with the same cancer but whose corresponding test cells contain either no detectable B7-H1-expressing cells or a level of B7-H1-expressing cells lower than a prognostic level of B7-H1-expressing cells. Moreover, for subjects with cancer having levels of B7-H1-expressing cells in appropriate test cell populations greater than prognostic levels, the chances of dying from the cancer is likely to be proportional to the level of B7-H1-expressing cells in the test cell population.

As used herein, "assessing whether test cells express B7-H1" or "assessing the level of test cells in the tissue sample that express B7-H1" can be determined by any of the methods described above. Methods of prognosis will generally be quantitative or semi-quantitative.

Subjects can be any of those listed for "Methods of Diagnosis" and cancers can be any of the following: renal cancer, hematological cancer (e.g., leukemia or lymphoma), neurological cancer, melanoma, breast cancer, lung cancer, head and neck cancer, gastrointestinal cancer, liver cancer, pancreatic cancer, pancreatic cancer, genitourinary cancer, bone cancer, or vascular cancer Methods of Treatment The invention also includes a method of treatment. The method can involve: (a) identifying a subject with cancer, some or all cells of the cancer or some or all tumor-infiltrating leukocytes of the cancer expressing B7-H1; and (b) delivering to the subject an agent that interferes with an interaction between B7-H1 and a receptor for B7-H1. These methods can be performed subsequent to, or without, performing any of the above-described methods. The agent can be an antibody or an antibody fragment, such as, e.g., a Fab', a F(ab'), or a scFv fragment that binds B7-H1. The agent can also be a soluble B7-H1 or a soluble functional fragment of B7-H1; a soluble receptor for B7-H1 or a soluble functional fragment thereof; an antibody, or an antibody fragment, that binds to a receptor for B7-H1, e.g., the PD-1 receptor. The PD-1 receptor is described in greater detail in U.S. Pat. No. 6,808,710, the disclosure of which is incorporated herein by reference in its entirety.

In one embodiment, the agent itself is administered to a subject. Generally, the agent will be suspended in a pharmaceutically-acceptable carrier (e.g., physiological saline) and administered orally or by intravenous (i.v.) infusion, or injected subcutaneously, intramuscularly, intrathecally, intraperitoneally, intrarectally, intravaginally, intranasally, intragastrically, intratracheally, or intrapulmonarily. The agent can, for example, be delivered directly to a site of an immune response. e.g., a lymph node in the region of an affected tissue or organ or spleen. The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.0001-100.0 mg/kg. Wide variations in the needed dosage are to be expected in view of the variety of compounds available and the differing efficiencies of various routes of administration. For example, oral administration would be expected to require higher dosages than administration by i.v. injection. Variations in these dosage levels can be adjusted using standard empirical routines for optimization as is well understood in the art. Administrations can be single or multiple (e.g., 2-, 3-,4-,6-, 8-, 10-, 20-, 50-,100-, 150-, or more fold). Encapsulation of the compound in a suitable delivery vehicle (e.g., polymeric microparticles or implantable devices) may increase the efficiency of delivery, particularly for oral delivery.

Alternatively, where the agent is a polypeptide, a polynucleotide containing a nucleic acid sequence encoding the polypeptide can be delivered to appropriate cells in a mammal. Expression of the coding sequence can be directed to any cell in the body of the subject. However, expression will preferably be directed to cells in, or close to, lymphoid tissue draining an affected tissue or organ. Expression of the coding sequence can be directed, for example, to cells comprising the cancer tissue (e.g., tumor-infiltrating leukocytes and tumor cells) or immune-related cells, e.g., B cells, macrophages/monocytes, or interdigitating dendritic cells. This can be achieved by, for example, the use of polymeric, biodegradable microparticle or microcapsule delivery devices known in the art and/or tissue or cell-specific antibodies.

Another way to achieve uptake of the nucleic acid is using liposomes, which can be prepared by standard methods. The vectors can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells [Cristiano et al. (1995), J. Mol. Med. 73:479]. Alternatively, tissue specific targeting can be achieved by the use of tissue-specific transcriptional regulatory elements (TRE) which are known in the art. Delivery of "naked DNA" (i.e., without a delivery vehicle) to an intramuscular, intradermal, or subcutaneous site is another means to achieve in vivo expression.

In the relevant polynucleotides (e.g., expression vectors), the nucleic acid sequence encoding the polypeptide of interest with an initiator methionine and optionally a targeting sequence is operatively linked to a promoter or enhancer-promoter combination. Short amino acid sequences can act as signals to direct proteins to specific intracellular compartments. Such signal sequences are described in detail in U.S. Pat. No. 5,827,516, the disclosure of which is incorporated herein by reference in its entirety.

Enhancers provide expression specificity in terms of time, location, and level. Unlike a promoter, an enhancer can function when located at variable distances from the transcription initiation site, provided a promoter is present. An enhancer can also be located downstream of the transcription initiation site. To bring a coding sequence under the control of a promoter, it is necessary to position the translation initiation site of the translational reading frame of the peptide or polypeptide between one and about fifty nucleotides downstream (3') of the promoter. The coding sequence of the expression vector is operatively linked to a transcription terminating region.

Suitable expression vectors include plasmids and viral vectors such as herpes viruses, retroviruses, vaccinia viruses, attenuated vaccinia viruses, canary pox viruses, adenoviruses and adeno-associated viruses, among others.

Polynucleotides can be administered in a pharmaceutically acceptable carrier. Pharmaceutically acceptable carriers are biologically compatible vehicles that are suitable for administration to a human, e.g., physiological saline or liposomes. A therapeutically effective amount is an amount of the polynucleotide that is capable of producing a medically desirable result (e.g., decreased proliferation of cancer cells) in a treated subject. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately $10^6$ to approximately $10^{12}$ copies of the polynucleotide molecule. This dose can be repeatedly administered, as needed. Routes of administration can be any of those listed above.

In addition, the method can be an ex vivo procedure that involves providing a recombinant cell which is, or is a progeny of a cell, obtained from a subject and has been transfected or transformed ex vivo with one or more nucleic acids encoding one or more agents that interfere with an interaction between B7-H1 and a receptor for B7-H1, so that the cell expresses the agent(s); and administering the cell to the subject. The cells can be cells obtained from a cancer tissue (e.g., tumor cells and/or tumor-infiltrating leukocytes) or from a non-cancerous tissue obtained preferably from a subject to whom these cells are to be administered or from another subject. The donor and recipient of the cells can have identical major histocompatibility complex (MHC; HLA in humans) haplotypes. Optimally, the donor and recipient are homozygotic twins or are the same individual (i.e., are autologous). The recombinant cells can also be administered to recipients that have no, or only one, two, three, or four MHC molecules in common with the recombinant cells, e.g., in situations where the recipient is severely immunocompromised, where only mismatched cells are available, and/or where only short term survival of the recombinant cells is required or desirable.

The efficacy of the agent can be evaluated both in vitro and in vivo. Briefly, the agent can be tested for its ability, for example, to (a) inhibit the interaction between B7-H1 and a receptor for B7-H1, (b) inhibit growth of cancer cells, (c) induce death of cancer cells, or (d) render the cancer cells more susceptible to cell-mediated immune responses generated by leukocytes (e.g., lymphocytes and/or macrophages). For in vivo studies, the agent can, for example, be injected into an animal (e.g., a mouse cancer model) and its effects on cancer are then assessed. Based on the results, an appropriate dosage range and administration mute can be determined.

As used throughout the present application, the term "antibody" refers to a whole antibody (e.g., IgM, IgG, IgA, IgD, or IgE) molecule that is generated by any one of a variety of methods that are known in the art. The antibody can be a polyclonal or a monoclonal antibody. Also useful for the invention are chimeric antibodies and humanized antibodies made from non-human (e.g., mouse, rat, gerbil, or hamster) antibodies. As used herein, the term "antibody fragment" refers to an antigen-binding fragment, e.g., Fab, F(ab')$_2$, Fv, and single chain Fv (scFv) fragments. An scFv fragment is a single polypeptide chain that includes both the heavy and light chain variable regions of the antibody from which the scFv is derived.

Antibody fragments that contain the binding domain of the molecule can be generated by known techniques. For example: F(ab')$_2$ fragments can be produced by pepsin digestion of antibody molecules; and Fab fragments can be generated by reducing the disulfide bridges of F(ab')$_h$ fragments or by treating antibody molecules with papain and a reducing agent. See, e.g., National Institutes of Health, 1 *Current Protocols In Immunology*, Coligan et al., ed. 2.8, 2.10 (Wiley Interscience, 1991). scFv fragments can be produced, for example, as described in U.S. Pat. No. 4,642, 334, which is incorporated herein by reference in its entirety.

Chimeric and humanized monoclonal antibodies can be produced by recombinant DNA techniques known in the art, for example, using methods described in Robinson et al., International Patent Publication PCT/US86/02269; Akira et al., European Patent Application 184,187; Taniguchi, European Patent Application 171,496; Morrison et al., European Patent Application 173,494; Neuberger et al., PCT Application WO 86/01533; Cabilly et al., U.S. Pat. No. 4,816,567; Cabilly et al., European Patent Application 125,023; Better et al. (1988) Science 240, 1041-43; Liu et al. (1987) J. Immunol. 139, 3521-26; Sun et al. (1987) PNAS 84, 214-18; Nishimura et al. (1987) Canc. Res. 47, 999-1005; Wood et al. (1985) Nature 314, 446-49; Shaw et al. (1988) J. Natl. Cancer Inst. 80, 1553-59; Morrison, (1985) Science 229, 1202-07; Oi et al. (1986) BioTechniques 4, 214; Winter, U.S. Pat. No. 5,225,539; Jones et al. (1986) Nature 321, 552-25; Veroeyan et al. (1988) Science 239, 1534; and Beidler et al. (1988) J. Immunol. 141, 4053-60.

As used herein, a "functional fragment" of a B7-H1 receptor means a fragment of a receptor for B7-H1 that is smaller than the wild-type mature B7-H1 receptor and has at least 10% (e.g., at least 10%, at least 20%, at least 30%, at least 40%, at least 50%, at least 60%, at least 70%, at least 80%, at least 90%, at least 95%, at least 98%, at least 99%, or 100% or more) of the ability of the wild-type mature receptor for B7-H1 to bind to B7-H1. As used herein, a "functional fragment" of B7-H1 means a fragment of the wild-type mature B7-H1 polypeptide that is smaller than the wild-type mature B7-H1 polypeptide and has at least 10% (e.g., at least 10%, at least 20%, at least 30%, at least 40%, at least 50%, at least 60%, at least 70%, at least 80%, at least 90%, at least 95%, at least 98%, at least 99%, or 100% or more) of the ability of the wild-type mature B7-H1 to bind to the B7-H1 receptor. Methods of testing and comparing the ability of molecules to bind to each other are known to those in the art.

As used herein, the term "soluble" distinguishes the receptors used in the present invention from their cell membrane-bound counterparts. A soluble receptor, or a soluble functional fragment of a receptor can contain, for example, an extracellular (ligand binding) domain, but lack the transmembrane region that causes retention of a receptor on the cell surface. Methods of producing soluble receptors or fragments thereof are known in the an and include, for example, expressing a DNA fragment encoding an extracellular domain of a receptor in a suitable host cell/expression vector system.

The term "treatment", as used herein, means administration of an agent to a subject, who has cancer (or is suspected of having cancer), with the purpose to cure, alleviate, relieve, remedy, prevent, or ameliorate the disorder, the symptom of the disorder, the disease state secondary to the disorder, or the predisposition toward the disorder. An "effective amount" of a therapeutic agent (or composition) is an amount of the agent (or composition) that is capable of producing a medically desirable result in a treated subject. The method of the invention can be performed alone or in conjunction with other dugs or therapy.

As used herein, "prophylaxis" can mean complete prevention of the symptoms of a disease, a delay in onset of the symptoms of a disease, or a lessening in the severity of subsequently developed disease symptoms. As used herein, "therapy" can mean a complete abolishment of the symptoms of a disease or a decrease in the severity of the symptoms of the disease.

Methods of Inhibiting Expression of B7-H1

Another aspect of the invention is a method of inhibiting the expression of B7-H1 in a tumor cell or a tumor-infiltrating leukocyte. The method involves: (a) identifying a subject with cancer, the cancer containing a target cell that expresses B7-H1, the target cell being a tumor cell or a tumor-infiltrating leukocyte; and (b) introducing into the target cell: (i) an antisense oligonucleotide that hybridizes to a B7-H1 transcript, the antisense oligonucleotide inhibiting the expression of B7-H1 in the cell; or (ii) a B7-H1 interference RNA (RNAi). These methods can be performed subsequent to, or without, performing any of the above-described methods.

Since, as noted above, aberrant B7-H1 expression impairs the function and survival of tumor-specific T cells, it is likely that by inhibiting the cellular expression of B7-H1, as well as by interfering with the interaction between B7-H1 and its receptor, the anti-tumor immune responses can be restored. Thus, the method can be useful for therapy and/or prophylaxis of any cancer recited herein. The method can be used, for example, in the treatment of RCC.

Antisense compounds are generally used to interfere with protein expression either by, for example, interfering directly with translation of a target mRNA molecule, by RNAse-H-mediated degradation of the target mRNA, by interference with 5' capping of mRNA, by prevention of translation factor binding to the target mRNA by masking of the 5' cap, or by inhibiting of mRNA polyadenylation. The interference with protein expression arises from the hybridization of the antisense compound with its target mRNA. A specific targeting site on a target mRNA of interest for interaction with an antisense compound is chosen. Thus, for example, for modulation of polyadenylation, a preferred target site on an mRNA target is a polyadenylation signal or a polyadenylation site. For diminishing mRNA stability or degradation, destabilizing sequences are preferred target sites. Once one or more target sites have been identified, oligonucleotides are chosen which are sufficiently complementary to the target site (i.e., hybridize sufficiently well under physiological conditions and with sufficient specificity) to give the desired effect.

With respect to this invention, the term "oligonucleotide" refers to an oligomer or polymer of RNA, DNA, or a mimetic of either. The term includes oligonucleotides composed of naturally-occurring nucleobases, sugars, and covalent internucleoside (backbone) linkages. The normal linkage or backbone of RNA and DNA is a 3' to 5' phosphodiester bond. The term also refers however to oligonucleotides composed entirely of, or having portions containing, non-naturally occurring components which function in a similar manner to the oligonucleotides containing only naturally-occurring components. Such modified substituted oligonucleotides are often preferred over native forms because of desirable properties such as, for example, enhanced cellular uptake, enhanced affinity for target sequence, and increased stability in the presence of nucleases. In the mimetics, the core base (pyrimidine or purine) structure is generally preserved but (1) the sugars are either modified or replaced with other components and/or (2) the inter-nucleobase linkages are modified. One class of nucleic acid mimetic that has proven to be very useful is referred to as protein nucleic acid (PNA). In PNA molecules the sugar backbone is replaced with an amide-containing backbone, in particular an aminoethylglycine backbone. The bases are retained and are bound directly to the aza nitrogen atoms of the amide portion of the backbone. PNA and other mimetics useful in the instant invention are described in detail in U.S. Pat. No. 6,210,289, the disclosure of which is incorporated herein by reference in its entirety.

The antisense oligomers to be used in the methods of the invention generally comprise about 8 to about 100 (e.g., about 14 to about 80 or about 14 to about 35) nucleobases (or nucleosides where the nucleobases are naturally occurring).

The antisense oligonucleotides can themselves be introduced into a cell or an expression vector containing a nucleic sequence (operably linked to a TRE) encoding the antisense oligonucleotide can be introduced into the cell. In the latter case, the oligonucleotide produced by the expression vector is an RNA oligonucleotide and the RNA oligonucleotide will be composed entirely of naturally occurring components.

Where antisense oligonucleotides per se are administered, they can be suspended in a pharmaceutically-acceptable carrier (e.g., physiological saline) and administered under the same conditions described above for agents that interfere with an interaction between B7-H1 and a receptor for B7-H1.

Where an expression vector containing a nucleic sequence (operably linked to a TRE) encoding the antisense oligonucleotide is administered to a subject, expression of the coding sequence can be directed to a tumor cell of tumor-infiltrating leukocyte in the body of the subject using any of the cell- or tissue-targeting techniques described above for vectors that express polypeptides that interfere with an interaction between B7-H1 and a receptor for B7-H1.

Double-stranded interfering RNA (RNAi) homologous to B7-H1 DNA can also be used to reduce expression of B7-H1 in tumor cells and/or tumor-infiltrating leukocytes. See, e.g., Fire et al. (1998) Nature 391:806-811; Romano and Masino (1992) Mol. Microbiol. 6:3343-3353; Cogoni et al. (1996) EMBO J. 15:3153-3163; Cogoni and Masino (1999) Nature 399:166-169; Misquitta and Paterson (1999) Proc. Natd. Acad. Sci. USA 96:1451-1456; andKennerdell and Carthew (1998) Cell 95:1017-1026. The disclosures of all these articles are incorporated herein by reference in their entirety.

The sense and anti-sense RNA strands of RNAi can be individually constructed using chemical synthesis and enzymatic ligation reactions using procedures known in the art. For example, each strand can be chemically synthesized using naturally occurring nucleotides or variously modified nucleotides designed to increase the biological stability of the molecule or to increase the physical stability of the duplex formed between the sense and anti-sense strands, e.g., phosphorothioate derivatives and acridine substituted nucleotides. The sense or anti-sense strand can also be produced biologically using an expression vector into which a target B7-H1 sequence (full-length or a fragment) has been subcloned in a sense or anti-sense orientation. The sense and anti-sense RNA strands can be annealed in vitro before delivery of the dsRNA to cells. Alternatively, annealing can occur in vivo after the sense and anti-sense strands are sequentially delivered to tumor cells and/or tumor-infiltrating leukocytes.

Double-stranded RNAi interference can also be achieved by introducing into tumor cells and/or tumor-infiltrating leukocytes a polynucleotide from which sense and anti-sense RNAs can be transcribed under the direction of separate promoters, or a single RNA molecule containing both sense and anti-sense sequences can be transcribed under the direction of a single promoter.

It will be understood that certain drugs and small molecules can also be used inhibit expression of B7-H1 in tumor cells and/or tumor-infiltrating leukocytes.

One of skill in the art will appreciate that RNAi, drug, and small molecule methods can be, as for the antisense methods described above, in vitro and in vivo. Moreover, methods and conditions of delivery are the same as those for antisense oligonucleotides.

In any of the above methods of inhibiting the interaction between B7-H1 and a receptor for B7-H1 and of inhibiting expression of B7-H1, one or more agents (e.g., two, three, four, five, six, seven, eight, nine, ten, 11, 12, 15, 18, 20, 25, 30, 40, 50, 60, 70, 80, 100, or more) including, for example, inhibitory compounds, antisense oligonucleotides, RNAi, drugs, or small molecules (or vectors encoding them), can be used.

Moreover, such agents can be used together with one or more (e.g., two, three, four, five, six, seven, eight, nine, ten, 11, 12, 15, 18, 20, 25, 30, 40, 50, 60, 70, 80, 100, or more) supplementary agents, including immunomodulatory cytokines, growth factors, antiangiogenic factors, immunogenic stimuli, and/or antibodies specific for any of these. Such supplementary agents can administered before, simultaneous with, or after delivery of any of the above-listed agents.

Examples of immunomodulatory cytokines, growth factors, and antiangiogenic factors include, without limitation, interleukin (IL)-1 to 25 (e.g., IL-2, IL-12, or IL-15), interferon-γ (IFN-γ), interferon-α (IFN-α), interferon-β (IFN-β), tumor necrosis factor-α (TNF-α), granulocyte macrophage colony stimulating factor (GM-CSF), granulocyte macrophage colony stimulating factor (G-CSF), endostatin, angiostatin, and thrombospondin. Immunomodulatory cytokines, growth factors, antiangiogenic factors include substances that serve, for example, to inhibit infection (e.g., standard anti-microbial antibiotics), inhibit activation of T cells, or inhibit the consequences of T cell activation. For example, where it is desired to decrease a Th1-type immune response (e.g., in a DTH response), a cytokine such as interleukin (IL)-4, IL-10, or IL-13 or an antibody specific for a cytokine such as IL-12 or interferon-γ (IFN-γ) can be used. Alternatively, where it is desired to inhibit a Th2-type immune response (e.g., in an immediate type hypersensitivity response), a cytokine such as IL-12 or IFN-γ or an antibody specific for IL-4, IL-10, or IL-13 can be used as a supplementary agent. Also of interest are antibodies (or any of the above-described antibody fragments or derivatives) specific for proinflammatory cytokines and chemokines such as 11-1, IL-6, IL-8, tumor necrosis factor-α (TNF-α), macrophage inflammatory protein (MIP)-1, MIP-3α, monocyte chemoattractant protein-1 (MCP-1), epithelial neutrophil activating peptide-78 (ENA-78), interferon-γ-inducible protein-10 (IP10), Rantes, and any other appropriate cytokine or chemokine recited herein.

In some instances, it may be desired to increase the immune response in a subject by the administration of one or more immune response modifying-agents. Such immune response-modifying agents include, in addition to any of the immunomodulatory cytokines, growth factors, and angiogenic factors listed above, immunogenic stimuli that can be delivered via the antigen-specific T cell receptor (TCR) expressed on the surface of the T cell. More commonly, but not necessarily, such a stimulus is provided in the form of an antigen for which the TCR is specific. While such antigens will generally be protein, they can also be carbohydrates, lipids, nucleic acids or hybrid molecules having components of two or more of these molecule types, e.g., glycoproteins or lipoproteins. However, the immunogenic stimulus can also be provided by other agonistic TCR ligands such as antibodies specific for TCR components (e.g., TCR α-chain or β-chain variable regions) or antibodies specific for the TCR-associated CD3 complex. Antigens useful as immunogenic stimuli include alloantigens (e.g., a MHC alloantigen) on, for example, an antigen presenting cell (APC)(e.g., a dendritic cell (DC), a macrophage, a monocyte, or a B cell). DC of interest are interdigitating DC and not follicular DC; follicular DC present antigen to B cells. For convenience, interdigitating DC are referred to herein as DC. Methods of isolating DC from tissues such as blood, bone marrow, spleen, or lymph node are known in the art, as are methods of generating them in vitro from precursor cells in such tissues.

Also useful as immunogenic stimuli are polypeptide antigens and peptide-epitopes derived firm them (see below). Unprocessed polypeptides are processed by APC into peptide-epitopes that are presented to responsive T cells in the form of molecular complexes with MHC molecules on the surface of the APC. Useful immunogenic stimuli also include a source of antigen such as a lysate of either tumor cells or cells infected with an infectious microorganism of interest. APC (e.g., DC) pre-exposed (e.g., by coculturing) to antigenic polypeptides, peptide-epitopes of such polypeptides or lysates of tumor (or infected cells) can also be used as immunogenic stimuli. Such APC can also be "primed" with antigen by culture with a cancer cell or infected cell of interest; the cancer or infected cells can optionally be irradiated or heated (e.g., boiled) prior to the priming culture. In addition, APC (especially DC) can be "primed" with either total RNA, mRNA, or isolated TAA-encoding RNA.

Alternatively, an immunogenic stimulus be provided in the form of cells (e.g., tumor cells or infected cells producing the antigen of interest). In addition, immunogenic stimuli can be provided in the form of cell hybrids formed by fusing APC (e.g., DC) with tumor cells [Gong et al. (2000) Proc. Natl. Acad. Sci. USA 97(6):2716-2718; Gong et al. (1997) Nature Medicine 3(5):558-561; Gong et al. (2000) J. Immunol. 165(3):1705-1711] or infected cells of interest.

Also useful as immunogenic stimuli are heat shock proteins bound to antigenic peptide-epitopes derived from antigens (e.g., tumor-associated antigens or antigens produced by infectious microorganisms) [Srivastava (2000) Nature Immunology 1(5):363-366]. Heat shock proteins of interest include, without limitation, glycoprotein 96 (gp96), heat shock protein (hsp) 90, hsp70, hsp110, glucose-regulated protein 170 (grp170) and calreticulin. Immunogenic stimuli can include one or more (e.g., one, two, three, four, five, six, seven, eight, nine, ten, more) heat shock proteins isolated from tumor cells. Such tumor are preferably, but not necessarily, from the same subject (i) to whom the agent that interferes with the interaction between B7-H1 and a receptor for B7-H1 is to be delivered or (ii) in whose tumor cells or tumor infiltrating leukocytes the expression of B7-H1 is to be inhibited. The tumor cells can also be obtained, for example, from another individual having the same as the subject, or a related tumor-type. Alternatively, the heat shock protein can be isolated from mammalian cells expressing a transcriptome prepared from tumor cells of interest.

As indicated above, immunogenic stimuli useful in the invention can be any of a wide variety of tumor cells, APC"primed" with tumor cells, hybrid cells, or TAA (see above), peptide-epitopes of such TAA, and APC "primed" with TAA or peptide-epitopes of them. As used herein, a "TAA" is a molecule (e.g., a protein molecule) that is expressed by a tumor cell and either (a) differs qualitatively from its counterpart expressed in normal cells, or (b) is expressed at a higher level in tumor cells than in normal cells. Thus, a TAA can differ (e.g., by one or more amino acid residues where the molecule is a protein) from, or it can be identical to, its counterpart expressed in normal cells. It is preferably not expressed by normal cells. Alternatively, it is expressed at a level at least two-fold higher (e.g., a two-fold, three-fold, five-fold, ten-fold, 20-fold, 40-fold, 100-fold, 500-fold, 1,000-fold, 5,000-fold, or 15,000-fold higher) in a tumor cell than in the tumor cell's normal counterpart. Relevant TAA include, without limitation, any of the TAAs listed above.

Administrations of the agents and/or the one or more supplementary agents can be systemic (e.g., intravenous) or local, e.g., during surgery by direct injection or infusion into the tissue that comprises the cells of the cancer and/or tumor-infiltrating leukocytes. The administrations can also be by any of routes, doses, and schedules recited herein.

In addition, it is understood that the above-described methods can be used in combination with any one of a variety of other therapeutic modalities known in the art, such as, without limitation, chemotherapy, immunotherapy, radiotherapy, or gene therapy.

In both of the methods of inhibiting the interaction between B7-H1 and a receptor for B7-H1 and the methods of inhibiting expression of B7-H1, the cancer can be any cancer recited herein and includes, e.g., renal cell carcinoma. Subjects can be mammals and include, for example, humans, non-human primates (e.g., monkeys, baboons, or chimpanzees), horses, cows (or oxen or bulls), pigs, sheep, goats, cats, rabbits, guinea pigs, hamsters, rats, gerbils, or mice.

The following examples are meant to illustrate, not limit, the invention.

EXAMPLES

Example 1. Materials and Methods

Patient Selection

Upon approval from the Mayo Clinic Institutional Review Board, 429 patients were identified from Mayo Clinic Nephrectomy Registry that were previously treated with radical nephrectomy or nephron-sparing surgery for unilateral, sporadic clear cell RCC between 2000 and 2002. Since pathologic features and patient outcome differ by RCC subtype, all analyses were restricted to patients treated with clear cell RCC only, the most common of the RCC subtypes [Cheville et al. (2003) Am. J. Surg. Pathol. 27:612-624]. Since the hB7-H1-specific monoclonal antibody, 5H1 (see below), can reproducibly stain fresh-frozen, but not paraffin-fixed, tissue [Dong et al. (2002) Nature Med. 8:793-800], patients were selected based on availability of fresh-frozen tissue.

Pathologic Features

The pathologic features examined included histologic subtype, tumor size, primary tumor stage, regional lymph node involvement, and distant metastases at nephrectomy (2002 TNM), nuclear grade, and histologic tumor necrosis. The microscopic slides from all specimens were reviewed by a urologic pathologist without prior knowledge of patient outcome. Histologic subtype was classified according to the Union Internationale Contre le Cancer, American Joint Committee on Cancer, and Heidelberg guidelines [Storkel et al. (1997) Cancer 80:987-989; Kovacs et al. (1997) J. Pathol. 183:131-133]. Nuclear grade was assigned using standardized criteria [Lohse et al. (2002) Am. J. Clin. Pathol. 118:877-886]. Histologic tumor necrosis was defined as the presence of any microscopic coagulative tumor necrosis. Degenerative changes such as hyalinization, hemorrhage, and fibrosis were not considered necrosis.

Immunohistochemical Staining of Tumor Specimens

Cryosections generated from RCC tumors and normal renal cortical specimens (5 μm thickness) were mounted on Superfrost Plus slides, air dried, and fixed in ice-cold acetone. Sections were stained using the Dako Autostainer and Dako Cytomnation Labeled Polymer (EnVision+) HRP detection Kit™ (Dako; Carpinteria, Calif.). Slides were blocked with $H_2O_2$ for 10 minutes followed by incubation with the primary anti-B7-H1 antibody for 30 minutes at room temperature. A horseradish peroxidase-conjugated secondary reagent (goat anti-mouse immunoglobulin) was then applied to the slides at room temperature for 15 minutes followed by incubation with chromogen-substrate for 10 minutes. Finally, sections were counter-stained for 3 minutes with modified Schmidt's Hematoxylin. The primary antibody used in this study was 5H1, a mouse anti-hB7-H1 monoclonal antibody [Dong et al. (2002) Nature Med. 8:793-800). Benign renal tumors and peripheral T cells were not stained in this study. Positive tissues controls for hB7-H1 staining were human tonsillar tissues. Irrelevant isotype-matched antibodies were used to control for non-specific staining.

Quantification of hB7-H1 Expression

The percentages of tumor cells and leukocytes that stained positive for hB7-H1 were quantified in 5-10% increments by a urologic pathologist without prior knowledge of patient outcome. The extent of leukocytic infiltration was assessed and recorded as absent, focal (scattered lymphoid aggregates), moderate, or marked. An adjusted score representing leukocytic hB7-H1 expression was calculated as the percentage of leukocytes that stained positive for hB7-H1 multiplied by the extent of leukocytic infiltration (0=absent, 1=focal, 2=moderate, 3=marked).

Statistical Methods

Comparisons between the pathologic features and hB7-H1 expression were evaluated using chi-square, Fisher's exact and Wilcoxon rank sum tests. Cancer-specific survival was estimated using the Kaplan-Meier method. The duration of follow-up was calculated from the date of nephrectomy to the date of death or last follow-up. Cause of death was determined from the death certificate or physician correspondence. Scatter plots of the percentage of cells that stained positive for hB7-H1 versus the difference in observed survival and the survival expected from a Cox proportional hazards regression model (formally known as a Martingale residual) were used to identify potential cut-off points for hB7-H1 expression [Therneau et al. (2000) Modeling Survival Data: Extending the Cox Model, ed. 1 (Springer-Verlag, Ann Arbor), pp. 87-92]. The associations of these cut points with death from RCC were evaluated using Cox proportional hazards regression models univariately and after adjusting for primary tumor stage, regional lymph node involvement, distant metastases, tumor size, nuclear grade, and histologic tumor necrosis, one feature at a time. The association of hB7-H1 expression with death from RCC was also adjusted for the Mayo Clinic SSIGN (Stage, Size, Grade, and Necrosis) Score, a prognostic composite score specifically developed for patients with clear cell RCC [Frank et al. (2002) J. Urol. 168:2395-2400]. Statistical analyses were performed using the SAS software package (SAS Institute, Cary, North Carolina) and p-values<0.05 were considered statistically significant.

Example 2. Survival of RCC Patients with Fresh-Frozen Tissue Samples Available

Of the 429 patients eligible for the study, 196 (46%) had fresh-frozen tissue available for laboratory investigation. Patients with fresh-frozen tissues had larger tumors compared with those who did not (median tumor size 6.0 cm versus 5.0 cm; p=0.008). However, no other feature studied was significantly different between the two groups. Furthermore, there was not a statistically significant difference in cancer-specific survival between patients with and without fresh-frozen tissues (p=0.314).

At last follow-up, 39 of the 196 patients studied had died, including 30 patients who died from clear cell RCC at a median of 1.1 years following nephrectomy (range 0-2.5). Among the 157 patients who were still alive at last follow-up, the median duration of follow-up was 2.0 years (range 0-4.1). The estimated cancer-specific survival rates (standard error, number still at risk) at 1, 2, and 3 years following nephrectomy were 91.4% (2.1%, 148), 81.8% (3.3%, 78), and 77.9% (3.8%, 30), respectively.

Example 3. Correlation of hB7-H1 Expression in RCC Tumor Cells with Patient Outcome Immunohistochemical staining of the 196 clear cell RCC specimens revealed either no hB7-H1 expression by RCC tumor cells, or varying degrees of hB7-H1 expressed by either RCC tumor cells and/or RCC tumor-infiltrating leukocytes (Tables 1 and 2 and FIG. 1). In addition, proximal tubules within the renal cortex, from which RCC tumors are believed to arise, exhibited no hB7-H1 expression among the 20 normal renal cortical specimens studied (FIG. 1).

The percentages of tumor cells that stained positive for hB7-H1 for the 196 specimens studied are summarized in Table 1. A scatter plot of tumor hB7-H1 expression versus the expected risk of death for each patient suggested that a cut point of 10% would be appropriate for these data. There were 73 (37.2%) patients with specimens that had ≥10% tumor cell hB7-H1 expression.

TABLE 1

Percent Tumor hB7-H1 Expression in 196 Clear Cell RCC Specimens

| % hB7-H1 Expression | N (%) |
|---|---|
| 0 | 66 (33.7) |
| 5 | 57 (29.1) |
| 10 | 27 (13.8) |
| 15 | 4 (2.0) |
| 20 | 15 (7.7) |
| 75 | 3 (1.5) |
| 30 | 6 (3.1) |
| 40 | 2 (1.0) |
| 50 | 4 (2.0) |
| 60 | 3 (1.5) |
| 70 | 3 (1.5) |
| 80 | 2 (1.0) |
| 90 | 3 (1.5) |
| 100 | 1 (0.5) |

TABLE 2

Adjusted Score for Leukocyte hB7-H1 Expression in 196 Clear Cell RCC Specimens

| Leukocytic Infiltration* | % Hb7-H1 Expression | Adjusted Score | N (%) |
|---|---|---|---|
| 0 | 0 | 0 | 81 (41.3) |
| 1 | 5 | 5 | 4 (2.0) |
| 1 | 10 | 10 | 1 (0.5) |
| 1 | 30 | 30 | 2 (1.0) |
| 1 | 50 | 50 | 4 (2.0) |
| 1 | 60 | 60 | 3 (1.5) |
| 1 | 70 | 70 | 22 (11.2) |
| 1 | 80 | 80 | 12 (6.1) |
| 1 | 90 | 90 | 10 (5.1) |

TABLE 2-continued

Adjusted Score for Leukocyte hB7-H1 Expression
in 196 Clear
Cell RCC Specimens

| Leukocytic Infiltration* | % Hb7-H1 Expression | Adjusted Score | N (%) |
|---|---|---|---|
| 2 | 5 | 10 | 3 (1.5) |
| 2 | 10 | 20 | 4 (2.0) |
| 2 | 20 | 40 | 2 (1.0) |
| 2 | 30 | 60 | 2 (1.0) |
| 2 | 50 | 100 | 6 (3.1) |
| 2 | 60 | 120 | 1 (0.5) |
| 2 | 70 | 140 | 9 (4.6) |
| 2 | 80 | 160 | 7 (3.6) |
| 2 | 90 | 180 | 8 (4.1) |
| 3 | 5 | 15 | 1 (0.5) |
| 3 | 20 | 60 | 1 (0.5) |
| 3 | 30 | 90 | 4 (2.0) |
| 3 | 70 | 210 | 2 (1.0) |
| 3 | 80 | 240 | 4 (2.0) |
| 3 | 90 | 270 | 2 (1.0) |
| 3 | 100 | 300 | 1 (0.5) |

*The extent of leukocytic infiltration was recorded as
0 = absent,
1 = focally present,
2 = moderately present, or
3 = markedly present.

Figure 2:
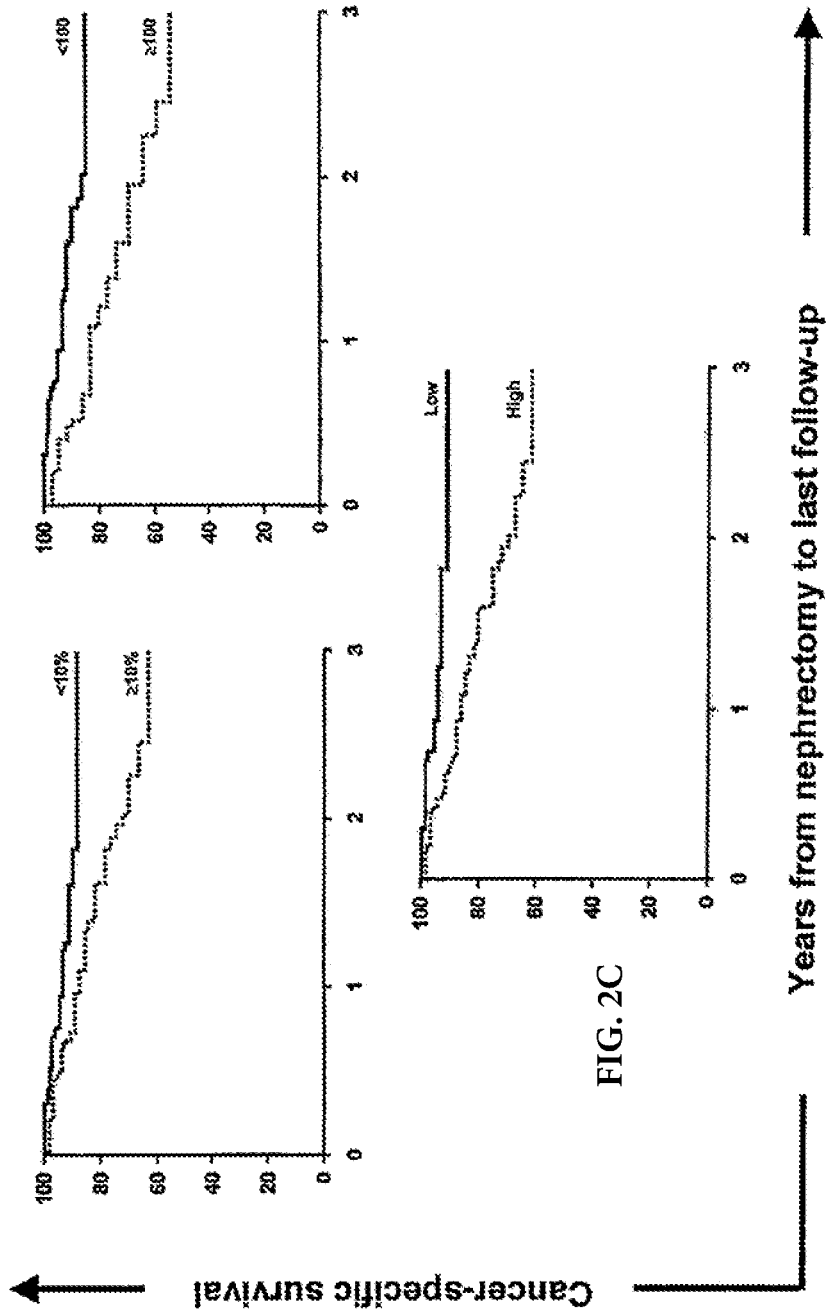
FIGS. 2A-C are a series of line graphs showing the associations of hB7-H1 expression with death from RCC in 196 subjects from whom the clear cell RCC specimens were obtained for analysis.

The associations of tumor hB7-H1 expression with death from RCC, both univariately and after adjusting for TNM stage, tumor size, nuclear grade, and histologic tumor necrosis are shown in Table 3. Univariately, patients with specimens that had ≥10% tumor hB7-H1 expression were close to 3 times more likely to die from RCC compared with patients with specimens that had <10% expression (risk ratio 2.91; 95% CI 1.39-6.13; p=0.005; FIG. 2A). In multivariate analyses, patients with specimens that had ≥10%/tumor hB7-H1 expression were significantly more likely to die from RCC, even after adjusting for primary tumor stage, distant metastases, or primary tumor size.

TABLE 3

Associations of hB7-H1 Expression with
Death from RCC in 196 Clear Cell
RCC Specimens

| | Risk Ratio (95% CI)* | P-value |
|---|---|---|
| Tumor hB7-H1 Expression ≥10% | | |
| Univariate Model | 2.91 (1.39-6.13) | 0.005 |
| Adjusted for: | | |
| 2002 Primary Tumor Stage (T) | 2.83 (1.34-5.96) | 0.006 |
| Regional Lymph Node Involvement (N) | 1.97 (0.87-4.45) | 0.103 |
| Distant Metastases (M) | 2.24 (1.06-4.73) | 0.035 |
| Primary Tumor Size | 2.88 (1.37-6.06) | 0.005 |
| Nuclear Grade | 1.96 (0.90-4.30) | 0.092 |
| Histologic Tumor Necrosis | 1.69 (0.78-3.65) | 0.183 |
| Leukocytic hB7-H1 Expression ≥100 | | |
| Univariate Model | 3.58 (1.74-7.37) | <0.001 |
| Adjusted for: | | |
| 2002 Primary Tumor Stage (T) | 3.34 (1.62-6.90) | 0.001 |
| Regional Lymph Node Involvement (N) | 3.59 (1.74-7.41) | <0.001 |
| Distant Metastases (M) | 2.16 (1.03-4.53) | 0.042 |
| Primary Tumor Size | 2.64 (1.27-5.46) | 0.009 |
| Nuclear Grade | 3.03 (1.46-6.29) | 0.003 |
| Histologic Tumor Necrosis | 2.87 (1.39-5.95) | 0.004 |
| High Aggregate Intratumoral hB7-H1 Expression | | |
| Univariate Model | 4.53 (1.94-10.56) | <0.001 |
| Adjusted for: | | |
| 2002 Primary Tumor Stag (T) | 4.07 (1.74-9.51) | 0.001 |
| Regional Lymph Node Involvement (N) | 3.36 (1.39-8.16) | 0.007 |
| Distant Metastases (M) | 3.12 (1.32-7.38) | 0.009 |
| Primary Tumor Size | 4.25 (1.82-9.91) | <0.001 |
| Nuclear Grade | 3.09 (1.28-7.50) | 0.012 |
| Histologic Tumor Necrosis | 2.68 (1.12-6.42) | 0.027 |

*Risk ratios represent the risk of death from clear cell RCC for the feature listed, either univariately or after multivariate adjustment. For example, patients with specimens that had ≥10% tumor hB7-H1 expression were 2.9 times more likely to die from RCC compared with patients with specimens that had <10% tumor hB7-H1 expression, even after adjusting for primary tumor size (p = 0.005).

The adjusted scores for leukocytic hB7-H1 expression are summarized in Table 2. There were 40 (20.4%) specimens with an adjusted leukocyte hB7-H1 score of 100 or greater (essentially moderate or marked leukocytic infiltration with at least 50% of the leukocytes staining positive for hB7-H1), which appeared to be a reasonable cut point to examine and illustrate the association of this feature with patient outcome. The associations of leukocyte hB7-H1 expression with death from RCC are summarized in Table 3. Univariately, patients with specimens that had an adjusted leukocyte hB7-H1 score ≥100 were 3.6 times more likely to die from RCC compared with patients that had specimens with scores <100 (risk ratio 3.58; 95% CI 1.74-7.37; p<0.001; FIG. 2B). Patients with specimens that demonstrated high levels of leukocyte hB7-H1 expression were significantly more likely to die from RCC even after adjusting for TNM stage, primary tumor size, nuclear grade, or histologic tumor necrosis.

Since both tumor and leukocyte hB7-H1 expression were significantly associated with patient outcome both univariately and after multivariate adjustment, the combination of these two features were evaluated. There were 87 (44.4%) specimens that had either ≥10% tumor hB7-H1 expression or an adjusted score for leukocyte hB7-H1 expression ≥100 (i.e., high aggregate intratumoral hB7-H1 expression). Twenty-six (13.3%) of these specimens had both features. Conversely, 109 (55.6%) specimens had <10% tumor hB7-H1 expression and <100 leukocyte hB7-H1 expression (i.e., low aggregate intratumoral hB7-H1 expression). The associations of this combined feature with death from RCC are summarized in Table 3. Univariately, patients with specimens that had high aggregate intratumoral hB7-H1 expression were 4.5 times more likely to die from RCC compared with patients with specimens that had both <10% tumor expression and <100 leukocyte expression (risk ratio 4.53; 95% CI 1.94-10.56; p<0.001). After adjusting for the Mayo Clinic SSIGN Score, patients with high aggregate intratumoral hB7-H1 expression remained over twice as likely to die from RCC compared with patients with low aggregate intratumoral hB7-H1, although this difference did not attain statistical significance (risk ratio 2.19; 95% CI 0.91-5.24; p=0.079). However, patients with specimens that had high aggregate intratumoral hB7-H1 expression were significantly more likely to die from RCC after adjusting for TNM stage, primary tumor size, nuclear grade, and histologic tumor necrosis, one feature at a time. The association of combined tumor and leukocyte hB7-H1 expression with the pathologic features under study were also investigated. High aggregate intratumoral hB7-H1 expression levels were significantly associated with regional lymph node involvement, distant metastases, advanced nuclear grade, and the presence of histologic tumor necrosis (Table 4).

TABLE 4

Associations of Tumor and Leukocyte hB7-H1 Expression with Pathologic Features in 196 Dear Cell RCC Specimens

| Feature | High Aggregate Intratumoral hB7-H1 Expression | | P-value |
|---|---|---|---|
| | No N = 109 N (%) | Yes N = 87 N (%) | |
| 2002 Primary Tumor Stage | | | |
| pT1 and pT2 | 88 (80.7) | 62 (71.3) | 0.120 |
| pT3 and pT4 | 21 (19.3) | 25 (28.7) | |
| Regional Lymph Node Involvement | | | |
| pNx and pN0 | 108 (99.1) | 76 (87.4) | <0.001 |
| pN1 and pN2 | 1 (0.9) | 11 (12.6) | |

TABLE 4-continued

Associations of Tumor and Leukocyte hB7-H1 Expression with Pathologic Features in 196 Dear Cell RCC Specimens

| Feature | High Aggregate Intratumoral hB7-H1 Expression | | P-value |
|---|---|---|---|
| | No N = 109 N (%) | Yes N = 87 N (%) | |
| Distant Metastases | | | |
| pM0 | 99 (90.8) | 69 (79.3) | 0.022 |
| pM1 | 10 (9.2) | 18 (20.7) | |
| Primary Tumor Size | | | |
| <5 cm | 46 (42.2) | 25 (28.7) | 0.051 |
| ≥5 cm | 63 (57.8) | 62 (71.3) | |
| Nuclear Grade | | | |
| 1 and 2 | 69 (63.3) | 23 (26.4) | <0.001 |
| 3 | 6 (33.0) | 50 (57.5) | |
| 4 | 4 (3.7) | 14 (16.1) | |
| Histologic Tumor Necrosis | | | |
| Absent | 94 (86.2) | 55 (63.2) | <0.001 |
| Present | 15 (13.8) | 32 (36.8) | |

A number of embodiments of the invention have been described. Nevertheless, it will be understood that various modifications may be made without departing from the spirit and scope of the invention. Accordingly, other embodiments are within the scope of the following claims.

What is claimed is:

1. A method for treating renal cell carcinoma in a human comprising administering, to said human, an anti-PD-1 antibody that interferes with an interaction between B7-H1 and PD-1, wherein some or all cells of said renal cell carcinoma express B7-H1.

2. The method of claim 1, wherein said anti-PD-1 antibody is an IgG antibody.

3. The method of claim 1, wherein ≥10 percent of said cells of said renal cell carcinoma express B7-H1.

* * * * *